(12) United States Patent
Milstein et al.

(10) Patent No.: US 10,562,767 B2
(45) Date of Patent: Feb. 18, 2020

(54) LIQUID-ORGANIC HYDROGEN CARRIER SYSTEMS BASED ON CATALYTIC PEPTIDE FORMATION AND HYDROGENATION

(71) Applicant: YEDA RESEARCH AND DEVELOPMENT CO. LTD., Rehovot (IL)

(72) Inventors: David Milstein, Rehovot (IL); Peng Hu, Rehovot (IL); Eran Fogler, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 15/508,117

(22) PCT Filed: Sep. 3, 2015

(86) PCT No.: PCT/IL2015/050888
§ 371 (c)(1),
(2) Date: Mar. 2, 2017

(87) PCT Pub. No.: WO2016/035081
PCT Pub. Date: Mar. 10, 2016

(65) Prior Publication Data
US 2017/0283257 A1 Oct. 5, 2017

(30) Foreign Application Priority Data
Sep. 4, 2014 (IL) .......................................... 234479

(51) Int. Cl.
*C01B 3/00* (2006.01)
*C07C 29/149* (2006.01)
(Continued)

(52) U.S. Cl.
CPC .......... *C01B 3/0015* (2013.01); *C07C 29/149* (2013.01); *C07C 209/50* (2013.01);
(Continued)

(58) Field of Classification Search
CPC ....... C01B 3/0015; C01B 3/00; C07C 211/10; C07C 233/36; C07C 237/08;
(Continued)

(56) References Cited

U.S. PATENT DOCUMENTS 4,356,321 A   10/1982  Hannam
4,788,289 A   11/1988  Su et al.
(Continued)

FOREIGN PATENT DOCUMENTS

CN   1569813 A   1/2005
CN   1820850 A   8/2006
(Continued)

OTHER PUBLICATIONS

Taube et al. "A System of Hydrogen-Powered Vehicles With Liquid Organic Hydrides" 1983, Int. J. Hydrogen Energy, vol. 8, No. 3, pp. 213-225 (Year: 1983).*
(Continued)

*Primary Examiner* — Amber R Orlando
*Assistant Examiner* — Syed T Iqbal
(74) *Attorney, Agent, or Firm* — Mark S. Cohen; Pearl Cohen; Zedek Latzer Baratz LLP

(57) ABSTRACT

The present invention provides a system and method of storing hydrogen ($H_2$) and releasing it on demand, comprising and making use of diaminoalkanes and alcohols, or aminoalcohols as liquid-organic hydrogen carrier systems (LOHC). 2-amino-ethanol (AE) or its N-methyl derivative 2-(methylamino)ethanol undergo catalytic dehydrogenation to form a cyclic dipeptide (glycine anhydride—GA) or its N,N-dimethyl derivative (N,N-dimethyl GA) with release of
(Continued)

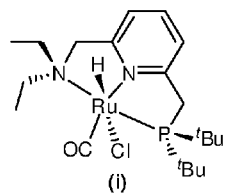

(i)

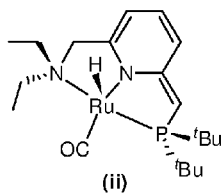

(ii)

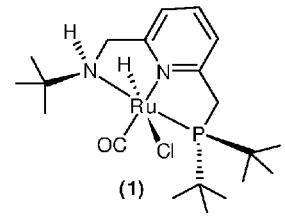

(1)

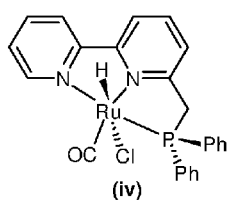

(iv)

(iii)

(vi)

hydrogen. Similarly, ethylenediamine (ED) and ethanol undergo catalytic dehydrogenation to form N,N'-diacetylethylenediamine (DAE) with release of hydrogen. Glycine anhydride (GA) or N,N-dimethyl-GA may be hydrogenated back to 2-aminoethanol (AE) or 2-(methylamino)ethanol, respectively, each of which functions as a hydrogen storage system. N,N'-diacetylethylenediamine (DAE) may be hydrogenated back to ED and ethanol, which functions as a hydrogen storage system. These reactions may be catalyzed by a variety of compounds or complexes, including Ruthenium complexes as described herein.

26 Claims, 10 Drawing Sheets

(51) Int. Cl.

| | |
|---|---|
| C07C 213/00 | (2006.01) |
| C07D 241/08 | (2006.01) |
| C07C 231/08 | (2006.01) |
| C07C 231/10 | (2006.01) |
| C07C 249/02 | (2006.01) |
| C07C 209/50 | (2006.01) |
| C07C 211/10 | (2006.01) |
| C07C 233/36 | (2006.01) |
| C07C 237/08 | (2006.01) |
| C07C 251/08 | (2006.01) |
| C07C 211/00 | (2006.01) |
| C07C 215/08 | (2006.01) |

(52) U.S. Cl.
CPC .......... *C07C 211/10* (2013.01); *C07C 213/00* (2013.01); *C07C 231/08* (2013.01); *C07C 231/10* (2013.01); *C07C 233/36* (2013.01); *C07C 237/08* (2013.01); *C07C 249/02* (2013.01); *C07C 251/08* (2013.01); *C07D 241/08* (2013.01); *C01B 3/00* (2013.01); *C07C 211/00* (2013.01); *C07C 215/08* (2013.01); *Y02E 60/327* (2013.01); *Y02E 60/328* (2013.01)

(58) Field of Classification Search
CPC ... C07C 251/08; C07C 209/50; C07C 231/08; C07C 231/10; C07C 249/02; C07C 29/149; C07C 213/00; C07C 211/00; C07C 215/08; C07D 241/08; Y02E 60/327; Y02E 60/328
See application file for complete search history.

(56) References Cited

U.S. PATENT DOCUMENTS

| | | | |
|---|---|---|---|
| 4,855,431 A | | 8/1989 | Chang et al. |
| 6,074,447 A | * | 6/2000 | Jensen ............... B01J 3/008 |
| | | | 423/658.2 |
| 7,709,689 B2 | | 5/2010 | Kilner et al. |
| 8,178,723 B2 | * | 5/2012 | Milstein ............... C07C 231/00 |
| | | | 546/2 |
| 9,738,685 B2 | | 8/2017 | Milstein et al. |
| 2005/0274440 A1 | * | 12/2005 | Tomiyama ............... C06D 5/06 |
| | | | 149/45 |
| 2009/0112005 A1 | | 4/2009 | Milstein et al. |
| 2011/0042227 A1 | | 2/2011 | Corbea et al. |
| 2012/0253042 A1 | | 10/2012 | Milstein et al. |
| 2014/0134100 A1 | | 5/2014 | Naeemi et al. |

FOREIGN PATENT DOCUMENTS

| | | | |
|---|---|---|---|
| CN | 1850330 | A | 10/2006 |
| CN | 101587779 | A | 11/2009 |
| CN | 101602015 | A | 12/2009 |
| CN | 101961661 | A | 2/2011 |
| CN | 102010447 | A | 4/2011 |
| CN | 102030657 | A | 4/2011 |
| CN | 102489315 | A | 6/2012 |
| CN | 102600888 | A | 7/2012 |
| CN | 202356105 | U | 8/2012 |
| CN | 102690162 | A | 9/2012 |
| CN | 103420796 | A | 12/2013 |
| CN | 103420797 | A | 12/2013 |
| EP | 0286280 | A1 | 10/1988 |
| EP | 1475349 | A2 | 11/2004 |
| EP | 2161251 | A1 | 3/2010 |
| JP | 2003146966 | A | 5/2003 |
| JP | 2004345964 | A | 12/2004 |
| JP | 2006063050 | A | 3/2006 |
| JP | 2008285454 | A | 11/2008 |
| JP | 2010063986 | A | 3/2010 |
| WO | WO 2003/093208 | A1 | 11/2003 |
| WO | WO 2008/035123 | A2 | 3/2008 |
| WO | WO 2010/018570 | A1 | 2/2010 |
| WO | WO 2012/052996 | A2 | 4/2012 |

OTHER PUBLICATIONS

Abbenhuis et al. "Ruthenium-Complex-Catalyzed N-(Cyclo) alkylation of Aromatic Amines with Diols. Selective Synthesis of N-(ω-Hydroxyalkyl) anilines of Type PhNH (CH2) n OH and of Some Bioactive Arylpiperazines" The Journal of Organic Chemistry. Jun. 26, 1998;63(13):4282-90.
Abdur-Rashid et al. "Catalytic Cycle for the asymmetric hydrogenation of prochiral ketones to chiral alcohols: Direct hydride and proton transfer from chiral catalysts trans-Ru (H) 2 (diphosphine)(diamine) to ketones and direct Addition of Dihydrogen to the Resulting Hydridoamido Complexes" Journal of the American Chemical Society. Aug. 1, 2001;123(30),7473-4.
Adair et al. "Oxidant-free oxidation: ruthenium catalysed dehydrogenation of alcohols" Tetrahedron letters. Nov. 21, 2005;46(47):8233-5.
Ahmad et al. "Triphenylphosphine Complexes of Transition Metals" Part III : Chapter Three, pp. 45-64 in "Inorganic Syntheses", John Wile & Sons, Inc.: 2007.
Albrecht et al. "Platinum group organometallics based on "pincer" complexes: sensors, switches, and catalysts" Angewandte Chemie International Edition. Oct. 15, 2001;40(20):3750-81.
Balaraman et al. Unprecedented catalytic hydrogenation of urea derivatives to amines and methanol. Angewandte Chemie. Dec. 2, 2011;123(49):11906-9, and supporting information S11702/1-S11702/7.
Balaraman et al. "Direct hydrogenation of amides to alcohols and amines under mild conditions" Journal of the American Chemical Society. Nov. 4, 2010;132(47):16756-8.
Balaraman et al. "Direct synthesis of secondary amines from alcohols and ammonia catalyzed by a ruthenium pincer complex" Catalysis Letters. Jan. 1, 2015:145(1):139-44.
Balaraman et al. "Efficient hydrogenation of organic carbonates, carbamates and formates indicates alternative routes to methanol based on CO2 and CO" Nature chemistry. Aug. 1, 2011;3(8):609-14.
Balaraman et al. "Efficient hydrogenation of biomass-derived cyclic di-esters to 1, 2-diols" Chemical Communications. 2012;48(8):1111-3.
Barrios-Francisco et al. "PNN ruthenium pincer complexes based on phosphinated 2, 2'-dipyridinemethane and 2,2'-oxobispyridine metal-ligand cooperation in cyclometalation and catalysis" Organometallics. May 13, 2013:32(10):2973-82.
Beamson et al. "Selective hydrogenation of amides using Rh/Mo catalysts" Journal of Catalysis. Jan. 1, 2010;269(1):93-102.
Beamson et al. "Selective hydrogenation of amides using ruthenium/molybdenum catalysts" Advanced Synthesis & Catalysis, Mar. 22, 2010;352(5):869-83.
Ben-Ari et al. "Metal-Ligand Cooperation in C—H and H2 Activation by an Electron-Rich PNP Ir (I) System: Facile Ligand

(56) References Cited

OTHER PUBLICATIONS

Dearomatization-Aromalization as Key Steps" Journal of the American Chemical Society. Dec. 6, 2006:128(48)115390-1.
Benet-Buchholz et al. "Iron vs. ruthenium—A comparison of the stereoselectivity in catalytic olefin epoxiclation" Dalton Transactions. 2009(30):5910-23.
Benet-Buchholz et al. "The Ru IV [double bond, length as m-dash] O-catalyzed sulfoxidation: a gated mechanism where O to S linkage isomerization switches between different efficiencies" Dalton Transactions, 2010;39(13):3315-20.
Blum et al. "Catalytically reactive ($\eta$4-tetracyclone)(CO) 2 (H) 2Ru and related complexes in dehydrogenation of alcohols to esters" Journal of organometallic chemistry. Feb. 26, 1985;282(1):C7-10.
Boelrijk et al. "Oxidation of octyl $\alpha$-D-glucopyranoside to octyl $\alpha$-D-glucuronic acid catalyzed by several ruthenium complexes, containing a 2-(phenyl) azopyridine or a 2-(nitrophenyl) azopyridine ligand" Journal of Molecular Catalysis A: Chemical. Oct. 28, 1995;103(2):73-85.
Bonnet et al. "Lanthanide mono (borohydride) complexes of diamide-diamine donor ligands: novel single site catalysts for the polymerisation of methyl methacrylate" Dalton Transactions. 2005(3):421-3.
Bray BL "Large-scale manufacture of peptide therapeutics by chemical synthesis" Nature Reviews Drug Discovery, Jul. 2003;2(7):587.
Bunton et al. "Source of catalysis of dephosphorylation of p-nitrophenyldiphenylphosphate by metallomicelles", J. Chem. Soc., Perkin Trans. 2, 1996, 419-425.
Cantillo D. "Mechanistic Insights on the Ruthenium-Catalyzed Hydrogenation of Amides—C—N vs. C—O Cleavage" European Journal of Inorganic Chemistry. Jul. 1, 2011;2011(19):3008-13.
Cassidy et al. "Practical synthesis of amides from in situ generated copper (I) acetylides and sulfonyl azides" Angew Chem Int Ed Engl. May 5, 2006;45(19):3154-7.
Catalano et al. "Steric modulation of electrocatalytic benzyl alcohol oxidation by [Ru (trpy)(R2dppi)(O)] 2+ complexes" Inorganic chemistry. May 4, 1998;37(9):2150-7.
Catalano et al. "Synthesis, characterization, and electrocatalytic oxidation of benzyl alcohol by a pair of geometric isomers of [Ru (trpy)(4, 4'-Me 2 dppi)(OH 2)] 2+ where 4, 4'-dppi is 3, 6-di-(4-methylpyrid-2-yl) pyridazine" 8059 Polyhedron, May 15, 2000;19(9):1049-55.
Chaignaud et al. "New highlights in the synthesis and reactivity of 1, 4-dihydropyrazine derivatives" Tetrahedron. Aug. 25, 2008;64(35):8059-66.
Chan et al. "Oxidative amide synthesis and N-terminal $\alpha$-amino group ligation of peptides in aqueous medium" Journal of the American Chemical Society. Nov. 22, 2006;128(46):14796-7.
Chanda et al. "Ruthenium monoterpyridine complexes incorporating $\alpha$, $\alpha$'-diimine based ancillary functions. Synthesis, crystal structure, spectroelectrochemical properties and catalytic aspect" Polyhedron. Sep. 1, 2002;21(20):2033-43.
Chardon-Noblat et al. "Electrosynthesis, physico-chemical and electrocatalytic properties of a novel electroactive Ru (0) material based on the (Ru (terpy)(CO)) frame (terpy=2, 2'; 6', 2"-terpyridine)" Journal of Electroanalytical Chemistry. Jul. 12, 2002;529(2):135-44.
Chatterjee et al. "Kinetics and catalysis of oxidation of phenol by ruthenium (IV)-oxo complex" Journal of Molecular Catalysis A: Chemical. Mar. 3, 2008;282(1-2):124-8.
Chatterjee et al. "Oxidation of catechol and I-ascorbic acid by [RuIII (tpy)(pic)(OH)]+(tpy=2, 2'6', 2"-terpyridine pic-=picolinate): Kinetic and mechanistic studies" Inorganic Chemistry Communications. Dec. 1, 2006;9(12):1219-22.
Chatterjee et al. "Synthesis, characterization and reactivity of a novel ruthenium (II) complex containing polypyridyl ligand" Polyhedron. Jan. 2, 2007;26(1):178-83.
Chen et al. Homogeneous photocatalytic oxidation of alcohols by a chromophore-catalyst dyad of ruthenium complexes. Angewandte Chemie, International Edition. Dec. 14, 2009;48(51): 9872-9875.

Cho et al. "Hydrogen sorption in HCl-treated polyaniline and polypyrrole: new potential hydrogen storage media" Fuel Chem. Div., 224th Nat. M. of the Am. Chem. Soc. Aug. 18, 2002;47:790-1.
Cho et al. "Copper-catalyzed hydrative amide synthesis with terminal alkyne, sulfonyl azide, and water" Journal of the American Chemical Society. Nov. 23, 2005;127(48):16046-7.
Claustro et al. "Synthesis, spectroscopic and electrochemical properties of ruthenium-2-(2'-hydroxyphenyl)-benzoxazole complexes. Crystal structure of [Ru (terpy)(HPB) CI]" Inorganica chimica acta. Jan. 10, 2003;342:29-36.
Cobley et al. "Platinum catalysed hydrolytic amidation of unactivated nitriles" Tetrahedron Letters. Apr. 1, 2000;41(14):2467-70.
Concepcion et al. "One site is enough. Catalytic water-oxidation by [Ru (tpy)(bpm)(OH2)] 2+ and [Ru (tpy)(bpz)(OH2)] 2+" Journal of the American Chemical Society. Nov. 14, 2008;130(49):16462-3.
Concepcion et al. "Catalytic and Surface-Electrocatalytic Water Oxidation by Redox Mediator-Catalyst Assemblies" Angewandte Chemie International Edition. Dec. 7, 2009;48(50):9473-6, and supporting informationS9473/1-59473/11.
Concepcion et al. "Catalytic water oxidation by single-site ruthenium catalysts" Inorganic chemistry. Jan. 8, 2010;4.9(4)1277-9.
Concepcion et al. "Mechanism of water oxidation by single-site ruthenium complex catalysts" Journal of the American Chemical Society. Jan. 19, 2010;132(5):1545-57.
Dakkach et al. "New Ru (II) complexes with anionic and neutral N-donor ligands as epoxidation catalysts: An evaluation of geometrical and electronic effects" Inorganic chemistry, Jul. 2, 2010;49(15):7072-9.
Das et al. "Zinc-catalyzed reduction of amides: unprecedented selectivity and functional group tolerance" Journal of the American Chemical Society. Jan. 27, 2010;132(5):1770-1.
Dick et al. "Novel bis ((trimethylsilyl) benzamidinato) titanium (III) complexes. Preparation and crystal structures of {PhC [(Me3Si) N] 2} 2Ti (. mu.-CI) 2Li (TMEDA),{PhC [(Me3Si) N] 2} 2Ti (BH4); and {PhC [(Me3Si) N] 2} 2Ti (. eta. 3-allyl)" Inorganic Chemistry. May 1993;32(10):1959-62.
Dobson et ai. "Complexes of the platinum metals. 7. Homogeneous ruthenium and osmium catalysts for the dehydrogenation of primary and secondary alcohols" Inorganic Chemistry. Jan. 1977;16(1):137-42.
Duan et al. "Isolated seven-coordinate Ru (IV) dimer complex with [HOHOH]-bridging ligand as an intermediate for catalytic water oxidation" Journal of the American Chemical Society. Jul. 14, 2009;131(30):10397-9.
Fernandes et al. "Reduction of amides with silanes catalyzed by MoO2CI2" Journal of Molecular Catalysis A: Chemical. Jul. 7, 2007;272(1-2):60-3.
Fogler et al. "System with Potential Dual Modes of Metal-Ligand Cooperation: Highly Catalytically Active Pyridine-Based PNNH—Ru Pincer Complexes" Chemistry—A European Journal. Nov. 24, 2014;20(48):15727-31.
Fogler et al. "New CNN-type ruthenium pincer NHC complexes. Mild, efficient catalytic hydrogenation of esters". Organometallics. Jun. 27, 2011;30(14):3826-33.
Francàs et al. "A Ru-Hbpp-Based Water-Oxidation Catalyst Anchored on Rutile TiO2" ChemSusChem. Apr. 20, 2009;2(4):321-9.
Fujita et al. "Synthesis of five-, six-, and seven-membered ring lactams by Cp* Rh complex-catalyzed oxidative N-heterocyclization of amino alcohols" Organic letters. Aug. 5, 2004:6(16):2785-8.
Ganaprakasam et al "Synthesis of peptides and pyrazines from $\beta$-amino alcohols through extrusion of H2 catalyzed by ruthenium pincer complexes: ligand-controlled selectivity" Angew Chem Int Ed Engl. Dec. 16, 2011;50(51)12240-4, and supporting information S12240/1-S12240/9.
Gargir et al. "PNS-Type ruthenium pincer complexes" Organometallics. Aug. 27, 2012;31(17):6207-14.
Ghosh et al. "Direct Amide Synthesis from Alcohols and Amines by Phosphine-Free Ruthenium Catalyst Systems" Advanced Synthesis & Catalysis. Nov. 1, 2009;351(16):2643-9.
Gibson et al. "Synthesis and characterization of ruthenium (II) hydrido and hydroxo complexes bearing the 2, 6-bis (di-Tert-butylphosphinomethyl) pyridine ligand" Organometallics, May 10, 2003;23(10):2510-3.

(56) References Cited

OTHER PUBLICATIONS

Gnanaprakasam et al. "Direct synthesis of imines from alcohols and amines with liberation of H2" Angewandte Chemie. Feb. 15, 2010;122(8):1510-3.

Gnanaprakasam et al. "Synthesis of amides from esters and amines with liberation of H2 under neutral conditions" Journal of the American Chemical Society. Jan. 19, 2011;133(6):1682-5.

Gnanaprakasam et al. "Direct Synthesis of Imines from Alcohols and Amines with Liberation of H2" Angewangte Chemie. Feb 15, 2010, 49(8):1468-1471.

Gnanaprakasam et al. "Ruthenium Pincer-Catalyzed Acylation of Alcohols Using Esters with Liberation of Hydrogen under Neutral Conditions" Advanced Synthesis & Catalysis. Dec. 17, 2010;352(15):3169-73.

Gnanaprakasam et al. "Synthesis of Peptides and Pyrazines from β-Amino Alcohols through Extrusion of H2 Catalyzed by Ruthenium Pincer Complexes: Ligand-Controlled Selectivity" Angewandte Chemie. Dec. 16, 2011;123(51):12448-52.

Gunanathan et al. Metal-ligand cooperation by aromatization-dearomatization: a new paradigm in bond activation and "Green" catalysis. Accounts of chemical research. Jul. 8, 2011;44(8);588-602.

Gunanathan et al. Direct synthesis of amides from aicohois and amines wlth liberation of H2. Science. Aug. 10, 2007;317(5839):790-2.

Gunanathan et al. "Selective synthesis of primary amines directly from alcohols and ammonia" Angewandte Chemie International Edition. Oct. 27, 2008:47(45):8661-4.

Gunanathan et al. "Bond activation by metal-ligand cooperation: Design of "green" catalytic reactions based on aromatization-dearomatization of pincer complexes" In Bifunctional Molecular Catalysis 2011 (pp. 55-84). Springer, Berlin, Heidelberg.

Gunanathan et al. "Direct conversion of alcohols to acetals and H2 catalyzed by an acridine-based ruthenium pincer complex" Journal of the American Chemical Society. Feb. 13, 2009;131(9)3146-7.

Gunanathan et al. "Reduction of Nitriles to Amines with H2 Catalyzed by Nonclassical Ruthenium Hydrides—Water-Promoted Selectivity for Primary Amines and Mechanistic Investigations" European Journal of Inorganic Chemistry. Aug. 1, 2011;2011(22):3381-6.

Guo et al. "Applications of ruthenium hydride borohydride complexes containing phosphinite and diamine ligands to asymmetric catalytic reations" Organic letters. Apr. 28, 2005;7(9):1757-9.

Hamid et al. "Ruthenium catalysed N-alkylation of amines with alcohols" Chemical Communications. 2007(7):725-7.

Hino et al. "Redox Behavior of New Ru-Dioxolene-Ammine Complexes and Catalytic Activity toward Electrochemical Oxidation of Alcohol under Mild Conditions" Chemistry letters, Nov. 13, 2004;33(12):1596-7.

Hirosawa et al. "Hydrogenation of amides by the use of bimetallic catalysts consisting of group 8 to 10, and group 6 or 7 metals" Sep. 9, 1996;37(37):6749-52.

Ho et al. "Double-helical ruthenium complexes of 2, 2': 6', 2", 2"':6"', 2ä-quinquepyridine (qpy) for multi-electron oxidation reactions" Chemical Communications. 1996(10):1197-8.

Hu et al. "A novel liquid organic hydrogen carrier system based on catalytic peptide formation and hydrogenation" Nature communications. Apr. 17, 2015; 6:6859; including Supplementary material.

Hu et al. "Rechargeable hydrogen storage system based on the dehydrogenative coupling of ethylenediamine with ethanol" Angewandte Chemie. Jan. 18, 2016;128(3):1073-6.

Huang et al. "A novel method to immobilize Ru nanoparticles on SBA-15 firmly by ionic liquid and hydrogenation of arene" Catalysis letters. Sep. 1, 2005;103(1-2):59-62.

Huff et al. "Cascade catalysis for the homogeneous hydrogenation of CO2 to methanol" Journal of the American Chemical Society. Oct. 26, 2011;133(45):18122-5.

International Search Report for PCT Application No. PCT/IL2015/050888 dated Dec. 16, 2015.

Ito et al. "Selective dimerization of aldehydes to esters catalyzed by hydridoruthenium complexes" Bulletin of the Chemical Society of Japan. Feb. 1982; 55(2):504-12.

Ito et al. "Hydrogenation of N-Acylcarbamates and N-Acylsulfonamides Catalyzed by a Bifunctional [Cp$^*$ Ru (PN)] Complex" Angewandte Chemie International Edition. Feb. 2, 2009;48(7):1324-7.

Jansen et al. "Synthesis of Hemilabile P, N Ligands: ω-2-Pyridyl-n-alkylphosphines" Monatshefte für Chemie/Chemical Monthly. Jun. 1, 1999;130(6):783-94.

Jensen et al. "Tansition metal tetrahydridoborates as models of methane activation: synthesis and structure of Ti (BH 4) 3 (PMe 3) 2" Journal of the Chemical Society, Chemical Communications. 1986(15):1160-2.

Jensen et al. "Titanium (III) tetrahydroborates. Preparation and crystal structure of Ti (BH4) 3 (PMe3) 2 containing an unusual Ti. cntdot . . . cntdot . . . cntdot. H. cntdot . . . cntdot . . . cntdot. B agostic interaction" Journal of the American Chemical Society. Jul. 1988;110(15):4977-82.

Jia et al. "Synthesis, Characterization, and Acidity Properties of [MCI (H2)(L)(PMP)] BF4 (M=Ru, L'PPh3, CO; M=Os, L=PPh3; PMP=2, 6-(Ph2PCH2) 2C5H3N)" Organometallics Sep. 2, 1997;16(18):3941-9.

Jung et al. "Dehydrogenation of alcohols and hydrogenation of aldehydes using homogeneous ruthenium catalysts" Organometallics. Apr. 1982;1(4):658-66.

Kaisheng et al. "Studies on Ruthenium Catalyst with a Ligand of Copolymer and Its Performance in Catalytic Hydrogenation" [J]. Chemistry. 2000;12:010. HCAPLUS Abstrict.

Kelson et al. "Synthesis and structure of a ruthenium (II) complex incorporating κ N bound 2-pyridonato ligands; a new catalytic system for transfer hydrogenation of ketones" Journal of the Chemical Society, Dalton Transactions. 2000(22):4023-4.

Kohl et al. "Consecutive thermal H2 and light-induced O2 evolution from water promoted by a metal complex" Science. Apr. 3, 2009;324(5923)74-7.

Langer et al. "Stepwise Metal-Ligand Cooperation by a Reversible Aromatization/Deconjugation Sequence in Ruthenium Complexes with a Tetradentate Phenanthroline-Based Ligand" Chemistry—A European Journal. Mar. 4, 2013;19(10):3407-14.

Langer et al. "Efficient hydrogenation of ketones catalyzed by an iron pincer complex" Angewandte Chemie. Feb. 25, 2011:123(9):2168-72.

Langer et a. "Low-Pressure Hydrogenation of Carbon Dioxide Catalyzed by an Iron Pincer Complex Exhibiting Noble Metal Activity" Angewandte Chemie International Edition. Oct. 10, 2011;50(42):9948-52.

Lee et al. "Hydroboration of alkenes and alkynes with sodium borohydride catalyzed by titanium complex" Chemistry Letters. Mar. 5, 1984;13(3):363-6.

Lee et al. "Regio-and stereo-selectivities in the titanium complex catalyzed hydroboration of carbon-carbon double bonds in various unsaturated compounds" Chemistry Letters. May 5, 1984;13(5):673-6.

Letts et al. "The synthesis, characterization, and reactivity of an unusual, amphoteric (tetrahydroborato) ruthenium hydride complex of a chelating triphosphine, Ru (H)(. eta. 2-BH4)(ttp)" Journal of the American Chemical Society. Jul. 1982;104(14):3898-905.

Liao et al. "Hydrophilicity modification of MCM-41 with zirconia and supported ruthenium-lanthanum for benzene hydrogenation to cyclohexene" Synthesis and Reactivity in Inorganic, Metal-Organic, and Nano-Metal Chemistry. Oct. 21, 2013;43(9):1206-11.

Liao et al. "Benzene hydrogenation over oxide-modified MCM-41 supported ruthenium-lanthanum catalyst: the influence of zirconia crystal form and surface hydrophilicity" Chemical Engineering Journal, May 1, 2014;243:207-16.

Ligthart et al. "Highly sustainable catalytic dehydrogenation of alcohols with evolution of hydrogen gas" Tetrahedron letters. Feb. 10, 2003;44(7):1507-9.

Lin et al. "A convenient lactonization of diols to γ-and δ-lactones catalysed by transition metal polyhydrides" Journal of organometallic chemistry. May 19, 1992;429(2)269-74.

(56) References Cited

OTHER PUBLICATIONS

Liu et al. "Synthesis of PVP-stabilized Pt/Ru colloidal nanoparticles by ethanol reduction and their catalytic properties for selective hydrogenation of ortho-chloronitrobenzene" Journal of catalysis. Feb. 14, 2011;278(1):1-7.

Llvanov et al. "Photocatalytic Splitting of CS2 to S8 and a Carbon-Sulfur Polymer Catalyzed by a Bimetallic Ruthenium (II) Compound with a Tertiary Amine Binding Site: Toward Photocatalytic Splitting of CO2?" Inorganic chemistry. Oct. 26, 2011;50(22):11273-5.

Magro et al. "The synthesis of amines by the homogeneous hydrogenation of secondary and primary amides" Chemical communications. 2007(30);3154-6.

Masaoka et al. "Clear evidence showing the robustness of a highly active oxygen-evolving mononuclear ruthenium complex with an aqua ligand" Chemistry letters. Feb. 5, 2009;38(2):182-3.

Menashe et al. "Catalytic disproportionation of aldehydes with ruthenium complexes" Organometallics. Nov. 1991;10(11):3885-91.

Miao et al. "Ru nanoparticles immobiliz.ed on montmorilionite by ionic liquids: a highly efficient heterogeneous catalyst for the hydrogenation of benzene" Angewandte Chemie International Edition. Jan. 1, 2006;45(2):266-9.

Milstein D. "Discovery of environmentally benign catalytic reactions of alcohols catalyzed by pyridine-based pincer Ru complexes, based on metal-ligand cooperation" Topics in Catalysis. Aug. 1, 2010;53(13-14):915-23.

Mola et al. "Ru-Hbpp-Based Water-Oxidation Catalysts Anchored on Conducting Solid Supports" Angewandte Chemie, International Edition, Jul. 21, 2008;47(31): 5830-5832.

Montag et al. "Exclusive C—C Oxidative Addition in a Rhodium Thiophosphoryl Pincer Complex and Computational Evidence for an η3-C—C—H Agostic Intermediate" Organometallics. Dec. 28, 2011,31(1):505-12.

Mulfort et al. "Supramolecular Cobaloxime Assemblies for H2 Photocatalysis: An Initial Solution State Structure-Function Analysis" The Journal of Physical Chemistry B. Jul. 1, 2010;114(45):14572-81.

Murahashi et al. "Ruthenium-catalyzed amidation of nitriles with amines. A novel, facile route to amides and polyamides" Journal of the American Chemical Society. Nov. 1986;108(24):7846-7.

Murahashi et al. "Ruthenium-catalyzed hydration of nitriles and transformation of. delta.-keto nitriles to ene-lactams" The Journal of Organic Chemistry. Apr. 1992;57(9)2521-3.

Muthusamy et a. "New approach to the synthesis of macrocyclic tetralactones via ring-closing metathesis using Grubbs' first-generation catalyst" The Journal of organic chemistry. Feb. 16, 2007;72(4):1495-8.

Naota et al. "Ruthenium-catalyzed transformations of amino alcohols to lactams" Synlett. 1991;1991(10):693-4.

Navarro et al. "Redox and spectral properties of [Ru (trpy) L (H2O)](ClO4) 2 [trpy=2, 2': 66"-terpyridine L=4, 4'-(OMe) 2bpy; 4, 4'-(NO2) 2bpy]: A comparative computational study" Polyhedron. May 1, 1996,15(9):1531-7.

Nordstrøm et al. "Amide synthesis from alcohols and amines by the extrusion of dihydrogen" Journal of the American Chemical Society, Dec. 5, 2008;130(52):17672-3.

Ohkuma et al, "Trans-RuH (η1-BH4)(binap)(1, 2-diamine): A Catalyst for asymmetric hydrogenation of simple ketones under base-Free conditions" Journal of the American Chemical Society, Jun. 12, 2002;124(23):6508-9.

Owston et al. "Iridium-catalyzed conversion of alcohols into amides via oximes" Organic letters. Jan. 4, 2007;9(1):73-5.

Pefkianakis et al. "End-functionalization of semiconducting species with dendronized terpyridine-Ru (II)-terpyridine complexes" Journal of Polymer Science Part A: Polymer Chemistry. Apr. 1, 2009;47(7):1939-52.

Pérez-Picaso et al. "Efficient microwave assisted syntheses of 2, 5-diketopiperazines in aqueous media" Molecules, Jul. 31, 2009;14(3):2836-49.

Pitet et al. "Sequential ROMP of cyclooctenes as a route to linear polyethylene block copolymers" Dalton transactions. 2013;42(25):9079-88.

Pramanik et al. "Chemical oxidation of water to dioxygen. Homogeneous catalysis by a ruthenium aquo-complex" Transition Metal Chemistry, Sep. 1, 1997;22(5):524-6.

Pramanik et al. "Chemistry of [Ru (tpy)(pap)(L') n+ (tpy=2, 2', 6', 2"-terpyridine; pap=2-(phenylazo) pyridine; L'=CI-, H 2 O, CH 3 CN, 4-picoline, N 3-; n=1, 2), X-ray crystal structure of [Ru (tpy)(pap)(CH 3 CN)](ClO 4) 2 and catalytic oxidation of water to dioxygen by [Ru (tpy)(pap)(H 2 O)] 2+" Polyhedron. Dec. 31, 1998;17(9):1525-34.

Prechtl et al. "Direct c:oupling of alcohols to form esters and amides with evolution of H 2 using in situ formed ruthenium catalysts" Catalysis Science & Technology. 2012;2(10):2039-42.

Ramos et al, "Eletlrocatalysis of CO2 reduction in aqueous media at electrodes modified with eiectropolymerized films of vinylterpyridine complexes of transition metals" Inorganic Chemistry, Jun. 1995;34(12):3339-48.

Rannard et al. "The selective reaction of primary amines with carbonyl imidazole containing compounds: selective amide and carbamate synthesis" Organic letters, Jul. 13, 2000;2(14)2117-20.

Sala et al. "The Spectroscopic, Eiectrochemical and Structural Characterization of a Family of Ru Complexes Containing the C2-Symmetric Didentate Chiral 1, 3-Oxazoline Ligand and Their Catalytic Activity" European Journal of Inorganic Chemistry. Nov. 1, 2007;2007(33):5207-14.

Sandoval et al. "Mechanism of Asymmetric Hydrogenation of Ketones Catalyzed by BINAP/1, 2-Diamine-Ruthenium (II) Complexes" Journal of the American Chemical Society. Nov. 5, 2003;125(44):13490-503.

Schwalbe et al. "Ruthenium polypridine complexes of tris-(2-pyridyl)-1, 3, 5-triazine—unusual building blocks for the synthesis of photochemical molecular devices" Dalton Transacations. 2009(20):4012-22.

Seckin et al. "Preparation and catalytic properties of a Ru (II) coordinated polyimide supported by a ligand containing terpyridine units" Journal of Inorganic and Organometallic Polymers and Materials. Jun. 1, 2009;19(2):143-51.

Sens et al. "Synthesis, Structure, and Acid-Base and Redox Properties of a Family of New Ru (II) Isomeric Complexes Containing the Trpy and the Dinucleating Hbpp Ligands" Inorganic chemistry. Dec. 15, 2003;42(25):8385-94.

Sens et al. "A new Ru complex capable of catalytically oxidizing water to moiecular dioxygen" Journal of the American Chemical Society. Jun. 30, 2004;126(25):7798-9.

Seok et al. "The comparative study in the oxygen atom transfer reaction by ruthenium mono-oxo complexes" Bulletin of the Korean Chemical Society. 1998;19(10):1084-90.

Serrano et al. "Synthesis, structure, redox properties, and catalytic activity of new ruthenium complexes containing neutral or anionic and facial or meridional ligands: An evaluation of electronic and geometrical effects" Inorganic chemistry. Jun. 25, 2007;46(13):5381-9.

Shimizu et al. "Direct Dehydrogenative Amide Synthesis from Alcohols and Amines Catalyzed by γ-Alumina Supported Silver Cluster" Chemistry—A European Journal. Oct. 5, 2009;15(39):9977-80.

Smith et al. "Efficient Synthesis of Halomethyl-2, 2'-Bipyridines: 4, 4'-Bis (Chloromethyl)-2, 2'-Bipyridine" Organic syntheses. Apr. 28, 2003:78:82.

Spasyuk et al. "From esters to alcohols and back with ruthenium and osmium catalysts", Angew Chem Int Ed Engl. Mar. 12, 2012;51(11):2772-5.

Srimani et al. "Catalytic coupling of nitriles with amines to selectively form imines under mild hydrogen pressure" Chemical Communications. 2012;48(97):11853-5.

Srimiani et al. "Formation of Tediary Amides and Dihydrogen by Dehydrogenative Coupling of Primary Alcohols with Secondary Amines Catalyzed by Ruthenium Bipyridine-Based Pincer Complexes" Advanced Synthesis & Catalysis. Sep. 16, 2013;355(13):2525-30.

(56) References Cited

OTHER PUBLICATIONS

Statler et al. "Alkyl, hydrido-, and related compounds of ruthenium (II) with trimethylphosphine. X-Ray crystal structures of hydrido (tetrahydroborato-HH') tris (trimethylphosphine) ruthenium (II), tri-μ-chloro-bis [tris (trimethylphosohine) ruthenium (II)] tetrafluoroborate, and bis [cis-methyltetrakis (trimethylphosphine) ruthenio] mercury (II)-tetrahydrofuran (1/1)" Journal of the Chemical Society, Dalton Transactions. 1984(8):1731-8.

Sussuchi et al. "Effect of the cis-and trans-[1, 2-bis (diphenylphosphino) ethylene] ligands in the properties of diphosphine-polypyridyl complexes of ruthenium (II): Application to electrocatalytic oxidations of organic compounds" Journal of Molecular Catalysis A: Chemical. Nov. 15, 2006;259(1-2):302-8.

Sussuchi et al. "Synthesis and eiectrochemical, spectral and catalytic properties of diphosphine-polypyridyl ruthenium complexes" Polyhedron, Apr. 17, 2006;25(6):1457-63.

Swamy et al. "Mitsunobu and related reactions: advances and applications" Chemical reviews. Apr. 21, 2009;109(6)2551-651.

Taher et al. "Acid-, Water-and High-Temperature-Stable Ruthenium Complexes for the Total Catalytic Deoxygenation of Glycerol to Propane" Chemistry—A European Journal, Oct. 5, 2009;15(39):10132-43, and supporting information S10132/1-S10132/26.

Tamaru et al. "Direct oxidative transformation of aldehydes to amides by palladium catalysis" Synthesis. 1083;1983(06):474-6.

Tan et al. "Highly efficient tetradentate ruthenium catalyst for ester reduction: especially for hydrogenation of fatty add esters", Org Lett. Feb. 6, 2015;17(3):454-7.

Tanaka et al., (2008) Reversible conversion between chemical and electrical energies catalyzed by Ru complexes aimed to construct sustainable society Preprints of Symposia—American Chemical Society, Division of Fuel Chemistry 53(1): 236-237.

Telchmann et al. "Energy storage in residential and commercial buildings via Liquid Organic Hydrogen Carriers (LOHC)" Energy & Environmental Science. 2012;5(10):9044-54.

Tillack et al. "Catalytic amination of aldehydes to amides" European Journal of Organic Chemistry. Feb. 2001;2001(3):523-8.

Tillack et al. "A novel ruthenium-catalyzed amination of primary and secondary alcohols" Tetrahedron letters. Dec. 11, 2006;47(50):8881-5.

Tse et al. "Synthetic, spectral and catalytic activity studies of ruthenium bipyridine and terpyridine complexes: Implications in the mechanism of the ruthenium (pyridine-2, 6-bisoxazoline)(pyridine-2, 6-dicarboxylate)-catalyzed asymmetric epoxiciation of olefins utilizing H2O2" Journal of organometaliic chemistry. Oct. 15, 2006;691(21):4419-33.

Tseng et la. "Mononuclear ruthenium (II) complexes that catalyze water oxidation" Inorganic chemistry. Nov. 12, 2008;47(24):11763-73.

Van Der Boom et al. "Cyclometalated phosphine-based pincer complexes: mechanistic insight in catalysis, coordination, and bond activation" Chemical reviews. May 14, 2003;103(5).1759-92.

Vogt et al. "A New Mode of Activation of CO2 by Metal-Ligand Cooperation with Reversible C—C and M—O Bond Formation at Ambient Temperature" Chemistry—A European Journal, Jul. 23, 2012;18(30):9194-7.

Wada et al. "Electrochemical Oxidation of Water to Dioxygen Catalyzed by the Oxidized Form of the Bis (ruthenium-hydroxo) Complex in H2O" Angewandte Chemie International Edition. Apr. 17, 2000;39(8);1479-82.

Wada et al. "Syntheses and redox properties of bis (hydroxoruthenium) complexes with quinone and bipyridine ligands. Water-oxidation catalysis" Inorganic chemistry. Jan. 15, 2001,40(2):329-37.

Wasylenko et al. "Examination of water oxidation by catalysts containing cofacial metal sites" European Journal of Inorganic Chemistry. Jul. 1, 2010;2010(20):3135-42.

Wasylenko et al. "Insight into water oxidation by mononuclear polypyridyl Ru catalysts" Inorganic chemistry. Feb. 4, 2010;49(5):2202-9.

Watanabe et al. "Ruthenium-catalyzed N-alkylation and N-benzylation of amainoarenes with alcohols" The Journal of Organic Chemistry. Sep. 1984;49(18):3359-63.

Watson et al. "Ruthenium-catalyzed oxidation of alcohols into amides" Organic letters. May 15, 2009;11(12):2667-70.

Williams et al. "Variable NMR spin-lattice relaxation times in secondary amides: effect of Ramachandran angles on librational dynamics" The Journal of Physical Chemistry B. Aug. 6, 1998:102(32):6248-59.

Yamaguchi et al. "Syntheses of mixed-ligand ruthenium (II) complexes with a terpyridine or a tris (pyrazolyl) methane and a bidentate ligand: their application for catalytic hydroxylation of alkanes" Inorganic Chemistry Communications, Aug. 1, 1998;1(8):299-301.

Yeung et al. "Chiral C 1-symmetric 2, 2': 6', 2"-terpyridine ligands: Synthesis, characterization, cornplexation with copper (II), rhodium (III) and ruthenium (II) ions and use of the complexes in catalytic cyclopropanation of styrene" Polyhedron. Mar. 30, 2010;29(5):1497-507.

Yu et al. "Synthesis, redox properties and reactivities of ruthenium (II) complexes of 1, 1'-bisoquinoline (BIQN) and X-ray crystal structure of [Ru II (terpy)(BIQN)(CI)] CIO 4 (terpy=2, 2': 6', 2"-terpyridine)" Polyhedron. Nov. 30, 1994;13(21):2963-9.

Zeng at al. "Direct synthesis of polyamides via catalytic dehydrogenation of diols and diamines" Journal of the American Chemical Society. Jan. 4, 2011;133(5):1159-61.

Zhang et al. "Electron-rich, bulky ruthenium PNP-type complexes. Acceptorless catalytic alcohol dehydrogenation" Organometallics. Aug. 16, 2004;23(17):4026-33.

Zhang et al. "Efficient homogeneous catalytic hydrogenation of esters to alcohols" Angewandte Chemie. Feb. 6, 2006;118(7):1131-3.

Zhang et al. "Electron-rich, bulky PNN-type ruthenium complexes: synthesis, characterization and catalysis of alcohol dehydrogenation" Dalton Transactions. 2007(1):107-13.

Zhang et al. "Facile conversion of alcohols into esters and dihydrogen catalyzed by new ruthenium complexes" Journal of the American Chemical Society. Aug. 10, 2005;127(31):10840-1.

Zhang et al. "Electron-rich PNP-and PNN-type ruthenium (II) hydrido borohydride pincer complexes. Synthesis, structure, and catalytic dehydrogenation of alcohols and hydrogenation of esters" Organometallics. Oct. 18, 2011;30(210):5716-24.

Zhang et al. "Ru-TsDPEN with Formic Acid/Hünig's Base for Asymmetric Transfer Hydrogenation, a Practical Synthesis of Optically Enriched N-Propyl Pantolactam" The Journal of organic chemistry. Dec. 23, 2008;74(3):1411-4.

Zhang et al. "Efficient conversion D-glucose into D-sorbitol over MCM-41 supported Ru catalyst prepared by a formaldehyde reduction process" Carbonhydrate research. Aug. 16, 2011;346(11):1327-32.

Zhang et al. "Homogeneous catalytic synthesis of formic acid (salts) by hydrogenation of CO2 with H2 in the presence of ruthenium species" Journal of Molecular Catalysis A: Chemical. Oct. 10, 1996;112(1):9-14.

Zhang et al. "Theoretical studies on the electronic structures and spectroscopic properties for a series of Osmium (II)-2, 2',6', 2"-terpyridine complexes" Theoretical Chemistry Accounts. Oct. 1, 2008;121(3-4):123.

Zhang et al. "Structures and Spectroscopic Properties of [Ru (iph)(L) 2] 2+(L=cpy, mpy, npy) Complexes Containing Tetradentate Ligands" Acta Physico—Chimica Sinica. May 15, 2011;27(5):1089-94.

Zhao et al. "Acceptorless, neat, ruthenium-catalyzed dehydrogenative cyclization of diols to lactones" Organometallics. May 9, 2005;24(10):2441-6.

Zhao et al. "Monolithic Ru-based catalyst for selective hydrogenation of benzene to cyclohexene, Catalysis Communications" Mar. 1, 2008,9(3):459-64.

Zhao et al. "Selective hydrogenation of benzene to cyclohexene on a Ru/Al2O3/cordierite monolithic catalyst: Effect of mass transfer on the catalytic performance" Industrial & Engineering Chemistry Research. Jun. 17, 2008;47(14):4641-7.

(56) References Cited

OTHER PUBLICATIONS

Zhao et al. "Seiective hydrogenation of benzene to cyclohexene by a circulating method on monolithic catalyst Ru/Al2o3/Cordierite" Ranliao Huaxue Xuebao/Journal of Fuel Chemistry andTechnology. 2008 ;36(4):499-502.

Zhao et al. "Liquid-phase selective hydrogenation of benzene to cyclohexene on Ru/Al2O3—ZrO2/coordierite monoiithic catalysts" Journal of Molecular Catalysis A: Chemical. Aug. 18, 2009;309(1-2):35-9.

Zhao et al. "Preparation and Characterization of Ru/Al 2 O 3/Cordierite Monolithic Catalysts for Selective Hydrogenation of Benzene to Cyclohexene" Catalysis letters. Sep. 1, 2009;131(3-4):597-605.

Zhou et al. "Ruthenium (II) terpyridyl complexes exhibiting DNA photocleavage: the role of the substituent on monodentate ligand" The Journal of Physical Chemistry B. Jul. 14, 2009;113(33)11521-6.

Zhou et al. "Synthesis of an ionic Paramagnetic Ruthenium (III) Complex and Its Appiication as an Efficient and Recyclable Catalyst for the Transfer Hydrogenation of Ketones" European Journal of Inorganic Chemistry. Jul. 1, 2012;2012(21):3435-40.

Ziessel et al. "Co-ordinative properties of a hybrid phosphine—bipyridine ligand" Journal of the Chemical Society, Dalton Transactions. 1997(20):3777-84.

Zweifel et al. "Catalyzed dehydrogenative coupling of primary alcohols with water, methanol, or amines" Angewandte Chemie International Edition. Jan. 5, 2009:48(3);559-63.

\* cited by examiner

LIQUID-ORGANIC HYDROGEN CARRIER SYSTEMS BASED ON CATALYTIC PEPTIDE FORMATION AND HYDROGENATION

CROSS-REFERENCE TO RELATED APPLICATIONS

This application is a National Phase Application of PCT International Application No. PCT/IL2015/1050888, International Filing Date Sep. 3, 2015, claiming priority of Israel Patent Application No. 234479, filed Sep. 4, 2014, which are incorporated in their entirety herein by reference.

FIELD OF THE INVENTION

The present invention provides a system and method of storing hydrogen ($H_2$) and releasing it on demand, comprising and making use of aminoalcohol, or diaminoalkane and alcohol, as liquid-organic hydrogen carriers (LOHCs).

BACKGROUND OF THE INVENTION

After a century of intensive use of fossil fuels as the predominant energy source for driving high-tech civilization, these natural resources are running low and alternative fuels must be introduced in order to be able to maintain the fast development of human civilization. Furthermore, the ever-increasing consumption of fossil fuels pollutes the environment and there are claims it even contributes to global warming through the extensive production of greenhouse gases that block heat emission from our planet. It is therefore evident that real-life alternative energy sources must be developed in order to replace traditional ones. These should be inexpensive, safe, non-polluting and "user friendly" so as not to impede the development of dynamic human society.

Containing the highest energy density per unit mass and producing only water upon combustion, hydrogen is considered as one of the most efficient and environmentally friendly candidates as a future fuel. Hydrogen is a very energetic material compared to conventional fossil fuels and burns in air at a wide range of concentrations (5%-75%). Moreover, in contrast to fossil fuels, the combustion of hydrogen is considered free of pollution, as it generates only water as a by-product.

The concept of "Hydrogen Economy", involving the use of hydrogen as a general energy carrier, was suggested as early as 1972. However, hydrogen storage became one of the key points to access the attractive "hydrogen age" since then. The low energy density of heavy hydrogen tanks makes most commercial applications of hydrogen unfavorable. Thus, to achieve hydrogen economy, a major challenge is finding suitable hydrogen carriers. For decades, scientists have searched for suitable hydrogen storage materials. Inorganic or metal-organic systems, such as main-group hydrides, metal organic frameworks, metal clusters, and nanostructured materials, have been explored for this purpose. Unfortunately, all of these efforts suffer from significant limitations.

On the other hand, organic compounds received much less attention as hydrogen carriers, because reversible $H_2$ release under reasonable temperatures was not achieved until 2005. Recently, organic compounds, such as formic acid, methanol-water, formaldehyde-water and carbohydrates, were intensively studied as potential hydrogen storage materials. Among them, "liquid organic hydrogen carriers" (LOHC), which can be dehydrogenated and hydrogenated with considerable amounts of hydrogen and might be used for transportation, are of special interest. An attractive LOHC of potential commercial interest has been N-ethylcarbazole, which was first studied by Air Products and Chemicals. Hydrogenation of N-ethylcarbazole to perhydro-N-ethylcarbazole consumes 6 equivalents of $H_2$, resulting in hydrogen storage capacity of as high as 5.8 wt %. However, many disadvantages still exist in this system, including the requirement of high $H_2$ pressure for the hydrogenation step and high reaction temperature for the dehydrogenation step, and the need of different catalysts for these steps. Two other recent examples of LOHCs are 2-methyl-1,2,3,4-tetrahydroquinoline and 2,6-dimethyldecahydro-1,5-naphthyridine, which can be reversibly dehydrogenated to 2-methylquinoline and 2,6-dimethyl-1,5-naphthyridine, respectively, catalyzed by Ir complexes. However, these two systems suffer from high catalyst loading (5 mol %), relatively expensive liquids, and in the case of 2-methyl-1,2,3,4-tetrahydroquinoline, low hydrogen storage capacity.

The goal of the Fuel Cell Technologies Office (FCTO) of the United States is to provide adequate hydrogen storage for onboard light-duty vehicle, for material-handling equipment, and for portable power applications to meet the U.S. Department of Energy (DOE) hydrogen storage targets. By 2020, Fuel Cell Technologies Office (FCTO) of the United States aims to develop and verify onboard automotive hydrogen storage systems achieving targets that will allow hydrogen-fueled vehicle platforms to meet customer performance expectations for range, passenger and cargo space, refueling time, and overall vehicle performance Specific system targets include hydrogen storage capacity of 5.5 wt %.

The inventors of the present invention have previously reported that pyridine-based PNN and PNP ruthenium pincer complexes (i) to (iv) (FIG. 1) efficiently catalyze several C—O and C—N bond forming dehydrogenative coupling reactions, giving pure hydrogen as byproduct, and also catalyze the reverse hydrogenation reactions. For example, by employing the dearomatized PNN catalyst (ii), amides are produced directly from alcohols and amines, with liberation of $H_2$. Complex (ii) can be obtained in situ by deprotonation of complex (i) with a base. The reverse reaction, i.e. hydrogenation of amides to form alcohols and amines, was also achieved under mild hydrogen pressure, using the same catalyst (Scheme 1).

Scheme 1

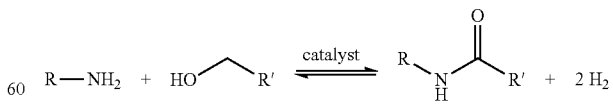

It was further reported that β-aminoalcohols can undergo dehydrogenative coupling to form cyclic dipeptides (diketopiperazines) (Scheme 2a) or oligopeptides (Scheme 2b), depending on the substituent R. Thus, in case of R=Me (2-aminopropan-1-ol), linear peptides were formed.

Scheme 2 Synthesis of (a) cyclic dipeptides and (b) oligopeptides from β-aminoalcohols

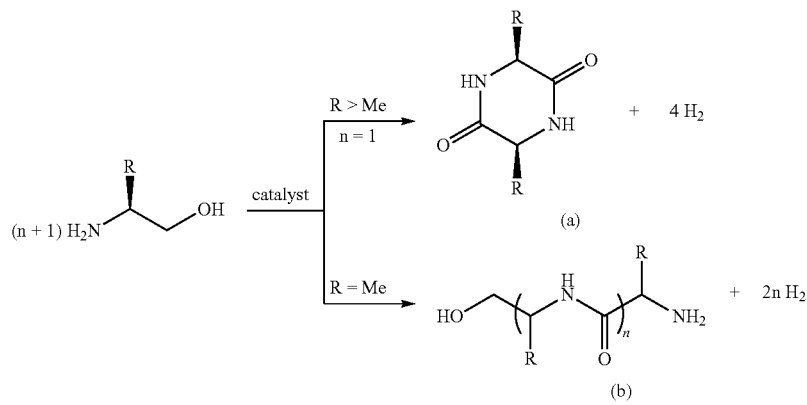

U.S. Pat. No. 8,178,723, describes methods for preparing amides, by reacting a primary amine and a primary alcohol in the presence of Ruthenium complexes, to generate the amide compound and molecular hydrogen.

U.S. Pat. No. 8,586,742, describes methods for preparing primary amines from alcohols and ammonia in the presence of Ruthenium complexes, to generate the amine and water.

PCT patent publication no. WO 2012/052996, to some of the inventors of the present application, describes methods of using Ruthenium complexes for (1) hydrogenation of amides to alcohols and amines; (2) preparing amides from alcohols and amines; (3) hydrogenation of esters to alcohols; (4) hydrogenation of organic carbonates to alcohols and hydrogenation of carbamates or urea derivatives to alcohols and amines; (5) dehydrogenative coupling of alcohols to esters; (6) dehydrogenation of secondary alcohols to ketones; (7) amidation of esters (i.e., synthesis of amides from esters and amines); (8) acylation of alcohols using esters; (9) coupling of alcohols with water to form carboxylic acids; and (10) dehydrogenation of beta-amino alcohols to form pyrazines.

Clearly, the development of inexpensive and abundant organic compounds with potentially high capacity to store and release hydrogen, ideally using the same catalyst for both loading and unloading hydrogen under relatively mild conditions, is a major challenge with no acceptable solutions known at this time.

SUMMARY OF THE INVENTION

The present invention provides a method and system for storing hydrogen ($H_2$) and releasing it on demand, based on the hydrogenation of amides and dehydrogenative coupling of amines and alcohols liquid-organic hydrogen carriers (LOHCs). More specifically, the invention relates to aminoalcohol LOHC and to diaminoalkane and alcohol LOHC. The process for hydrogen storage of this invention has a potential high hydrogen storage capacity.

1. Aminoalcohol LOHC

In one embodiment, the present invention provides a method and system for storing hydrogen ($H_2$) and releasing it on demand, based on the use of a 2-aminoethanol (AE) or its N-methyl derivative 2-(methylamino)ethanol liquid-organic hydrogen carrier (LOHC).

2-aminoethanol (AE) or 2-(methylamino)ethanol undergo catalytic dehydrogenation to form a cyclic dipeptide—glycine anhydride (GA) or its N,N-dimethyl derivative (N,N-dimethyl GA) with release of hydrogen. Glycine anhydride (GA) or N,N-dimethyl-GA may be hydrogenated back to 2-aminoethanol (AE) or 2-(methylamino)ethanol, respectively, each of which functions as a hydrogen storage system. Some linear peptides can also be formed in the process of 2-aminoethanol or 2-(methylamino)ethanol dehydrogenation, in addition to GA and N,N-dimethyl GA. The mixture of linear peptides and GA/N,N-dimethyl-GA are capable of being hydrogenated back to AE or its N-methyl derivative. These reactions may be catalyzed by a variety of catalytic systems, including transition metals and transition metal-based compounds and complexes, and combinations thereof. Examples of suitable catalysts are Ruthenium (Ru), iron (Fe), silver (Ag), gold (Au), and compounds and complexes containing these metals, among others.

As contemplated herein, a fundamentally new, reversible system that can load and unload $H_2$ with a potentially high hydrogen storage capacity has been developed. The system is based on a unique acceptorless dehydrogenative coupling process involving cheap and abundant 2-aminoethanol (AE) or its N-methyl derivative 2-(methylamino)ethanol, and hydrogenation of the product cyclic dipeptide glycine anhydride (GA) or N,N-dimethyl GA (N,N-dimethyl GA), which is possible with the same catalyst system. The success of this system highlights the possibilities of applying fundamentally new chemical reactions, such as reversible acceptorless peptide bond formation, as a basis for novel LOHCs.

As an amine and also an alcohol, one molecule of 2-aminoethanol or 2-(methylamino)ethanol releases two molecules of $H_2$ if piperazine-2,5-dione (glycine anhydride) or 1,4-dimethyl piperazine-2,5-dione (N,N-dimethyl GA) can be obtained by the intermolecular cyclic dehydrogenation reaction shown in Scheme 3. In this case, the maximal hydrogen storage capacity of the reaction presented in Scheme 3 using 2-aminoethanol is 6.56 wt %, and the maximal storage capacity of the reaction presented in Scheme 3 using 2-(methylamino)ethanol is 5.33 wt %, which is higher than other reported readily reversible LOHCs. In addition, since it is produced by industry in large amounts (for $CO_2$ scrubbing), 2-aminoethanol is very inexpensive and readily available. The reverse reaction, hydrogenation of GA or N,N-dimethyl GA, is conveniently conducted with the same catalyst system, and yields back the 2-aminoethanol or 2-(methylamino)ethanol reagents.

Scheme 3

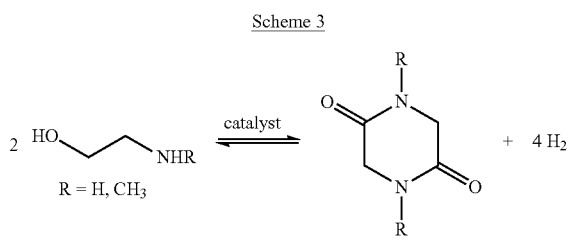

Hydrogen release may be desirable in a variety of applications and the present invention provides an efficient, low-cost and safe means to store hydrogen and release it on demand. The use of 2-aminoethanol or 2-(methylamino) ethanol for hydrogen storage and release had never been attempted. Based on prior knowledge, in the case of the structurally related alaninol, only linear peptides are formed (Scheme 2b, R=Me). Indeed, DFT calculations show that for 2-aminoethanol (AE), formation of linear peptides is thermodynamically more favorable than formation of diketopiperazine (glycine anhydride), although formation of the latter is also thermodynamically favorable [for reaction of Scheme 2a (R=H), the calculated Gibbs free energy is $\Delta G_{298}$=−6.08 kcal/mol. For reaction of Scheme 2b (R=H), $\Delta G_{298}$ is −10.17 kcal/mol (n=3); −18.18 kcal/mol (n=6); and −40.19 kcal/mol (n=11)]. However, formation of linear peptides as major products is less desirable since in that case the efficiency of 2-aminoethanol or 2-(methylamino)ethanol for hydrogen storage would be decreased, especially when short peptides are formed. Thus, production of glycine anhydride or N,N-dimethyl GA as the main product is beneficial for the hydrogen storage capacity. The present invention now provides for the first time an efficient process and system to achieve this object. In some embodiments, mixtures of GA/N,N-dimethyl GA and linear peptides can also be formed in the process of dehydrogenation of 2-aminoethanol or 2-(methylamino)ethanol. The mixture of linear peptides and GA/N,N-dimethyl GA are capable of being hydrogenated back to AE or 2-(methylamino)ethanol in accordance with the principles of the present invention.

Thus, in one embodiment, the present invention relates to the use of 2-aminoethanol (AE) or 2-(methylamino)ethanol as a liquid organic hydrogen carrier (LOHC) to store hydrogen ($H_2$) and release it on demand.

In another embodiment, the present invention relates to a process for the preparation of glycine anhydride (GA) or N,N-dimethyl GA in a yield of at least 30%, by dehyhdrogenative coupling of 2-aminoethanol (AE) or 2-(methylamino) ethanol, the process comprises the step of reacting 2-aminoethanol (AE) or 2-(methylamino) ethanol with a catalyst, thereby generating GA or N,N-dimethyl GA in a yield of at least 30%, and molecular hydrogen ($H_2$).

In another embodiment, the present invention relates to a process for the preparation of 2-aminoethanol (AE) or 2-(methylamino) ethanol, the process comprises the steps of reacting glycine anhydride (GA) or N,N-dimethyl GA with molecular hydrogen ($H_2$) in the presence of a catalyst, thereby generating 2-aminoethanol (AE) or 2-(methylamino) ethanol.

In another embodiment, the present invention relates to a process for the release hydrogen ($H_2$), the process comprises the step of reacting 2-aminoethanol (AE) or 2-(methylamino) ethanol with a catalyst, under conditions sufficient to release hydrogen, thereby generating glycine anhydride (GA) or N,N-dimethyl GA and molecular hydrogen ($H_2$).

In another embodiment, the present invention relates to a process for the storage of hydrogen, the process comprises the step of reacting glycine anhydride (GA) or N,N-dimethyl GA with molecular hydrogen ($H_2$) in the presence of a catalyst, under conditions sufficient to generate 2-aminoethanol (AE) or 2-(methylamino) ethanol as a hydrogen storage system.

In another embodiment, the present invention relates to a process for the storage and release of hydrogen ($H_2$) upon demand, comprising the steps of: (a) when hydrogen storage is desired, reacting glycine anhydride (GA) or N,N-dimethyl GA with molecular hydrogen ($H_2$) in the presence of a first catalyst, under conditions sufficient to generate 2-aminoethanol (AE) or 2-(methylamino) ethanol; and (b) when hydrogen release is desired, reacting 2-aminoethanol (AE) or 2-(methylamino) ethanol with a second catalyst, under conditions sufficient to generate glycine anhydride or N,N-dimethyl GA and hydrogen ($H_2$). The first and second catalyst may be the same or different. In another embodiment, the first and second catalysts are the same.

One embodiment of the aforementioned dehydrogenation process results in a mixture of (i) glycine anhydride or N,N-dimethyl GA; and (ii) a linear peptide represented by the structure:

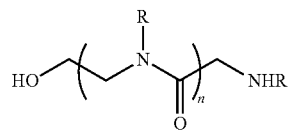

wherein R is H or $CH_3$, and n is an integer of 1-11. This mixture is capable of being hydrogenated back to 2-aminoethanol (AE) or 2-(methylamino) ethanol if desired. Thus, one embodiment of the hydrogenation process of the invention comprises reacting a mixture comprising (i) glycine anhydride (GA) or N,N-dimethyl GA; and (ii) a linear peptide as described above, so as to form 2-aminoethanol (AE) or 2-(methylamino) ethanol.

In another embodiment, the present invention relates to a system for the storage of hydrogen ($H_2$), the system comprising (i) glycine anhydride (GA) or N,N-dimethyl GA; and (ii) a catalyst, wherein the glycine anhydride or N,N-dimethyl GA is capable of reacting with molecular hydrogen ($H_2$) in the presence of the catalyst, under conditions sufficient to generate 2-aminoethanol (AE) or 2-(methylamino) ethanol as a hydrogen storage system.

In another embodiment, the present invention relates to a system for the release of hydrogen ($H_2$), the system comprising (i) 2-aminoethanol (AE) or 2-(methylamino) ethanol; and (ii) a catalyst, wherein the 2-aminoethanol or 2-(methylamino) ethanol is capable of being dehydrogenated in the presence of the catalyst, under conditions sufficient to generate glycine anhydride (GA) or N,N-dimethyl GA and molecular hydrogen.

In another embodiment, the present invention relates to a system for the storage and release of hydrogen ($H_2$) upon demand, the system comprising (i) glycine anhydride (GA) or N,N-dimethyl GA; (ii) 2-aminoethanol (AE) or 2-(methylamino)ethanol; and (iii) a first catalyst and a second catalyst, wherein the first catalyst is capable of reacting with glycine anhydride (GA) or N,N-dimethyl GA under conditions sufficient to store hydrogen, or the second catalyst is capable of reacting with 2-aminoethanol or 2-(methylamino) ethanol under conditions sufficient to release hydrogen, as desired, and wherein the first and second catalyst may be the same or different. In another embodiment, the first and second catalysts are the same.

As mentioned above, in some embodiments, the glycine anhydride (GA) or N,N-dimethyl GA is provided in admixture with linear peptide shown hereinabove. In accordance with this embodiment, the mixture is capable of being hydrogenated back to 2-aminoethanol (AE) or 2-(methylamino)ethanol upon demand.

In accordance with the principles of the present invention, any catalyst which can facilitate the hydrogenation and dehydrogenation processes described herein may be used in the context of the present invention. In some embodiments, the catalyst may be selected from the group consisting of a transition metal, a transition metal based compound, a transition metal based complex, compounds and complexes containing a multiplicity of transition metals, and any combination thereof. It is understood that the reaction may be catalyzed by transition metals or a combination of transition metals as well as compounds and complexes containing same, and any combination thereof.

In one currently preferred embodiment, the catalyst is a Ruthenium based complex. In some embodiments, the catalyst is a Ruthenium complex represented by the structure of any of formulae A1, A2 and A3, examples of which include a Ruthenium complex of formula (i) or (ii), with each possibility representing a separate embodiment of the present invention. In another embodiment, the catalyst is a Ruthenium complex represented by the structure of any of formulae A1', A2' and A3', examples of which include a Ruthenium complex of formula (iii), (iv), (v) and (vi), with each possibility representing a separate embodiment of the present invention. In another embodiment, the catalyst is a Ruthenium complex represented by the structure of any of formulae A1", A2" and A3", examples of which include a Ruthenium complex of formula (1), (2), (3) and (4), with each possibility representing a separate embodiment of the present invention. The structures of all of the aforementioned complexes are provided in the detailed description hereinbelow.

In some embodiments, the catalyst is further attached through any available positions to a solid support, or wherein the catalyst is embedded in a solid support, or is located on the surface of a solid support. The solid support may be selected from the group consisting of an organic solid support and an inorganic solid support. In some embodiments, the solid support comprises an inorganic material selected from the group consisting of silica, alumina, magnesia, titania, zirconia, montmorillonite, phyllosilicate, zeolites, talc, clays, layered double hydroxides, apatites, and any combination thereof. In other embodiments, the solid support comprises an organic polymer selected from polystyrene, polyethylene, polypropylene, polyvinylchloride, polytetrafluoro ethylene, polyacrylic acid methylester, polymethacrylic acid methylester, polycarbonates, polyethylene glycol, polyethylene terephthalate, poly (organo)siloxanes, and combinations thereof.

2. Diamines and Alcohol LOHC

In one embodiment, the present invention provides a method and system for storing hydrogen ($H_2$) and releasing it on demand, based on the use of a diaminoalkane and alcohol liquid-organic hydrogen carrier (LOHC).

In one embodiment, the present invention provides a use of a mixture of diaminoalkane and alcohol as a liquid organic hydrogen carrier (LOHC) to store hydrogen ($H_2$) and release it on demand. In another embodiment, the diaminoalkane is ethylenediamine (ED), propylenediamine, propane-1,2-diamine, butane-2,3-diamine, propane-1,3-diamine, butane-1,3-diamine or any mixture thereof. In another embodiment, the alcohol is ethanol, methanol, propanol, isopropanol, butanol, pentanol, or any mixture thereof.

In one embodiment, the present invention provides a use of a mixture of ethylendiamine (ED) and ethanol as a liquid organic hydrogen carrier (LOHC) to store hydrogen ($H_2$) and release it on demand.

In one embodiment, the present invention provides a process and system of storing hydrogen ($H_2$) and releasing it on demand, comprising dehydrogenative coupling of diamines and alcohols to form the corresponding amides, and the hydrogenation of the resulting amides using the same catalytic system for both reactions.

Ethylenediamine (ED) and ethanol undergo catalytic dehydrogenative coupling to form a linear diamide—N,N'-diacetylethylenediamine (DAE) with release of hydrogen. N,N'-diacetylethylenediamine (DAE) may be hydrogenated back to ethylenediamine (ED) and ethanol, which functions as a hydrogen storage system or as LOHC. Side products are formed in the process of Ethylenediamine (ED) and ethanol dehydrogenative coupling, in addition to DAE (N-(2-aminoethyl)-acetamide (AEA), and N-ethylidenethane-1,2-diamine (EED)). The mixture of products (DAE, N-(2-aminoethyl)-acetamide (AEA), and N-ethylidenethane-1,2-diamine (EED)) are capable of being hydrogenated back to ED and ethanol. These reactions may be catalyzed by Ruthenium based complexes as described herein below. In one embodiment, the Ruthenium based catalyst is identical for both reactions.

By reacting three molecules: 1×diamine and 2×alcohol (i.e., ED and two ethanol molecules) four molecules of $H_2$ are released if the dehydrogenative coupling to form AEA is obtained as shown in Scheme 4. In this case, the maximal hydrogen storage capacity of this reaction is 5.3 wt %. In addition, both ED and ethanol are commercially available, inexpensive and readily available compounds. The reverse reaction, hydrogenation of AEA, is conveniently conducted with the same catalyst system, and yields back the ED and ethanol reagents.

Scheme 4

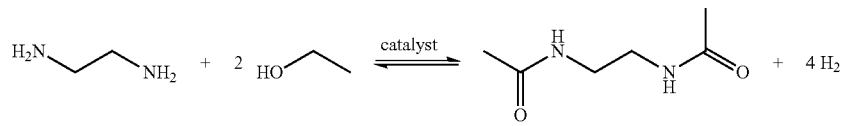

Hydrogen storage may be desirable in a variety of applications and the present invention provides an efficient, low-cost and safe means to store hydrogen and release it on demand.

In one embodiment, the LOHC system of this invention is based on the dehydrogenative coupling of ethylenediamine and ethanol, with a maximal hydrogen storage capacity (HSC) of 5.3 wt % (Scheme 4). The system is catalyzed by various ruthenium complexes (e.g., complex (iii) and (1) described hereinbelow) in the presence of catalytic base, using low catalyst loading (e.g., between 0.1 and 0.5 mol %), and exhibits excellent conversions for both the dehydrogenation and hydrogenation reactions.

This novel and simple hydrogen storage system is rechargeable and utilizes the same ruthenium pincer catalyst for both hydrogen storage and release procedures. Repetitive reversal reactions without addition of new catalyst result in excellent conversions in both the dehydrogenation and hydrogenation procedures at least in three cycles. Thus, in one embodiment, the present invention relates to a process for releasing hydrogen ($H_2$), said process comprises the step of reacting diaminoalkane with alcohol in the presence of a catalyst, under conditions sufficient to release hydrogen, thereby generating the corresponding diamidoalkane and hydrogen ($H_2$). In another embodiment, the diaminoalkane is ethylenediamine (ED) or 1,3-propylenediamine. In another embodiment, the alcohol is methanol, ethanol, or a mixture thereof.

In one embodiment, the present invention relates to a process for releasing hydrogen ($H_2$), said process comprises the step of reacting ethylenediamine (ED) and ethanol with a catalyst, under conditions sufficient to release hydrogen, thereby generating N,N'-diacetylethylenediamine (DAE) and molecular hydrogen ($H_2$).

In one embodiment, the present invention relates to a process for the storage of hydrogen, the process comprises the step of reacting N,N'-diacetylethylenediamine (DAE) with molecular hydrogen ($H_2$) in the presence of a catalyst, under conditions sufficient to generate ethylenediamine (ED) and ethanol as a hydrogen storage system or LOHC.

In one embodiment, the present invention relates to a process for the storage and releasing hydrogen ($H_2$) upon demand, comprising the steps of:
 (a) when hydrogen storage is desired, reacting N,N'-diacetylethylenediamine (DAE) with molecular hydrogen ($H_2$) in the presence of a first catalyst, under conditions sufficient to generate ethylenediamine (ED) and ethanol; and
 (b) when hydrogen release is desired, reacting ethylenediamine (ED) with ethanol in the presence of a second catalyst, under conditions sufficient to release hydrogen, thereby generating N,N'-diacetylethylenediamine (DAE) and molecular hydrogen ($H_2$), wherein the first catalyst and the second catalyst may be the same or different.

In another embodiment, the first and second catalysts are the same. In another embodiment, the reaction of ethylenediamine (ED) and ethanol further generates N-(2-aminoethyl)-acetamide (AEA); and/or N-ethylidenethane-1,2-diamine (EED), resulting in a mixture of DAE, AEA and EED, wherein said mixture is capable of being hydrogenated back to ED and ethanol if desired. In another embodiment, the reaction mixture of said reaction of N,N'-diacetylethylenediamine (DAE) with molecular hydrogen ($H_2$) further comprises N-(2-aminoethyl)-acetamide (AEA) and/or (iii) N-ethylidenethane-1,2-diamine (EED), so as to form ED and ethanol.

In one embodiment, the present invention relates to a system for the storage of hydrogen ($H_2$), the system comprises (i) N,N'-diacetylethylenediamine (DAE); and (ii) a catalyst, wherein said N,N'-diacetylethylenediamine (DAE) is capable of reacting with molecular hydrogen ($H_2$) in the presence of said catalyst, under conditions sufficient to generate ethylenediamine (ED) and ethanol as a hydrogen storage system.

In one embodiment, the present invention relates to a system for releasing hydrogen ($H_2$), the system comprises (i) diaminoalkane and alcohol; and (ii) a catalyst, wherein the diaminoalkane and alcohol are capable of being dehydrogenated in the presence of said catalyst, under conditions sufficient to generate the corresponding diamidoalkane and hydrogen.

In one embodiment, the present invention relates to a system for releasing hydrogen ($H_2$), the system comprises (i) ethylenediamine (ED) and ethanol; and (ii) a catalyst, wherein the ethylenediamine (ED) and ethanol are capable of being dehydrogenated in the presence of said catalyst, under conditions sufficient to generate N,N'-diacetylethylenediamine (DAE) and hydrogen.

In one embodiment, the present invention relates to a system for the storage and release of hydrogen ($H_2$) upon demand, the system comprises (i) N,N'-diacetylethylenediamine (DAE); (ii) ethylenediamine (ED) and ethanol; and (iii) a catalyst, wherein said catalyst is capable of reacting with DAE under conditions sufficient to store hydrogen, and wherein said catalyst is capable of reacting with ED and ethanol to release hydrogen, upon demand as desired.

In accordance with the principles of the present invention, any catalyst which can facilitate the hydrogenation and dehydrogenation processes described herein may be used in the context of the present invention. In some embodiments, the catalyst may be selected from the group consisting of a transition metal, a transition metal based compound, a transition metal based complex, compounds and complexes containing a multiplicity of transition metals, and any combination thereof. It is understood that the reaction may be catalyzed by transition metals or a combination of transition metals as well as compounds and complexes containing same, and any combination thereof.

In one currently preferred embodiment, the catalyst is a ruthenium complex. More preferable, the catalyst is a ruthenium complex represented by the structure of any of formulae A1, A2 and A3, examples of which include a Ruthenium complex of formula (i) or (ii), with each possibility representing a separate embodiment of the present invention. In another embodiment, the catalyst is a Ruthenium complex represented by the structure of any of formulae A1', A2' and A3', examples of which include a Ruthenium complex of formula (iii), (iv), (v) and (vi), with each possibility representing a separate embodiment of the present invention. In another embodiment, the catalyst is a Ruthenium complex represented by the structure of any of formulae A1", A2" and A3", examples of which include a Ruthenium complex of formula (1), (2), (3) and (4), with each possibility representing a separate embodiment of the present invention. The structures of all of the aforementioned complexes are provided in the detailed description hereinbelow.

In another embodiment, the catalyst is in an amount of between 0.1% and 1% (mol %) with respect to the substrate. In another embodiment, the catalyst is in an amount of 0.4% (mol %) with respect to the substrate.

In another embodiment, the process or the system according to this invention, further comprisese a solvent. In another embodiment, the solvent is selected from: benzene, toluene, o-, m- or p-xylene, mesitylene (1,3,5-trimethyl benzene), dioxane, THF, DME, DMSO, diglyme, DMF (dimethylformamide), valeronitrile, DMAC (dimethylacetamide), NMM (N-methylmorpholine), pyridine, n-BuCN, anisole, cyclohexane and mixtures thereof. In another embodiment, the solvent is dioxane, THF or mixture thereof.

In another embodiment, the process or the process or the system according to this invention, further comprises a catalytic amount of base. In another embodiment, the base is selected from: sodium hydroxide, potassium hydroxide, sodium methoxide, potassium methoxide, sodium ethoxide, potassium ethoxide, sodium propoxide, potassium propoxide, sodium butoxide, potassium butoxide, sodium t-butoxide, potassium t-butoxide, a metal bis(trimethylsilyl)amide salt (e.g., potassium bis(trimetylsilyl)amide (KHMDS)), sodium hydride, potassium hydride lithium diisopropylamide (LDA). In another embodiment, the base is potassium t-butoxide. In another embodiment, the catalytic amount of base is between 1-3 equivalents with respect to the catalyst.

The present invention will be understood and appreciated more fully from the following detailed description taken in conjunction with the appended figures:

DETAILED DESCRIPTION OF THE PRESENT INVENTION

Figure 1:
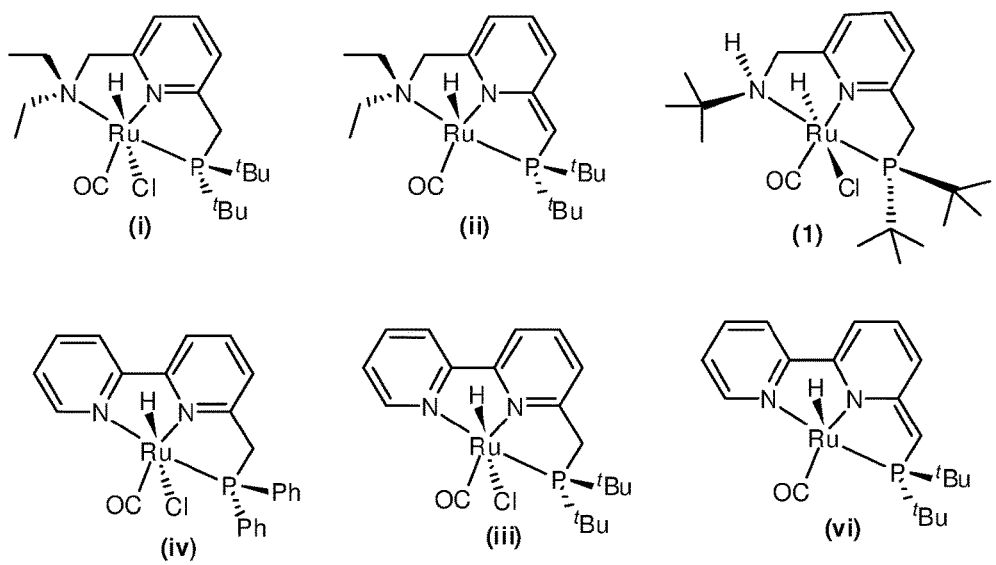
FIG. 1: Examples of Ru(II) pincer complexes used in hydrogenation/dehydrogenation processes of this invention.

This invention is directed to reversible methods and systems that store and release $H_2$ with a potentially high hydrogen storage capacity. The methods and systems are based on dehydrogenative coupling processes involving inexpensive and abundant diaminoalkanes and alcohols, or aminoalcohols, and hydrogenation of their corresponding amide products, which is possible with the same catalyst system and under mild conditions. The methods and system of this invention are compatible with the existing infrastructure and can be performed in large scales. The reactants used in the methods and system of this invention are inexpensive. For example, 2-aminoethanol is used in large amounts for $CO_2$ scrubbing from various gas streams in industrial plants.

In another embodiment, the alcohol is propanol. In another embodiment, the invention is directed to the use of ethylene diamine/ethanol liquid-organic hydrogen carrier system (LOHC). In another embodiment, the maximal hydrogen storage capacity (HSC) of this reaction is 5.3 wt %.

The success of this system highlights the possibilities of applying fundamentally new chemical reactions, such as reversible acceptorless peptide bond formation, as a basis for novel LOHCs.

The hydrogen storage capacity (HSC) is the percentage weight of $H_2$ produced relative to the weight of the reactants. This invention provides reversible methods and systems that store and release hydrogen with a potentially high hydrogen storage capacity of at least 5wt %. In one embodiment, the ethylenediamine and alcohol reaction to store hydrogen ($H_2$) and release it on demand has a maximal hydrogen storage capacity of 5.3 wt %. In one embodiment, the 2-ethanolamine reaction to store hydrogen ($H_2$) and release it on demand has a maximal hydrogen storage capacity of 6.56 wt %. In one embodiment, the 2-(methylamino)ethanol reaction to store hydrogen ($H_2$) and release it on demand has a maximal hydrogen storage capacity of 5.33 wt %.

1. Dehydrogenation and Hydrogenation Reactions using 2-aminoethanol (AE) and Glycine Anhydride (GA)

In one embodiment, the present invention relates to a process for the preparation of glycine anhydride (GA) by catalytic dehyhdrogenative coupling of 2-aminoethanol (AE), the process comprises the step of reacting 2-aminoethanol (AE) with a catalyst, thereby generating GA and molecular hydrogen ($H_2$). In another embodiment, the yield for the process is at least 30%, 35%, 40%, 45%, 50%, 55%, 60%, 65%, 70%, 75%, 80%, 85%, 90%, or 95%. Each possibility represents a separate embodiment of the present invention. In another embodiment, the present invention relates to a process for the preparation N,N-dimethyl GA (GA) by catalytic dehydrogenative coupling of 2-(methylamino)ethanol, the process comprises the step of reacting 2-(methylamino)ethanol with a catalyst, thereby generating N,N-dimethyl GA and molecular hydrogen ($H_2$). In another embodiment, the yield for the process is at least 30%, 35%, 40%, 45%, 50%, 55%, 60%, 65%, 70%, 75%, 80%, 85%, 90%, or 95%. Each possibility represents a separate embodiment of the present invention. Both these processes are described in Scheme 4a herein below. In one currently preferred embodiment, the catalyst is a transition metal, or a transition metal-containing compound or complex. In one particular embodiment, the transition metal catalyst is a Ruthenium complex as described herein. In another embodiment, the transition metal catalyst is complex 1 as described herein below. In another embodiment, the transition metal catalyst is complex i as described herein below.

These reactions, and examples for specific Ruthenium based complexes used therein as catalysts, are described in more detail the experimental section hereinbelow.

Some linear peptides can also be formed in the process of 2-aminoethanol or 2-(methylamino)ethanol dehydrogenation, in addition to GA and N,N-dimethyl GA. The mixture of linear peptides and GA/N,N-dimethyl-GA are capable of being hydrogenated back to AE or its N-methyl derivative, as illustrated in Scheme 5:

Scheme 5

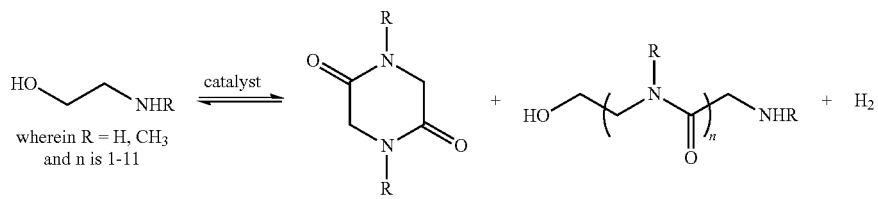

wherein R = H, CH$_3$
and n is 1-11

Scheme 4a

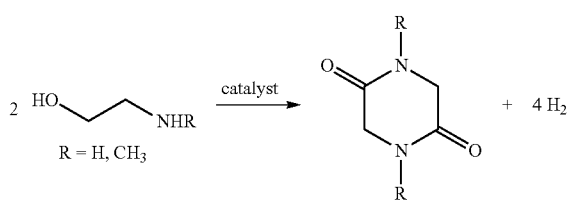

R = H, CH$_3$

In another embodiment, the present invention relates to a catalytic process for the preparation of 2-aminoethanol (AE), the process comprises the steps of reacting glycine anhydride (GA) with molecular hydrogen (H$_2$) in the presence of a catalyst, thereby generating 2-aminoethanol (AE). In another embodiment, the present invention relates to a catalytic process for the preparation of 2-(methylamino) ethanol, the process comprises the steps of reacting N,N-dimethyl glycine anhydride with molecular hydrogen (H$_2$) in the presence of a catalyst, thereby generating 2-(methylamino)ethanol. Both these reactions are described in Scheme 4b. In one currently preferred embodiment, the catalyst is a transition metal, or a transition metal-containing compound or complex. In one particular embodiment, the catalyst is a Ruthenium complex as described herein. In another embodiment, the transition metal catalyst is complex 1 as described herein below. In another embodiment, the transition metal catalyst is complex i as described herein below.

Scheme 4b

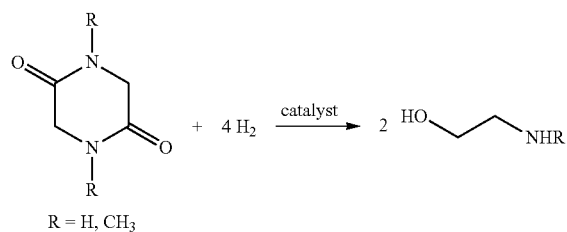

R = H, CH$_3$

In general, in all of the processes described herein, depending on the catalyst being used, the reaction permits the optional use of one or more equivalents of a base relative to the catalyst. The stoichiometric ratios of catalysts to base vary depending on the nature of the catalyst being used, as described below.

The stoichiometric ratios of reagents can vary, and depend on the particular catalyst being used, as well as solvent used for the reaction. In one embodiment, the amount of base used in the abovementioned processes is more than 1 equivalent, but less than 3 equivalents with respect to the catalyst. In another embodiment, the amount of base is 1 eq, 1.2 eq, 1.4 eq, 1.6 eq, 1.8 eq, 2 eq, 2.2 eq, 2.4 eq, 2.6 eq, 2.8 eq, 3 eq, 4 eq, 5, eq or 6 eq with respect to the catalyst. Each possibility represents a separate embodiment of the present invention. In one embodiment, the amount of base is 1.2 eq with respect to the catalyst. In one embodiment, the amount of base is 2.4 eq with respect to the catalyst.

Preferred bases for use in the processes of the reaction include amide salts, hydrides, hydroxides and alkoxides. Non-limiting examples of bases include sodium hydroxide, potassium hydroxide, sodium methoxide, potassium methoxide, sodium ethoxide, potassium ethoxide, sodium propoxide, potassium propoxide, sodium butoxide, potassium butoxide, sodium t-butoxide, potassium t-butoxide, a metal bis(trimethylsilyl)amide salt (e.g., potassium bis(trimetylsilyl)amide (KHMDS)), sodium hydride, potassium hydride lithium diisopropylamide (LDA), and the like. Each possibility represents a separate embodiment of the present invention. In one embodiment, the base is potassium t-butoxide (KO$^t$Bu).

In some embodiments, the process of any of the embodiments of the present invention as described herein is conducted under neat conditions in the absence of a solvent. In other embodiments, however, the process is conducted in the presence of an organic solvent such as, but not limited to benzene, toluene, o-, m- or p-xylene, mesitylene (1,3,5-trimethyl benzene), dioxane, THF, DME, DMSO, diglyme, DMF (dimethylformamide), valeronitrile, DMAC (dimethylacetamide), NMM (N-methylmorpholine), pyridine, n-BuCN, anisole and cyclohexane. Each possibility represents a separate embodiment of the present invention. In one embodiment, the solvent is dioxane. In another embodiment, the solvent is THF.

The reactions of the present invention can be performed for as long as needed so as to effect desired transformation, for example 1 hr to 24 hr or longer than 24 hr. In one embodiment, the reactions are performed for as long as 10 hrs, 12 hrs, 14 hrs, 16 hrs, 18 hrs, 20 hrs, 22 hrs, 24 hrs, 30 hrs, 48 hrs, 50 hrs, 60 hrs, or 72 hrs. Each possibility represents a separate embodiment of the present invention.

The temperature range can vary from room temperature to heated conditions, for example: up to 40° C., up to 60° C., up to 80° C., up to 100° C., up to 120° C., up to 140° C., up to 160° C., up to 180° C. or up to 200° C. Each possibility represents a separate embodiment of the present invention.

The mol % of the catalyst relative to the substrate can range between about 0.0001-10 mol %, preferably between about 0.1-1%, 0.05-0.8%, 0.1-0.6%, or 0.05-0.5%. Most preferably, between about 0.1-0.5%. Each possibility represents a separate embodiment of the present invention.

The yield of the hydrogenation and dehydrogenation reactions can very from 30% to 100%. In one embodiment, the yield of the dehydrogenation reaction (e.g., yield of GA) is at least 30%, 35%, 40%, 45%, 50%, 55%, 60%, 65%, 70%, 75%, 80%, 85%, 90%, 95% or 98%. Each possibility represents a separate embodiment of the present invention. In one embodiment, the yield of the hydrogenation reaction (e.g., yield of 2-aminoethanol) is at least 60%, 65%, 70%, 75%, 80%, 85%, 90%, 95%, 97%, 98%, or 99%. Each possibility represents a separate embodiment of the present invention.

The conversion level of the processes described herein above can vary between 70% and 100% based on the amount of the starting material (e.g., 2-aminoethanol). In one embodiment, the converion of the dehydrogenation reaction (e.g., of 2-aminoethanol) is at least 70%, 75%, 80%, 85%, 90%, 95% or 98%. In one embodiment, the converion of the hydrogenation reaction (e.g., of GA) is at least 70%, 75%, 80%, 85%, 90%, 95% or 98%. Each possibility represents a separate embodiment of the present invention.

In some embodiments the process is conducted under heat. In other embodiments, the process is conducted under inert gas. In other embodiments, the process is conducted under heat and under inert gas. However, the reactions of the invention can, when appropriate, also be conducted in the open air.

2. Dehydrogenation and Hydrogenation Reactions using ethylenediamine (ED) and ethanol; and N,N'-diacetylethylenediamine (DAE)

In one embodiment, the present invention relates to a process for the preparation of N,N'-diacetylethylenediamine (DAE) by catalytic dehyhdrogenative coupling of ethylenediamine (ED) and ethanol, the process comprises the step of reacting ethylenediamine (ED) with ethanol in the presence of a catalyst, thereby generating DAE and molecular hydrogen ($H_2$). The process is described in Scheme 4

Scheme 4

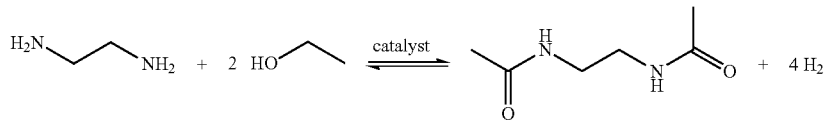

In one embodiment, the catalyst is a Ruthenium complex as described herein.

In another embodiment, the present invention relates to a catalytic process for the preparation of ethylenediamine (ED) and ethanol, the process comprises the steps of reacting N,N'-diacetylethylenediamine (DAE) with molecular hydrogen ($H_2$) in the presence of a catalyst, thereby generating ethylenediamine (ED) and ethanol. This reaction is described in Scheme 6. In one embodiment, the catalyst is a Ruthenium complex as described herein.

Scheme 6

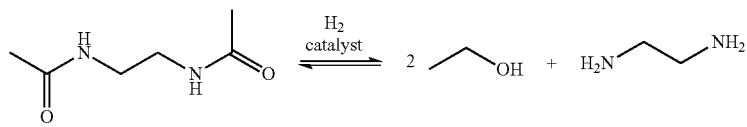

These reactions, and examples for specific Ruthenium based complexes used therein as catalysts, are described in more detail the experimental section hereinbelow.

The monoamide, N-(2-aminoethyl)-acetamide (AEA), and N-ethylidenethane-1,2-diamine (EED) side products, can also be formed in the process of ethylenediamine (ED)/ethanol dehydrogenation, in addition to N,N'-diacetylethylenediamine (DAE) (Scheme 7).

Scheme 7

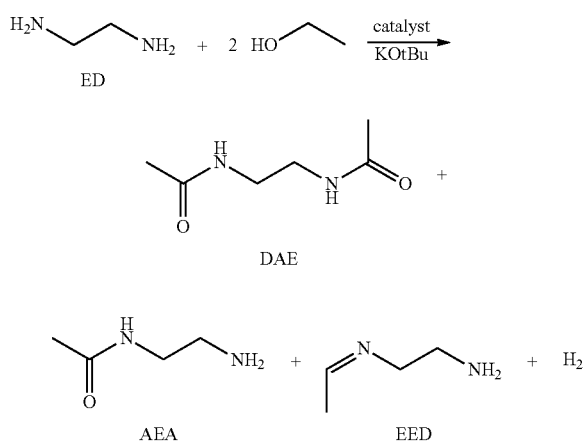

The mixture of products is capable of being hydrogenated back to ED and ethanol as illustrated in Scheme 8:

Scheme 8

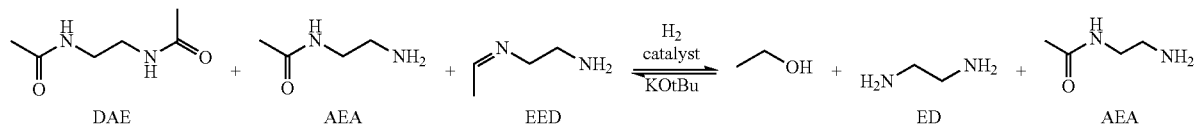

In general, in all of the processes described herein, depending on the catalyst being used, the reaction permits the optional use of one or more equivalents of a base relative to the catalyst. The stoichiometric ratios of catalysts to base vary depending on the nature of the catalyst being used, as described below.

The stoichiometric ratios of reagents can vary, and depend on the particular catalyst being used, as well as solvent used for the reaction. In one embodiment, the base is 1 eq, 1.2 eq, 1.4 eq, 1.6 eq, 1.8 eq, 2 eq, 2.2 eq, 2.4 eq, 2.6 eq, 2.8 eq, 3 eq, 4 eq, 5, eq or 6 eq with respect to the catalyst. Each possibility represents a separate embodiment of the present invention. In one embodiment, the base is 1.2 eq with respect to the catalyst. In one embodiment, the base is 2.4 eq with respect to the catalyst.

Preferred bases for use in the processes of the reaction include amide salts, hydrides, hydroxides and alkoxides. Non-limiting examples of bases include sodium hydroxide, potassium hydroxide, sodium methoxide, potassium methoxide, sodium ethoxide, potassium ethoxide, sodium propoxide, potassium propoxide, sodium butoxide, potassium butoxide, sodium t-butoxide, potassium t-butoxide, a metal bis(trimethylsilyl)amide salt (e.g., potassium bis(trimetylsilyl)amide (KHMDS)), sodium hydride, potassium hydride, lithium diisopropylamide (LDA), and the like. Each possibility represents a separate embodiment of the present invention. In one embodiment, the base is potassium t-butoxide (KO$^t$Bu).

In some embodiments, the process of any of the embodiments of the present invention as described herein is conducted under neat conditions in the absence of a solvent. In other embodiments, however, the process is conducted in the presence of an organic solvent such as, but not limited to benzene, toluene, o-, m- or p-xylene, mesitylene (1,3,5-trimethyl benzene), dioxane, THF, DME, DMSO, diglyme, DMF (dimethylformamide), valeronitrile, DMAC (dimethylacetamide), NMM (N-methylmorpholine), pyridine, n-BuCN, anisole and cyclohexane. Each possibility represents a separate embodiment of the present invention. In one embodiment, the solvent is dioxane. In another embodiment, the solvent is THF. In another embodiment, the solvent is one or more solvents selected from: benzene, toluene, o-, m- or p-xylene, mesitylene (1,3,5-trimethyl benzene), dioxane, THF, DME, DMSO, diglyme, DMF (dimethylformamide), valeronitrile, DMAC (dimethylacetamide), NMM (N-methylmorpholine), pyridine, n-BuCN, anisole and cyclohexane.

The reactions of the present invention can be performed for as long as needed so as to effect desired transformation, for example 1 hr to 24 hr or longer than 24 hr. In one embodiment, the reactions are performed for as long as 10 hr, 12 hrs, 14 hrs, 16 hrs, 18 hrs, 20 hrs, 22 hrs, 24 hrs, 30 hrs, 48 hrs, 50 hrs, 60 hrs, or 72 hrs. Each possibility represents a separate embodiment of the present invention. In another embodiment, for about 48 hr. In another embodiment, for about 24 hr. In another embodiment, for about 12 hr. In another embodiment, for about 10 hr.

The temperature range can vary from room temperature to heated conditions, for example: up to 40° C., up to 60° C., up to 80° C., up to 100° C., up to 120° C., up to 140° C., up to 160° C., up to 180° C. or up to 200° C. Each possibility represents a separate embodiment of the present invention. In another embodiment, between 70° C. and 200° C. In another embodiment, between 100° C. and 200° C. In another embodiment, between 70° C. and 150° C. In another embodiment, between 100° C. and 150° C. In another embodiment, between 100° C. and 120° C. In another embodiment, the temperature range depends on the boiling point of the solvent. In another embodiment, the temperature is the reflux temperature of the selected solvent. In another embodiment, the temperature is 115° C.

The mol % of the catalyst relative to the substrate can range between about 0.0001-10 mol %, preferably between about 0.01-1%, 0.05-0.8%, 0.1-0.6%, or 0.05-0.5%. Most preferably, between about 0.1-0.5%. Each possibility represents a separate embodiment of the present invention.

The yield of the hydrogenation and dehydrogenation reactions can very from 30% to 100%. In one embodiment, the yield of the dehydrogenation reaction (yield of DAE) is at least 25%, 30%, 35%, 40%, 45%, 50%, 55%, 60%, 65%, 70%, 75%, 80%, 85%, 90%, 95% or 98%. Each possibility represents a separate embodiment of the present invention. In one embodiment, the yield of the hydrogenation reaction (yield of ED) is at least 60%, 65%, 70%, 75%, 80%, 85%, 90%, 95%, 97%, 98%, or 99%. Each possibility represents a separate embodiment of the present invention. The conversion level of the processes described herein above can vary between 70% and 100% based on the amount of the starting material (e.g. ED or ethanol). In one embodiment, the converion of the dehydrogenation reaction (e.g., of ED and/or ethanol) is at least 25%, 30%, 35%, 40%, 45%, 50%, 55%, 60%, 65%, 70%, 75%, 80%, 85%, 90%, 95% 98% or 99%. In one embodiment, the converion of the hydrogenation reaction (e.g., of DAE) is at least 55%, 60%, 65%, 70%, 75%, 80%, 85%, 90%, 95%, 98% or 99%. Each possibility represents a separate embodiment of the present invention.

In some embodiments the process is conducted under heat. In other embodiments, the process is conducted under inert gas. In other embodiments, the process is conducted under heat and under inert gas. However, the reactions of the invention can, when appropriate, also be conducted in the open air.

3. Uses

Hydrogen storage is desirable in a variety of applications and the present invention provides an efficient, low-cost and safe means to store hydrogen and release it on demand. The dehydrogenation and hydrogenation reactions described herein provide a fundamentally new method for storing hydrogen ($H_2$) and releasing it on demand with a maximal high storage capacity of at least 5 wt %.

a. Diaminoalkane/Alcohol LOHC

In one embodiment, the invention is directed a method and system comprising and making use of diaminoalkane and alcohol liquid-organic hydrogen carrier (LOHC) to store hydrogen (H$_2$) and release it on demand Diaminoalkane and alcohol undergo catalytic dehydrogenation to form diamidoalkanes, with release of hydrogen. The diamidoalkanes may be hydrogenated back to diaminoalkane and alcohol, which function as a liquid-organic hydrogen carrier.

Thus, in one embodiment, the present invention relates to a process for the storage of hydrogen, the process comprises the step of reacting a diamidoalkane with molecular hydrogen (H$_2$) in the presence of a catalyst, under conditions sufficient to generate diaminoalkane and alcohol as a hydrogen storage system or as liquid-organic hydrogen carrier.

In accordance with this principle, another aspect of the present invention relates to a process for the storage and release of hydrogen (H$_2$), comprising the steps of:
(a) when hydrogen storage is desired, reacting diamidoalkane with molecular hydrogen (H$_2$) in the presence of a catalyst to generate diaminoalkane and alcohol; and
(b) when hydrogen release is desired, reacting diaminoalkane with alcohol in the presence of a catalyst, under conditions sufficient to generate diamidoalkane and hydrogen (H$_2$).

In another aspect, the present invention relates to system for the storage of hydrogen (H$_2$), the system comprising (i) diamidoalkane; and (ii) a catalyst, wherein the diamidoalkane react with molecular hydrogen (H$_2$) in the presence of the catalyst, under conditions sufficient to generate diaminoalkane and alcohol, as a hydrogen storage system.

In another aspect, the present invention relates to a system for releasing hydrogen (H$_2$), the system comprising (i) diaminoalkane and alcohol; and (ii) catalyst, wherein the diaminoalkane and alcohol are capable of being dehydrogenated in the presence of the catalyst, under conditions sufficient to generate diamidoalkane and molecular hydrogen.

The two systems may be combined so as to form one general system containing three components: (i) diamidoalkane; (ii) mixture of diaminoalkane and alcohol; and (iii) a catalyst, wherein the catalyst is reacted with either diamidoalkane or with diaminoalkane and alcohol under conditions sufficient to store or release hydrogen, upon demand and as desired. In each of the aforementioned reactions, the same catalytic system is used for the hydrogenation and dehydrogenation reactions. Alternatively, each of the reactions (i.e., hydrogenation and dehydrogenation) is performed with a different catalyst. In another embodiment, the hydrogenation reactions can be performed with a first catalyst, and the dehydrogenation reaction can be performed with a second catalyst, wherein the first and second catalyst are the same or different from each other. Each possibility represents a separate embodiment of the present invention. In a preferred embodiment, the first and the second catalysts are the same.

In some embodiments, mixtures of diamidoalkane and side products (e.g., mono-amidoalkane substituted with an amino moiety) are formed in the process of dehydrogenation of diaminoalkane and alcohol. The mixture of the diamidoalkane with its side products are capable of being hydrogenated back to diaminoalkane and alcohol in accordance with the principles of the present invention.

In one embodiment, for above mentioned diaminoalkane/alcohol based hydrogen storage and release processes and systems, the catalyst is preferably a ruthenium based complex. More preferably, the catalyst is a ruthenium based complex according to this invention as described hereinbelow. Most preferably, the catalyst is selected from compounds (i)-(vi) and (1)-(8). Each possibility represents a separate embodiment of the present invention. In one embodiment, the catalyst is compound iii. In one embodiment, the catalyst is compound 1.

In one embodiment, for above mentioned diaminoalkane/alcohol based hydrogen storage and release processes and systems, the diamidoalkane is selected from: N,N'-(ethane-1,2-diyl)diacetamide or N,N'-diacetylethylenediamide (DAE), N,N'-(propane-1,3-diyl)diacetamide, N,N'-(ethane-1,2-diyl)diformamide, N,N'-(propane-1,3-diyl)diacetamide, N,N'-(propane-1,3-diyl)diformamide, N,N'-(2-methylpropane-1,3-diyl)diacetamide, N,N'-(1-methylpropane-1,3-diyl)diacetamide, N,N'-(2-methylpropane-1,3-diformamide, and the like. Each possibility represents a separate embodiment of the present invention. In one embodiment, the diamidoalkane is N,N'-diacetylethylenediamide (DAE).

In one embodiment, for above mentioned diaminoalkane/alcohol based hydrogen storage and release processes and systems, the diaminoalkane is selected from: 1,2-ethylenediamine (ED), propylenediamine, propane-1,2-diamine, butane-2,3-diamine, propane-1,3-diamine, butane-1,3-diamine and the like. Each possibility represents a separate embodiment of the present invention. In one embodiment, the diaminoalkane is 1,2-ethylenediamine (ED).

In one embodiment, for above mentioned diaminoalkane/alcohol based hydrogen storage and release processes and systems, the alcohol is selected from: ethanol, methanol, propan-1-ol (n-propanol), propan-2-ol (isopropanol), n-butanol, pentanol, cyclohexanol, isobutyl-alcohol, tert-amyl-alcohol and the like. Each possibility represents a separate embodiment of the present invention. In one embodiment, the alcohol is a primary alcohol. In one embodiment, the alcohol is ethanol. In one embodiment, the alcohol is methanol.

b. Ethylenediamine/Alcohol LOHC System

In one embodiment, the invention is directed to a method and system for storing hydrogen and release it upon demand. In another embodiment, the method and system comprise and make use of ethylenediamine and alcohol liquid-organic hydrogen carrier system (LOHC) to store hydrogen (H$_2$) and release it on demand In another embodiment the alcohol is methanol. In another embodiment, the alcohol is ethanol. In another embodiment, the alcohol is propanol. In another embodiment, the invention is directed to the use of ethylene diamine/ethanol liquid-organic hydrogen carrier system (LOHC). In another embodiment, the maximal hydrogen storage capacity (HSC) of this reaction is 5.3 wt %.

Ethylenediamine (ED) and ethanol undergo catalytic dehydrogenation to form N,N'-diacetylethylenediamine (DAE), with release of hydrogen. The DAE may be hydrogenated back to ethylenediamine (ED) and ethanol, which function as a hydrogen storage system.

Thus, in one embodiment, the present invention relates to a process or method for the storage of hydrogen, the process or method comprises the step of reacting N,N'-diacetylethylenediamine (DAE) with molecular hydrogen (H$_2$) in the presence of a catalyst, under conditions sufficient to generate ethylenediamine (ED) and ethanol as a hydrogen storage system. The reaction, as well as the reverse reaction, dehydrogenation of ethylenediamine (ED) and ethanol, are described in Schemes 4, and 6-8 hereinabove.

In accordance with this principle, another aspect of the present invention relates to a process for the storage and release of hydrogen (H$_2$) upon demand, comprising the steps of:
(a) when hydrogen storage is desired, reacting N,N'-diacetylethylenediamine (DAE) with molecular hydrogen (H$_2$) in the presence of a catalyst to generate ethylenediamine (ED) and ethanol; and (b) when hydrogen release is desired, reacting ethylenediamine (ED) with ethanol in the presence of a catalyst, under conditions sufficient to generate N,N'-diacetylethylenediamine (DAE) and hydrogen ($H_2$).

In another aspect, the present invention relates to system for the storage of hydrogen ($H_2$), the system comprising (i) N,N'-diacetylethylenediamine (DAE); and (ii) a catalyst, wherein the DAE is capable of reacting with molecular hydrogen ($H_2$) in the presence of the catalyst, under conditions sufficient to generate ethylenediamine (ED) and ethanol, as a hydrogen storage system.

In another aspect, the present invention relates to a system for releasing hydrogen ($H_2$), the system comprising (i) ethylenediamine (ED) and ethanol; and (ii) catalyst, wherein the ethylenediamine (ED) and ethanol are capable of being dehydrogenated in the presence of the catalyst, under conditions sufficient to generate N,N'-diacetylethylenediamine (DAE), and molecular hydrogen.

Both systems may be combined so as to form one general system containing three components (i) N,N'-diacetylethylenediamine (DAE); (ii) ethylenediamine (ED) and ethanol; and (iii) a catalyst, wherein the catalyst is reacted with either N,N'-diacetylethylenediamine (DAE) or with ethylenediamine (ED) and ethanol under conditions sufficient to store or release hydrogen, as desired. In each of the aforementioned reactions, the same catalytic system can be used for the hydrogenation and dehydrogenation reactions. Alternatively, each of the reactions (i.e., hydrogenation and dehydrogenation) can be performed with different catalysts. In other words, the hydrogenation reactions can be performed with a first catalyst, and the dehydrogenation reaction can be performed with a second catalyst, wherein the first and second catalyst may be the same or different from each other. Each possibility represents a separate embodiment of the present invention.

As mentioned above, in some embodiments, mixtures of N,N'-diacetylethylenediamine (DAE) and side products (e.g., N-(2-aminoethyl)acetamide (AEA), and/or N-ethylideneethane-1,2-diamine (EED)) can also be formed in the process of dehydrogenation of ethylenediamine (ED) and ethanol. The mixture of DAE, EED and/or AEA are capable of being hydrogenated back to ethylenediamine (ED) and ethanol in accordance with the principles of the present invention.

In addition, mixtures of ethylenediamine (ED) with ethanol and methanol may be used in combination for hydrogen storage, in accordance with the principles of the present invention.

In one embodiment, for the above mentioned ethylenediamine/alcohol based hydrogen storage and release processes and systems, the catalyst is a ruthenium based complex. In another embodiment, the catalyst is a ruthenium based complex according to this invention as described herein below. In another embodiment, the catalyst is selected from compounds (i)-(vi) and (1)-(8). Each possibility represents a separate embodiment of the present invention. In another embodiment, the catalyst is compound iii. In another embodiment, the catalyst is compound 1.

c. Aminoalcohol LOHC

In one embodiment, this invention is directed to a method and a system to store hydrogen and release it on demand. In another embodiment, the method and process comprise and make use of aminoalcohol liquid-organic hydrogen carrier system (LOHC) to store hydrogen ($H_2$) and release it on demand. In another embodiment the aminoalcohol is 2-aminoethanol. In another embodiment, the aminoalcohol is 2-(methylamino)ethanol. In another embodiment, the aminoalcohol is 3-aminopropanol. In another embodiment, the maximal hydrogen storage capacity (HSC) of this reaction is 6.56 wt %.

In another embodiment, the process and system of this invention comprises and make use of 2-aminoethanol (AE) or 2-(methylamino)ethanol liquid-organic hydrogen carrier (LOHC) to store hydrogen ($H_2$) and release it on demand.

2-aminoethanol (AE) and 2-(methylamino)ethanol undergo catalytic dehydrogenation to form a cyclic dipeptide (glycine anhydride (GA) or N,N-dimethyl GA, respectively, with release of hydrogen. The dipeptide is hydrogenated back to 2-aminoethanol (AE) or -(methylamino)ethanol, each of which functions as a hydrogen storage system.

Thus, in one embodiment, the present invention relates to a process for the storage of hydrogen, the process comprises the step of reacting glycine anhydride (GA) with molecular hydrogen ($H_2$), in the presence of a catalyst, under conditions sufficient to generate 2-aminoethanol (AE) as a hydrogen storage system. In another embodiment, the present invention relates to a process for the storage of hydrogen, the process comprises the step of reacting N,N-dimethyl GA (N,N-dimethyl GA) with molecular hydrogen ($H_2$), in the presence of a catalyst, under conditions sufficient to generate 2-(methylamino)ethanol as a hydrogen storage system. The reaction, as well as the reverse reaction, dehydrogenation of 2-aminoethanol, are described in Schemes 3, 4a, 4b, and 5 hereinabove.

In accordance with this principle, another aspect of the present invention relates to a process for the storage and release of hydrogen ($H_2$), comprising the steps of:
(a) when hydrogen storage is desired, reacting glycine anhydride (GA) with molecular hydrogen ($H_2$) in the presence of a catalyst to generate 2-aminoethanol (AE); and
(b) when hydrogen release is desired, reacting 2-aminoethanol (AE) with a catalyst, under conditions sufficient to generate glycine anhydride and hydrogen ($H_2$).

Another aspect of the present invention relates to a process for the storage and release of hydrogen ($H_2$), comprising the steps of:
(a) when hydrogen storage is desired, reacting N,N-dimethyl GA with molecular hydrogen ($H_2$) in the presence of catalyst to generate 2-(methylamino)ethanol; and
(b) when hydrogen release is desired, reacting 2-(methylamino)ethanol with a catalyst, under conditions sufficient to generate N,N-dimethyl GA and hydrogen ($H_2$).

In another aspect, the present invention relates to system for the storage of hydrogen ($H_2$), the system comprises (i) glycine anhydride (GA) and/or N,N-dimethyl GA; and (ii) a catalyst, wherein the GA and/or N,N-dimethyl GA are capable of reacting with molecular hydrogen ($H_2$) in the presence of the catalyst, under conditions sufficient to generate 2-aminoethanol (AE) and/or 2-(methylamino)ethanol, respectively, as a hydrogen storage system.

In another aspect, the present invention relates to a system for the release of hydrogen ($H_2$), the system comprises (i) 2-aminoethanol (AE) and/or 2-(methylamino)ethanol; and (ii) catalyst, wherein the 2-aminoethanol and/or 2-(methylamino)ethanol are capable of being dehydrogenated in the presence of the catalyst, under conditions sufficient to generate glycine anhydride (GA) and/or N,N-dimethyl GA, respectively, and molecular hydrogen.

Both systems may be combined so as to form one general system containing three components (i) glycine anhydride (GA) and/or N,N-dimethyl GA; (ii) 2-aminoethanol (AE) and/or 2-(methylamino)ethanol; and (iii) a catalyst, wherein the catalyst is reacted with either GA/N,N-dimethyl GA or AE and/or Me-AE under conditions sufficient to store or release hydrogen, upon demand and as desired. In each of the aforementioned reactions, the same catalytic system can be used for the hydrogenation and dehydrogenation reactions. Alternatively, each of the reactions (i.e., hydrogenation and dehydrogenation) can be performed with different catalytic systems. In other words, the hydrogenation reactions can be performed with a first catalyst, and the dehydrogenation reaction can be performed with a second catalyst, wherein the first and second catalyst may be the same or different from each other. Each possibility represents a separate embodiment of the present invention.

As mentioned above, in some embodiments, mixtures of GA/N,N-dimethyl GA and linear peptides can also be formed in the process of dehydrogenation of 2-aminoethanol or 2-(methylamino)ethanol. The mixture of linear peptides and GA/N,N-dimethyl GA are capable of being hydrogenated back to AE in accordance with the principles of the present invention.

In addition, mixtures of 2-aminoethanol and 2-(methylamino)ethanol may be used in combination for hydrogen storage, in accordance with the principles of the present invention.

In one embodiment, for above mentioned aminoalcohol based hydrogen storage and release processes and systems, the catalyst is preferably a ruthenium based complex. More preferably, the catalyst is a ruthenium based complex according to this invention as described hereinbelow. Most preferably, the catalyst is selected from compounds (i)-(vi) and (1)-(4). Each possibility represents a separate embodiment of the present invention. In another embodiment, the catalyst is compound 1. In another embodiment, the catalyst is compound i.

The present invention relates to the basic principles of chemistry and physics of reversible and safe hydrogen storage systems for static and mobile applications. Examples of uses for hydrogen storage systems, are, e.g., fuel for combustion engines, fuel cells, such as in various self-propelled systems, including for example automobiles, trucks, ships, airplanes. Other applications can range from hydrogen-powered domestic machinery to rockets propellants, drones, space applications, just to name a few.

3. Catalysts

The above dehydrogenation reactions and hydrogenation can be catalyzed by any catalyst. In one embodiment, these reactions are catalyzed by transition metals and compounds and complexes containing same, as well as combinations thereof. As contemplated herein, the present invention encompasses (but is not limited to) the use of the following catalytic systems: 1) transition metals; 2) transition metal-containing compounds including transition metal complexes; and 3) any combination of the foregoing. Also, the catalyst may be based on a single transition metal, or the catalyst may contain more than one type of transition metal.

Examples of transition metal containing compounds include, but are not limited to chlorides (e.g., $RuCl_3$, $FeCl_3$, $AuCl$, $NiCl_2$, $CoCl_2$) oxides (e.g., $Fe_2O_3$, $CoO$, $NiO$), sulfides (e.g., $RuS_2$, $NiS$, $CoS$, $Fe_2S_3$), hydroxides ($Ru(OH)_3$, $Fe(OH)_3$, $Ni(OH)_2$, $Co(OH)_2$), carbonates, acetates (e.g., $Fe(CH_3CO_2)_2$, $Ni(CH_3CO_2)_2$, $Mn(CH_3CO_2)_2$, $Pd(CH_3CO_2)_2$, alkoxides, and the like.

Examples of compounds including more than one transition metal includes but are not limited to Copper chromite $Cu_2Cr2O_5$ (used industrially in ester hydrogenation), and bimetallic such as those disclosed in Wei, Z et al. Chem Soc. Rev., 2012, 41, 7994-8008, the contents of which are incorporated by reference in their entirety.

A variety of transition metal catalysts can be used in the context of the present invention. Examples include, but are not limited to catalysts based on transition metal selected from the group consisting of chromium (Cr), iron (Fe), manganese (Mn), cobalt (Co), nickel, (Ni), copper (Cu), silver (Ag), gold (Au), zinc (Zn), ruthenium (Ru), palladium (Pd), platinum (Pt), iridium (Ir), rhodium (Rh), molybdenum (Mo), tungsten (W) and any combination thereof. Each possibility represents a separate embodiment of the present invention.

In some embodiments, the transition metal catalyst is attached through any available positions to a solid support, or embedded or a solid support, or is located on the surface of a solid support, which may be based on an inorganic or organic material. In some embodiments, the solid support comprises an inorganic material selected from the group consisting of silica, alumina, magnesia, titania, zirconia, montmorillonite, phyllosilicate, zeolites, talc, clays, layered double hydroxides, apatites, and any combination thereof. In other embodiments, the solid support comprises an organic polymer selected from polystyrene, polyethylene, polypropylene, polyvinylchloride, polytetrafluoro ethylene, polyethylene glycol, and poly(organo)siloxanes, and combinations thereof. Each possibility represents a separate embodiment of the present invention.

It is understood that any of the catalysts described hereinabove may be used as is, or they may be formed during the catalytic reaction by combining the appropriate metal with its ligands so as to form the catalyst in situ. Thus, for example, the Ruthenium complexes described hereinbelow may be formed by combining Ruthenium precursors, such as Ruthenium salts and the appropriate ligands so as to form the catalytic complex in situ. Also, some of the complexes described below are "pre-catalyst", wherein the active catalytic species is formed in situ by combining the pre-catalyst with a base as described herein.

Ruthenium Complexes

In a preferred embodiment, the catalyst used in the processes of the invention is a Ruthenium based complex. A variety of Ruthenium complexes can be used in the process and system of the present invention. In general, any Ruthenium complex that catalyze the conversion of amide to amines and alcohols, and vice versa, may be utilized in the context of the present invention. More specifically, any Ruthenium complex that catalyze the conversion of DAE, glycine anhydride (GA) or N,N-dimethyl GA to ED and ethanol, 2-aminoethanol (AE) or 2-(methylamino)ethanol respectively, and vice versa, may be utilized in the context of the present invention.

(i) Pyridyl Complexes

In one embodiment, the Ruthenium complex is a pyridyl Ruthenium pincer complex described in U.S. Pat. No. 8,178,723. Such complexes are represented by any one of formulae A1, A2 and A3:

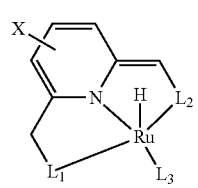

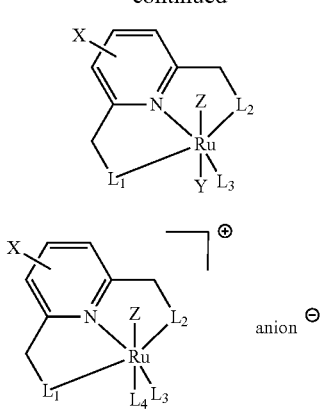

A2

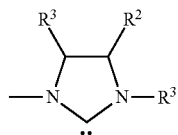

A3 wherein
- $L_1$ and $L_2$ are each independently selected from the group consisting of nucleophilic carbene (:C(R)$_2$), P(R)$_2$, P(OR)$_2$, N(R)$_2$, imine, SR, SH, S(=O)R, heteroaryl wherein the heteroatom is selected from nitrogen and sulfur, As(R)$_2$, Sb(R)$_2$ and an N-heretocyclic carbene represented by the structure:

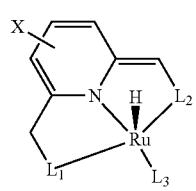

each of R, $R^2$ and $R^3$ are independently selected from the group consisting of alkyl, cycloalkyl, aryl, alkylaryl, heterocyclyl and heteroaryl;
- $L_3$ is a mono-dentate two-electron donor selected from the group consisting of CO, P(R)$_3$, P(OR)$_3$, NO$^+$, As(R)$_3$, Sb(R)$_3$, S(R)$_2$, nitrile (RCN) and isonitrile (RNC) wherein R is as defined above;
- $L_4$ is absent or is $L_3$;
- Y and Z are each independently H or an anionic ligand selected from the group consisting of halogen, OCOR, OCOCF$_3$, OSO$_2$R, OSO$_2$CF$_3$, CN, OH, OR, N(R)$_2$, RS and SH; wherein R is as defined above;
- X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety; and
- anion represents a group bearing a single negative charge.

In one embodiment, the Ruthenium complex is represented by the structure of formula A1. In a particular embodiment of formula A1, the Ruthenium complex is represented by the structure of formula B1:

B1

In another particular embodiment of formula A1, the Ruthenium complex is represented by the structure of formula C1:

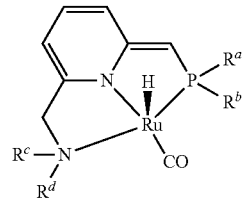

C1 wherein each of $R^a$, $R^b$, $R^c$ and $R^d$ is independently selected from the group consisting of alkyl, cycloalkyl, aryl, alkylaryl, heterocyclyl and heteroaryl.

In one currently preferred embodiment, each of $R^a$ and $R^b$ is tert-butyl. In another currently preferred embodiment, each of $R^c$ and $R^d$ are ethyl. In a particularly preferred embodiment, the Ruthenium complex is represented by the structure of formula (ii) (also designated "dearomatized RuPNN$^-$-Et$_2$").

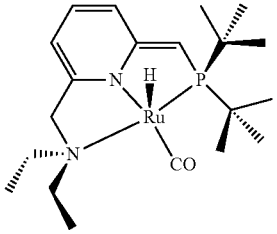

(ii)

When the Ruthenium complex is a compound of formula A1, the process of the invention does not require the addition of any base, however, some additional base (e.g., about one half equivalent of base relative to the Ruthenium complex is beneficial.

In another embodiment, the Ruthenium complex is represented by the structure of formula A2. Complexes of formula A2 are particularly useful in the aminoalcohol based system. In one particular embodiment, Z is H and Y is other than H in formula A2. In another embodiment, Z is H. In another embodiment, Y is Cl. In another embodiment, $L_3$ is CO. In another embodiment, Z is H, Y is Cl and $L_3$ is CO. In accordance with these embodiments, the process of the invention is conducted in the presence of at least one equivalent of a base relative to the Ruthenium complex. In another particular embodiment, each of Z and Y is other than H in formula A2. In accordance with this embodiment, the process of the invention is conducted in the presence of at least two equivalents of a base relative to the Ruthenium complex. In another particular embodiment, Z and Y are both H in formula A2. In accordance with this embodiment, no base is required for the process of the invention.

In one embodiment of formula A2, the Ruthenium complex is represented by the structure of formula B2.

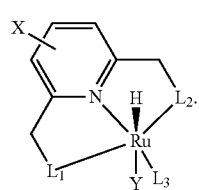

In another particular embodiment of formula A2, the Ruthenium complex is represented by the following structure of formula C2:

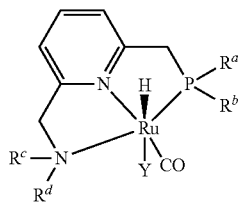

wherein each of $R^a$, $R^b$, $R^c$ and $R^d$ is independently selected from the group consisting of alkyl, cycloalkyl, aryl, alkylaryl, heterocyclyl and heteroaryl.

Complexes of formula C2 are particularly useful in the aminoalcohol based systems and processes. In another embodiment, $R^a$ and $R^b$ are each independently alkyl. In another embodiment, $R^a$ and $R^b$ are both t-Bu. In another embodiment, $R^c$ and $R^d$ are each independently alkyl. In another embodiment, $R^c$ and $R^d$ are both ethyl. In another embodiment, $R^c$ and $R^d$ are both t-Bu.

In one currently preferred embodiment, Y is halogen, such as chloro. In one embodiment, the Ruthenium complex is represented by the structure of formula (i) also designated "aromatized RuPNN-Et$_2$":

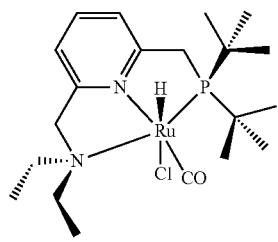

In another embodiment of the present invention, the Ruthenium complex is represented by the structure of formula A3. In one particular embodiment, Z is H in formula A3. In accordance with this embodiment, the process is conducted in the presence of at least one equivalent of a base relative to the Ruthenium complex. In another particular embodiment, Z is other than H in formula A3. In accordance with this embodiment, the process is conducted in the presence of at least two equivalents of a base relative to the Ruthenium complex.

Compounds of formula A2 (of which Compound (i) is a representative) and formula A3 are precursors of compounds of formula A1. Additional exemplary precursors of the complexes of formula A1 include, but are not limited to:

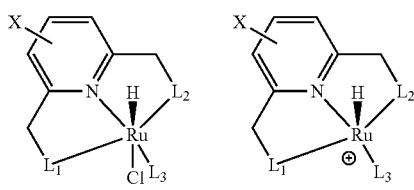

plus at least one equivalent of vase relative to Ru
(eg alkoxide, hydroxide)

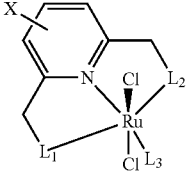

plus at least two equivalent of vase relative to Ru
(eg alkoxide, hydroxide)

It is understood that any one or more of the precursors can themselves function as catalysts in the process of the present invention.

The Ruthenium complexes of formulae A1, A2, A3, B1, C1, B2, C2, (i) and (ii) may be prepared in accordance with the methods described in U.S. Pat. No. 8,178,723, the contents of which are incorporated by reference herein in their entirety.

(ii) Bipyridyl Complexes:

In one embodiment, the Ruthenium complex is a bipyridyl pincer complex described in WO 2012/052996, including boronated bipyridyl and pyridyl complexes described therein. Such complexes are represented by any one of formulae A1', A2' or A3':

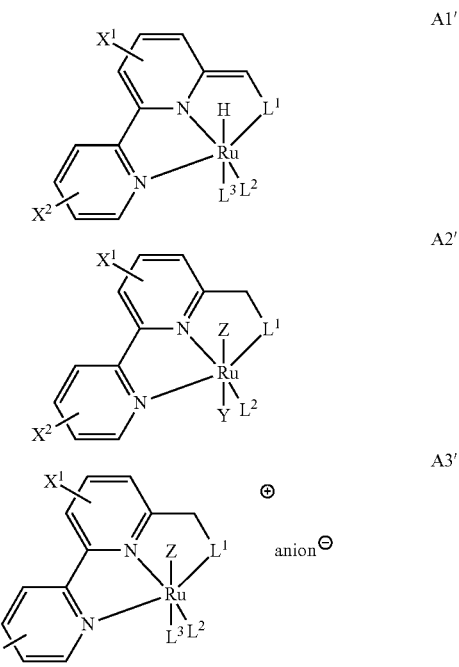

wherein $L^1$ is selected from the group consisting of phosphine (PR$^a$R$^b$), phosphite P(OR$^a$)(OR$^b$), phosphinite P(OR$^a$)

($R^b$), amine ($NR^aR^b$), imine, oxazoline, sulfide ($SR^a$), sulfoxide ($S(=O)R^a$), heteroaryl containing at least one heteroatom selected from nitrogen and sulfur; arsine ($AsR^aR^b$), stibine ($SbR^aR^b$) and a N-heterocyclic carbene represented by the structures:

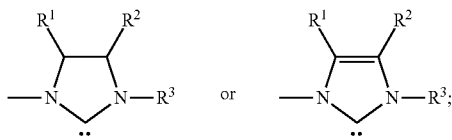

$L^2$ is a mono-dentate two-electron donor selected from the group consisting of CO, $PR^aR^bR^c$, $P(OR^a)(OR^b)(OR^c)$, $NO^+$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene and alkyne;

$L^3$ is absent or is $L^2$;

Y and Z are each independently H or an anionic ligand selected from the group consisting of H, halogen, OCOR, $OCOCF_3$, $OSO_2R$, $OSO_2CF_3$, CN, OR, $N(R)_2$ and RS;

$R^a$, $R^b$ and $R^c$ are each independently alkyl, cycloalkyl, aryl, heterocyclyl, heteroaryl, alkylcycloalkyl, alkylaryl, alkylheterocyclyl or alkylheteroaryl;

R, $R^1$, $R^2$ and $R^3$ are each independently H, alkyl, cycloalkyl, aryl, heterocyclyl, heteroaryl, alkylcycloalkyl, alkylaryl, alkylheterocyclyl or alkylheteroaryl;

$X^1$ represents zero, one, two or three substituents; and $X^2$ represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety; and anion represents a group bearing a single negative charge.

In one embodiment, $X^1$ and $X^2$ are absent (i.e, the bipyridine moiety is unsubstituted). In another embodiment, $L^1$ is phosphine ($PR^aR^b$). In another embodiment, $L^2$ is CO.

In one embodiment, the Ruthenium complex is represented by the structure of formula A1':

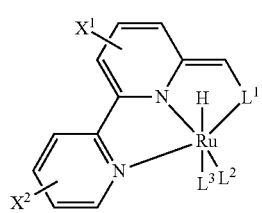

In a particular embodiment of formula A1', the Ruthenium complex is represented by the structure of formula B1'. In another particular embodiment of formula A1', the Ruthenium complex is represented by the structure of formula C1'.

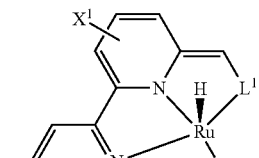

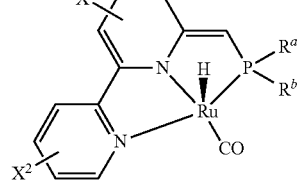

Each of $L^1$, $L^2$, $X^1$, $X^2$, $R^a$ and $R^b$ in Formulae B1' and C1' are as defined for formula A1'. Each possibility represents a separate embodiment of the present invention.

In one embodiment, each of $R^a$ and $R^b$ is tert-butyl. In another currently, each of $R^a$ and $R^b$ are isopropyl. Each possibility represents a separate embodiment of the present invention.

In one embodiment, the Ruthenium complex is represented by the structure of formula (vi).

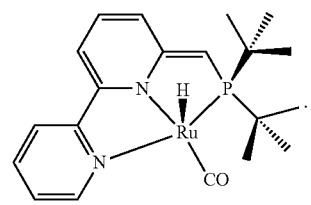

In another embodiment of the present invention, the Ruthenium complex is represented by the structure of formula A2':

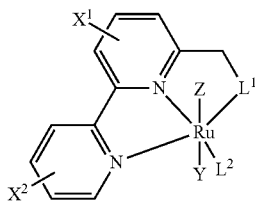

In one embodiment of Formula A2', Z and Y are either each H, each a halogen (e.g., F, Cl, Br, I) or one of Z and Y is H and the other a halogen. Each possibility represents a separate embodiment of the present invention. In another embodiment, $L_2$ is CO.

In one particular embodiment, Z is H and Y is other than H in formula A2'. When such a complex is used, the processes of the invention as described hereinbelow are typically conducted in the presence of at least one equivalent of a base relative to the Ruthenium complex. In another particular embodiment, each of Z and Y is other than H in formula A2'. When such a complex is used, the processes of the invention as described hereinbelow are typically conducted in the presence of at least two equivalents of a base relative to the Ruthenium complex. In another particular embodiment, Z and Y are both H in formula A2'. When such a complex is used, no base is required for the processes of the invention.

In one embodiment of formula A2', the Ruthenium complex is represented by the structure of formula B2':

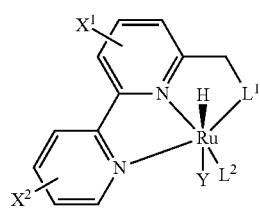

B2'

In another particular embodiment of formula A2', the Ruthenium complex is represented by the following structure of formula C2':

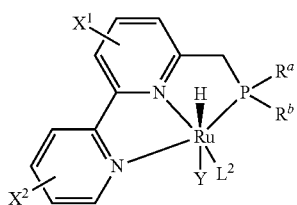

C2'

Each of $L^1$, $L^2$, $X^1$, $X^2$, Y, $R^a$ and $R^b$ in formulae B2' and C2' are as defined in formula A2'. Each possibility represents a separate embodiment of the present invention.

In one embodiment, Y is halogen, such as chloro. For example, the Ruthenium complex may be represented by the structure of any of formulae (iii), (iv) or (v):

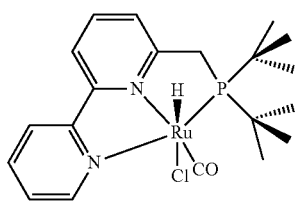

(iii)

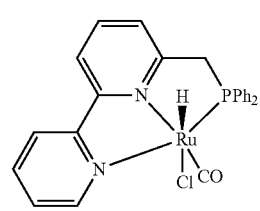

(iv)

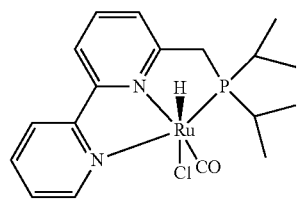

(v)

Complex of formula (iii) is particularly useful in the diaminoalkane/alcohol LOHC process as described hereinabove. In another embodiment of the present invention, the Ruthenium complex is represented by the structure of formula A3':

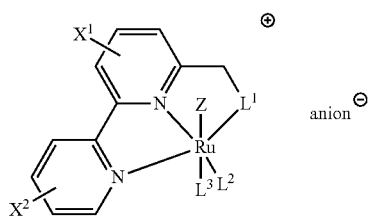

A3

In one particular embodiment, Z is H in formula A3'. When such a complex is used, the processes of the invention as described hereinbelow are typically conducted in the presence of at least one equivalent of a base relative to the Ruthenium complex. In another particular embodiment, Z is other than H in formula A3'. When such a complex is used, the processes of the invention as described hereinbelow are typically conducted in the presence of at least two equivalents of a base relative to the Ruthenium complex.

Compounds of formula A2' and formula A3' are precursors of compounds of formula A1'. Additionally some precursors of the complexes of formula A1' include, but are not limited to, compounds of general formulae (a) (b) and (c):

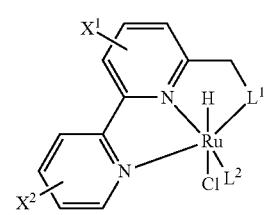

(a)

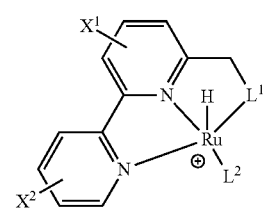

(b)

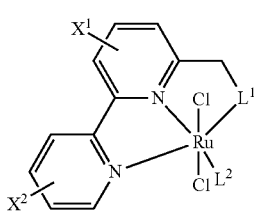

(c)

It is understood that any one or more of the precursors can themselves function as complexes in the process of the present invention. For example, when structures (a) and (b) and their equivalents are used, at least one equivalent of base relative to the Ruthenium complex can be used (e.g., alkoxide, hydroxide). Alternatively, when structure (c) or its equivalents are used, at least two equivalents of base relative to the Ruthenium complex can be used. Non-limiting examples of bases are alkoxide (e.g., t-butoxide, methoxide, ethoxide), hydroxide, hydride, amide (R$_2$N$^-$), and the like.

The Ruthenium complexes of formulae A1', A2', A3', B1', B2', C1', C2', (a), (b), (c), (iii), (iv), (v) and (vi), may be prepared in accordance with the methods described in WO 2012/052996, the contents of which are incorporated by reference herein in their entirety.

(iii) PNNH—Complexes

The inventors have unexpectedly discovered that pyridine-based pincer complexes of general formulae A1", A2", A3" and A4'" have superior activity at catalyzing the hydrogenation and dehydrogenation reactions described herein. The new complexes are a new class of pyridyl ruthenium pincer complexes with sec-amine coordination to the metal (i.e., a Ru—N—H group). The new pincer complexes, optionally in the presence of a base, act as effective catalysts under exceedingly mild conditions for acceptorless dehydrogenative coupling of alcohols to esters and hydrogenation of esters, among other reactions. The simplicity, generality and excellent atom-economy of these processes make them attractive for use both in small and large scale applications.

The Ruthenium complexes are pyridine-based PNNH pincer complexes of general formulae A1", A2", A3" and A4" which comprise a sec-amine coordination to the metal (i.e., a Ru—N—H group).

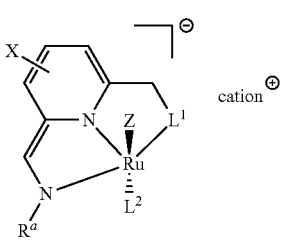

A1"

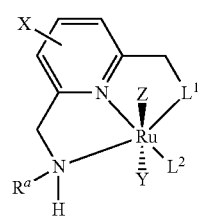

A2"

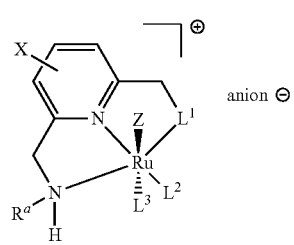

A3"

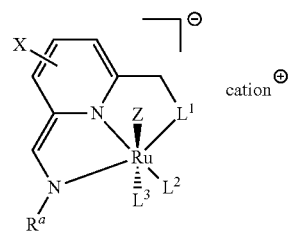

A4"

wherein

L$^1$ is selected from the group consisting of phosphine (PR$^b$R$^c$), phosphite P(OR$^b$)(OR$^c$), phosphinite P(OR$^b$) (R$^c$), amine (NR$^b$R$^c$), imine, oxazoline, sulfide (SR$^b$), sulfoxide (S(=O)R$^b$), heteroaryl containing at least one heteroatom selected from nitrogen and sulfur; arsine (AsR$^b$R$^c$), stibine (SbR$^b$R$^c$) and a N-heterocyclic carbene represented by the structures:

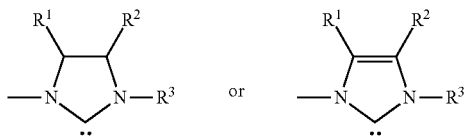

L$^2$ is a mono-dentate two-electron donor selected from the group consisting of CO, PR$^b$R$^c$R$^d$, P(OR$^b$)(OR$^c$)(OR$^d$), NO$^+$, AsR$^b$R$^c$R$^d$, SbR$^b$R$^c$R$^d$, SR$^b$R$^c$, nitrile (RCN), isonitrile (RNC), N$_2$, PF$_3$, CS, heteroaryl, tetrahydrothiophene, alkene and alkyne;

L$^3$ is absent or is L$^2$;

Y and Z are each independently H or an anionic ligand selected from the group consisting of halogen, OCOR, OCOCF$_3$, OSO$_2$R, OSO$_2$CF$_3$, CN, OR, N(R)$_2$ and RS;

R$^a$ is H, alkyl, cycloalkyl, aryl, heterocyclyl, heteroaryl, alkylcycloalkyl, alkylaryl, alkylheterocyclyl or alkylheteroaryl;

R$^b$, R$^c$ and R$^d$ are each independently alkyl, cycloalkyl, aryl, heterocyclyl, heteroaryl, alkylcycloalkyl, alkylaryl, alkylheterocyclyl or alkylheteroaryl;

R, R$^1$, R$^2$ and R$^3$ are each independently H, alkyl, cycloalkyl, aryl, heterocyclyl, heteroaryl, alkylcycloalkyl, alkylaryl, alkylheterocyclyl or alkylheteroaryl;

X represents zero, one, two or three substituents independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety; anion$^\ominus$ represents a group bearing a single negative charge; and cation$^\oplus$ represents a group bearing a single positive charge.

In one embodiment, X is absent (i.e., the pyridine moiety is unsubstituted). In another embodiment, $L^1$ is phosphine ($PR^bR^c$). In another embodiment, $L^2$ is CO. In another embodiment, Z and Y are independently H or halogen. In another embodiment, $R^a$ is alkyl. In another embodiment, $R^b$ and $R^c$ are each independently alkyl. In another embodiment, $R^a$, $R^b$ and $R^c$ are t-butyl. The cation$^\oplus$ may be selected from the group consisting of $Li^+$, $Cs^+$, $K^+$, $Na^+$, and, $N(R)_4^+$ (R═H or alkyl). The anion$^\ominus$ may be selected from the group consisting of $BF_4^-$, $PF_6^-$, $B(C_6F_5)_4^-$, $B(C_6H_5)_4^-$, $^-OCOCF_3$, $^-OSO_2R$, $F^-$, $Cl^-$, $Br^-$, and $I^-$. Each possibility represents a separate embodiment of the present invention.

In one embodiment, the Ruthenium complex is represented by the structure of formula A1". In a particular embodiment of formula A1", Z is H, and the complex is represented by the structure A1''':

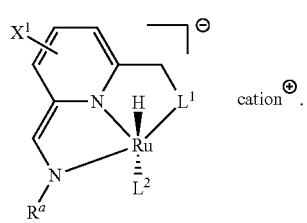

A1'''

In another particular embodiment of formula A1", the Ruthenium complex is represented by the structure of formula B 1":

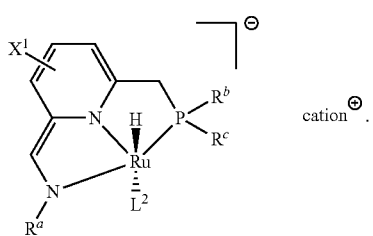

B1"

In one embodiment of formula B1", $L^2$ is CO. In another embodiment of formula B1", $R^a$ is selected from the group consisting of H, alkyl, cycloalkyl, aryl, alkylaryl, heterocyclyl and heteroaryl; and $R^b$ and $R^c$ are each independently selected from the group consisting of alkyl, cycloalkyl, aryl, alkylaryl, heterocyclyl and heteroaryl. In a currently preferred embodiment of formula B1", $R^a$ is selected from the group consisting of H, methyl, ethyl, propyl, isopropyl, n-butyl, sec-butyl, isobutyl, t-butyl and benzyl; and $R^b$ and $R^c$ are each independently selected from the group consisting of methyl, ethyl, propyl, isopropyl, n-butyl, sec-butyl, isobutyl, t-butyl and benzyl. In another embodiment, $R^a$, $R^b$ and $R^c$ are t-butyl.

In one embodiment, a crystallographically characterized novel monoanionic enamido Ru(II) complex (4) is obtained from the hydridochloride complex (1) upon addition of 2.5 equiv. of base by deprotonation of the amine proton as well as the methylene proton of the N-arm of the pincer ligand. The double deprotonated anionic enamido Ru(II) complex, formed in situ in the catalytic reactions of the processes of the invention, is presumed to be the actual active catalyst in these reactions.

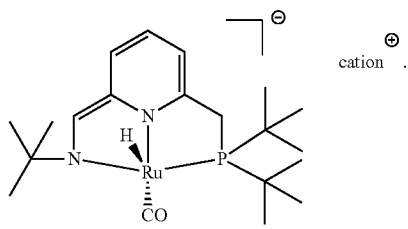

4

In one particular embodiment, the cation in complex 4 is $K^+$.

In another embodiment of the present invention, the Ruthenium complex is represented by the structure of formula A2". In one embodiment of formula A2", the Ruthenium complex is represented by the structure of formula B2".

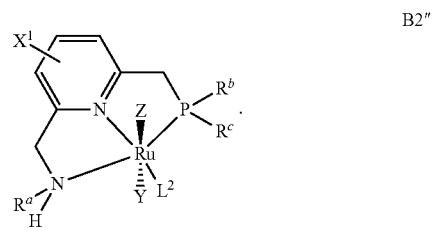

B2"

Examples of formula B2" include complexes 1, 2 or 3. Each possibility represents a separate embodiment of the present invention.

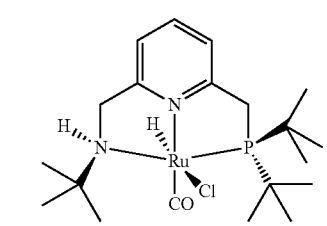

1

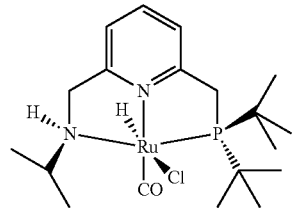

2

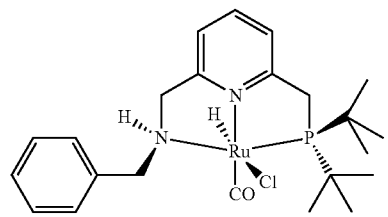

3

In another embodiment of the present invention, the Ruthenium complex is represented by the structure of formula A3". Complex 1 is particularly useful in the processes and systems of this invention. In another embodiment of the present invention, the Ruthenium complex is represented by the structure of formula A4".

Depending on the complex being used, the reaction permits the optional use of one or more equivalents of a base relative to the metal complex. For example, in one embodiment, when the Ruthenium complex is represented by the structure of formula A1" or A4" wherein Z is H, the reaction is conducted in the absence or the optional presence of a base. In another embodiment, for complexes of formula A1" or A4" wherein Z is other than H, the process is conducted in the presence of at least one equivalent of base relative to the metal complex. In another embodiment, when the Ruthenium complex is represented by the structure of formula A2" or A3" wherein Z is H and Y is an anionic ligand, the reaction is conducted in the presence of at least one equivalent of a base, preferably in the presence of at least 2 equivalents of a base, more preferably in the presence of at about 2.5 equivalents of a base relative to the metal complex. In another embodiment, when the Ruthenium complex is represented by the structure of formula A2" or A3" wherein Z and Y are each an anionic ligand, the reaction is conducted in the presence of at least two equivalents of a base, preferably in the presence of at least 3 equivalents of a base, more preferably in the presence of at least 3.5 equivalents of a base relative to the metal complex. Each possibility represents a separate embodiment of the present invention.

Unless indicated otherwise, reference to "equivalent of a base" as used herein means the number of equivalents of a base used relative to the metal complex.

Also described herein are processes for preparing the Ruthenium complexes of formulae A1", A2", A3" and A4", and intermediates used in these processes.

It is understood that complexes of formula A2" are precursors of the complexes of formula A1", wherein complex A1" is obtained by treatment of complex A2" with a base. One equivalent of the base deprotonates the benzylic hydrogen from complex A2", while another base equivalent deprotonates the amine nitrogen, leading to a dearomatized structure of formula A1". Thus, in one embodiment, the present invention relates to a process for preparing a Ruthenium complex represented by the structure of formula A1" by reacting a Ruthenium complex of formula A2" in the presence of at least 2 equivalents of a base relative to the metal complex (Scheme 9):

Scheme 9

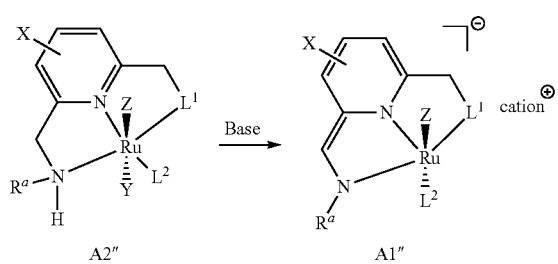

A2" → A1"

wherein $L^1$, $L^2$, X, Y and $R^a$ are defined as described above.

One particular embodiment of said process comprises preparing a Ruthenium complex represented by the structure of formula 4 from a precursor of formula 1 (Scheme 10):

Scheme 10

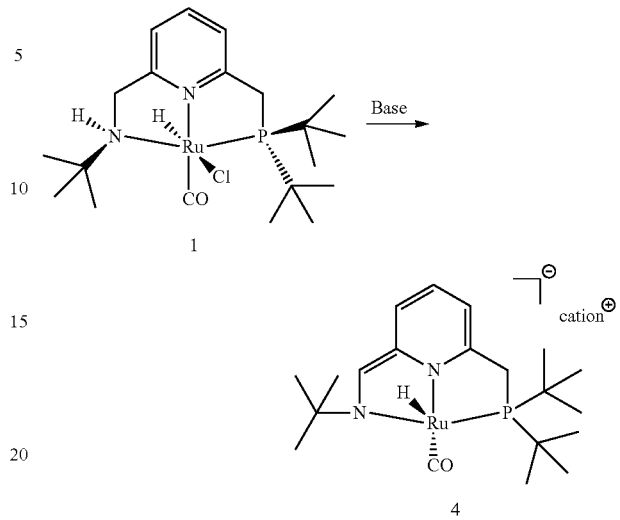

Alternatively, complex A3" can also be used as a catalyst in the processes of the present invention. In this case, treatment of compound A3" with a base yields a compound of formula A4" (Scheme 11):

Scheme 11

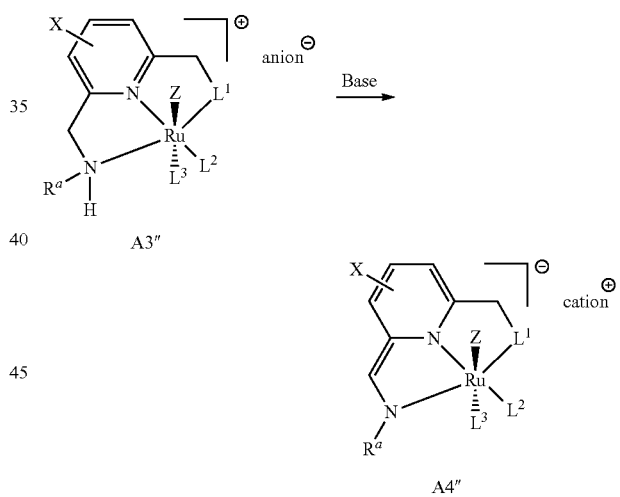

A3" → A4"

The Ruthenium complex represented by the structure of formula A2" may be prepared by reacting a precursor of formula B with a Ruthenium reagent represented by the structure $Ru(Z)(Y)(L^2)(P(Ar)_3)$ (Scheme 12)

Scheme 12

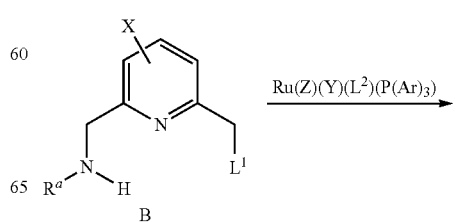

B

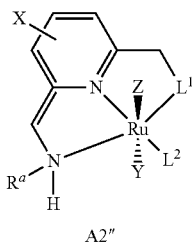

wherein Ar is phenyl or an alkyl-substituted phenyl.

In one particular embodiment, the process comprises the step of reacting a precursor of formula B' with Ru(H)Cl(CO)(PPh₃) to generate a compound of formula 1, 2 or 3:

Scheme 13

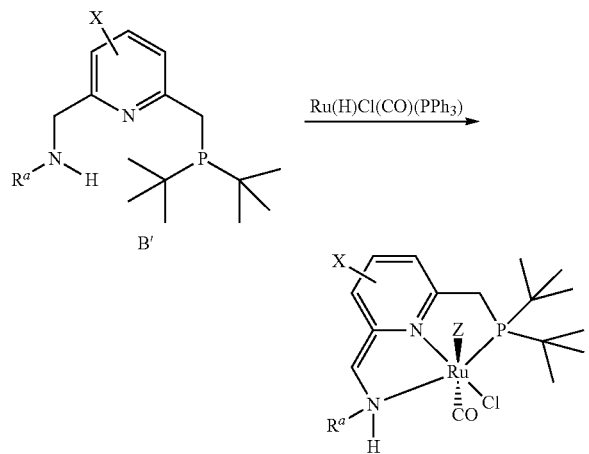

wherein $R^a$ is t-butyl (compound 1), isopropyl (compound 2) or benzyl (compound 3).

The Ruthenium complexes of formulae A1", A2", A3", A4", A1''', B1", B2", 1, 2, 3 and 4 may be prepared in accordance with the methods described in the experimental section hereinbelow.

In some embodiments, the Ruthenium complex acts as a catalyst (and is thus designated "Ruthenium catalyst").

System

In one embodiment, this invention is directed to a LOHC system for the storage and release of hydrogen (H₂) on demand, the system comprises (i) glycine anhydride (GA) or N,N-dimethyl GA; (ii) 2-aminoethanol (AE) or 2-(methylamino) ethanol; and (iii) a first catalyst and a second catalyst, wherein the first catalyst is capable of reacting with glycine anhydride (GA) or N,N-dimethyl GA under conditions sufficient to store hydrogen, and wherein the second catalyst is capable of reacting with 2-aminoethanol or 2-(methylamino) ethanol under conditions sufficient to release hydrogen, as desired, and wherein the first and second catalyst may be the same or different In another embodiment, the first and second catalysts are the same.

In one embodiment, this invention is directed to a LOHC system for the release of hydrogen. In another embodiment, the system comprises (i) 2-aminoethanol (AE) or 2-(methylamino) ethanol; and (ii) a catalyst, wherein said 2-aminoethanol or 2-(methylamino) ethanol is capable of being dehydrogenated in the presence of said catalyst, under conditions sufficient to generate glycine anhydride (GA) or N,N-dimethyl GA and molecular hydrogen. In one embodiment, this invention is directed to a LOHC system for the storage of hydrogen. In another embodiment, the system comprises (i) glycine anhydride (GA) or N,N-dimethyl GA; and (ii) a catalyst, wherein said glycine anhydride or N,N-dimethyl GA is capable of reacting with hydrogen (H₂) in the presence of said catalyst, under conditions sufficient to generate 2-aminoethanol (AE) or 2-(methylamino) ethanol as a hydrogen storage system.

In one embodiment, this invention is directed to a LOHC system for the storage and release of hydrogen (H₂) upon demand, the system comprises (i) N,N'-diacetylethylenediamine (DAE); (ii) ethylenediamine (ED) and ethanol; and (iii) a first catalyst and a second catalyst, wherein the first catalyst is capable of reacting with DAE under conditions sufficient to store hydrogen, and wherein the second catalyst is capable of reacting with ethylenediamine (ED) and ethanol under conditions sufficient to release hydrogen, as desired, and wherein the first and second catalyst may be the same or different In another embodiment, the first and second catalysts are the same.

In one embodiment, this invention is directed to a LOHC system for the storage of hydrogen (H₂). In another embodiment, the system comprises (i) N,N'-diacetylethylenediamine (DAE); and (ii) a catalyst, wherein said N,N'-diacetylethylenediamine (DAE) is capable of reacting with molecular hydrogen (H₂) in the presence of said catalyst, under conditions sufficient to generate ethylenediamine (ED) and ethanol as a hydrogen storage system.

In one embodiment, this invention is directed to a LOHC system for the release of hydrogen (H₂). In another embodiment, the system comprises (i) diaminoalkane, (ii) alcohol and (iii) a catalyst, wherein the diaminoalkane and alcohol are capable of being dehydrogenated in the presence of said catalyst, under conditions sufficient to generate the corresponding diamidoalkane and hydrogen. In another embodiment, the diaminoalkane is ethylenediamine and the alcohol is ethanol.

In one embodiment, this invention is directed to a LOHC system. In another embodiment, the LOHC system is used for a hydrogen fuel cell. In another embodiment, the LOHC system is used for fueling internal combustion engine. The LOHC of this invention (2-aminoethanol (AE), 2-(methylamino) ethanol, ethylenediamine+ethanol) release hydrogen on-board in vehicles powered by a hydrogen fuel cell, for internal combustion engine, or the LOHC systems store and release hydrogen at service stations, garages, central fleet refueling stations, and in residential individuals' homes, or other points of use. The release of the hydrogen is an on-site generation; and can be produced in individuals' homes or other points of use. Following the release of hydrogen, the LOHC is recovered from the dehydrogenated compounds in the presence of pressurized hydrogen.

In one embodiment, the LOHC system of this invention is used for dispensing and monitoring hydrogen based fuel in a vehicle. The system is configured to store, release and dispense the hydrogen in the vehicle. The system also includes a fuel delivery system on the vehicle configured to deliver the hydrogen to the engine, and a control system configured to control the producing system and to monitor the use of the hydrogen by the vehicle.

This invention provides a method for releasing hydrogen gas from the LOHC of this invention and using the hydrogen storage for vehicles powered by a hydrogen fuel cell and/or for internal combustion engine.

In one embodiment, the LOHC can be pumped or poured for distribution to holding tanks and storage vessels. The liquid is easily transported using conventional methods for liquid transport and distribution (pipelines, railcars, tanker trucks). The hydrogen is generated on-site in the vehicle or by a dehydrogenation reactor system that delivers hydrogen and recovers the dehydrogenated substrate in a hydrogenation reactor site.

In one embodiment, the LOHC system of this invention for use in a vehicle comprises a reaction chamber configured to collect the LOHC and the catalyst of the invention; a heating element configured to heat the LOHC and the catalyst to release hydrogen; a buffer tank in flow communication with the reaction chamber configured to collect and temporarily store the hydrogen; a compressor system in flow communication with the buffer tank configured to pressurize the hydrogen to a selected pressure;a storage system in flow communication with the compressor system configured to store a selected quantity of the hydrogen the selected pressure; a dispensing system in flow communication with the storage system configured to dispense the hydrogen to the hydrogen fuel cell or to the internal combustion engine. A second dispensing system in flow communication with the reaction chamber configured to dispense spent of the reaction to a spent tank, wherein the dehydrogenated substrate is recovered in the presence of pressurized hydrogen. The recovery of the dehydrogenated substrate is done on-board or off-board.

Chemical Definitions

As used herein, the term "diaminoalkane" denotes an aliphatic diamine, i.e., a hydrocarbon chain bearing two amino moieties. Examples of diaminoalkanes are selected from but not limited to: 1,2-ethylenediamine (ED), propylenediamine, propane-1,2-diamine, butane-2,3-diamine, propane-1,3-diamine, butane-1,3-diamine and the like. In one embodiment, the diaminoalkane is 1,2-ethylenediamine (ED). In one embodiment, the aminoalkane is a $C_1$-$C_6$ aliphatic hydrocarbon chain, which may be linear or branched, substituted with two amino ($NH_2$) moieties.

As used herein, the term "diamidoalkane" denotes an aliphatic diamide, or alkane-diamide, i.e., a hydrocarbon chain bearing two amide moieties (or peptide bonds). Examples of diamidoalkanes are selected from but not limited to: N,N-(ethane-1,2-diyl)diacetamide or N,N'-diacetylethylenediamide (DAE), N,N'-(propane-1,3-diyl)diacetamide, N,N'-(ethane-1,2-diyl)diformamide, N,N'-(propane-1,3-diyl)diacetamide, N,N'-(propane-1,3-diyl) diformamide, N,N'-(2-methylpropane-1,3-diyl)diacetamide, N,N'-(1-methylpropane-1,3-diyl)diacetamide, N,N'-(2-methylpropane-1,3-diyl)diformamide, and the like. In one embodiment, the diamidoalkane is N,N'-diacetylethylenediamide (DAE). In one embodiment, the amidoalkane is a $C_1$-$C_6$ aliphatic hydrocarbon chain, which may be linear or branched, comprising two amide (NHCO) moieties.

As used herein, the term "alcohol" is any organic compound bearing a hydroxyl functional group, in which the hydroxyl (—OH) is bound to a saturated carbon atom. In one embodiment, the alcohol is an aliphatic alcohol. In another embodiment, the alcohol is unsubstituted. Examples for alcohols are selected from but not limited to: ethanol, methanol, propan-1-ol (n-propanol), propan-2-ol (isopropanol), n-butanol, pentanol, cyclohexanol, isobutyl-alcohol, tert-amyl-alcohol and the like. In one embodiment, the alcohol is a primary alcohol. In another embodiment, the alcohol is an unsubstituted $C_1$-$C_4$ aliphatic hydrocarbon chain, which may be linear or branched, substituted with one hydroxyl moiety.

As used herein, the term "aminoalcohol" denotes an aliphatic alcohol substituted with one amino group, i.e., a hydrocarbon chain bearing one hydroxyl group and one amino group. Examples of aminoalcohol are selected from but not limited to: 2-aminoethanol (AE), 2-(methylamino) ethanol, 3-aminopropanol, 3-aminobutanol, 4-aminobutanol and the like. In one embodiment, the aminoalcohol is 2-aminoethanol (AE). In one embodiment, the aminoalcohol is 2-(methylamino)ethanol. In one embodiment, the aminoalcohol is a $C_1$-$C_6$ aliphatic hydrocarbon chain, which may be linear or branched, substituted with one amino ($NH_2$) moiety and one hydroxyl (OH) moiety.

As used herein, the term "glycine anhydride" or "GA" denotes the cyclic compound 1,4-dimethylpiperazine-2,5-dione (structure hereinbelow wherein R=H). As used herein, the term "N,N-dimethyl glycine anhydride" or "N,N-dimethyl GA" denotes the cyclic compound 1,4-dimethyl-piperazine-2,5-dione (structure hereinbelow wherein R=$CH_3$).

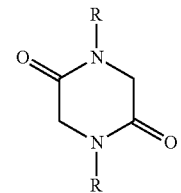

As used herein, the term alkyl, used alone or as part of another group, refers, in one embodiment, to a "$C_1$ to $C_{12}$ alkyl" and denotes linear and branched, saturated or unsaturated (e.g., alkenyl, alkynyl) groups, the latter only when the number of carbon atoms in the alkyl chain is greater than or equal to two, and can contain mixed structures. Non-limiting examples are alkyl groups containing from 1 to 6 carbon atoms ($C_1$ to $C_6$ alkyls), or alkyl groups containing from 1 to 4 carbon atoms ($C_1$ to $C_4$ alkyls). Examples of saturated alkyl groups include, but are not limited to, methyl, ethyl, n-propyl, isopropyl, n-butyl, iso-butyl, sec-butyl, tert-butyl, amyl, tert-amyl, and hexyl. Examples of alkenyl groups include, but are not limited to, vinyl, allyl, butenyl and the like. Examples of alkynyl groups include, but are not limited to, ethynyl, propynyl and the like. Similarly, the term "$C_1$ to $C_{12}$ alkylene" denotes a bivalent radical of 1 to 12 carbons.

The alkyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents. By way of illustration, an "alkoxyalkyl" is an alkyl that is substituted with an alkoxy group.

The term "cycloalkyl" used herein alone or as part of another group, refers to a "$C_3$ to $C_8$ cycloalkyl" and denotes any unsaturated or unsaturated (e.g., cycloalkenyl, cycloalkynyl) monocyclic or polycyclic group. Nonlimiting examples of cycloalkyl groups are cyclopropyl, cyclobutyl, cyclopentyl, cyclohexyl or cycloheptyl. Examples or cycloalkenyl groups include cyclopentenyl, cyclohexenyl and the like. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl. An alkylaryl group denotes an alkyl group bonded to an aryl group (e.g., benzyl).

The term "heteroaryl" used herein alone or as part of another group denotes a heteroaromatic system containing at least one heteroatom ring atom selected from nitrogen, sulfur and oxygen. The heteroaryl contains 5 or more ring atoms. The heteroaryl group can be monocyclic, bicyclic, tricyclic and the like. Also included in this expression are the benzoheterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

The term "heterocyclic ring" or "heterocyclyl" used herein alone or as part of another group denotes a five-membered to eight-membered rings that have 1 to 4 heteroatoms, such as oxygen, sulfur and/or nitrogen. These five-membered to eight-membered rings can be saturated, fully unsaturated or partially unsaturated. Non-limiting examples of heterocyclic rings include piperidinyl, piperidinyl, pyrrolidinyl pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubstituted or substituted through available atoms with one or more groups defined hereinabove for alkyl.

The inorganic support which is attached to the bipyridine ring can be, for example, silica, silica gel, glass, glass fibers, titania, zirconia, alumina and nickel oxide.

The polymer which is attached to the bipyridine pyridine ring can be, for example, selected from polyolefins, polyamides, polyethylene terephthalate, polyvinylchloride, polyvinylidenechloride, polystyrene, polymethracrylate, natural rubber, polyisoprene, butadiene-styrene random copolymers, butadiene acrylonitrile copolymers, polycarbonate, polyacetal, polyphenylenesulfide, cyclo-olefin copolymers, styrene-acrylonitrile copolymers, ABS, styrene-maleic anhydride copolymers, chloroprene polymers, isobutylene copolymers, polystyrene, polyethylene, polypropylene, and the like.

The term "anion" as used herein refers to any moiety or group bearing a negative charge. Examples of anionic moieties include, but are not limited to halogen (e.g., F, Cl, Br, I), OCOR', OCOCF$_3$, OSO$_2$R', OSO$_2$CF$_3$, BF$_4$, PF$_6$, SbF$_6$, BR$_4$, ClO$_4$, AlCl$_4$, CN, OH or OR' wherein R' is selected from alkyl, cycloalkyl, aryl, alkylaryl, heterocyclyl and heteroaryl, wherein each of the alkyl, cycloalkyl, aryl, alkylaryl, heterocyclyl and heteroaryl is as defined above.

EXAMPLES

Example 1

Preparation of Ruthenium Complexes

The Ruthenium complexes of formulae A1, A2, A3, B1, C1, B2, C2, (i) and (ii) may be prepared in accordance with the methods described in U.S. Pat. No. 8,178,723, the contents of which are incorporated by reference herein in their entirety.

The Ruthenium complexes of formulae A1', A2', A3', B1', B2', C1', C2', (a), (b), (c), (iii), (iv), (v) and, (vi) may be prepared in accordance with the methods described in WO 2012/052996, the contents of which are incorporated by reference herein in their entirety.

Ruthenium complexes of formulae A1", A2", A3" and A4", as well as compounds encompassed by such formulae, are prepared in accordance with the methods described below.

Three different PNN—H ligands bearing substituents R=tert-butyl (L1), isopropyl (L2) and benzyl (L3) were synthesized by reaction of 2-(ClCH$_2$)-6-($^t$Bu$_2$P(BH$_3$)CH$_2$) pyridine with the corresponding amines viz. tert-BuNH$_2$, ipr-NH$_2$, and benzylamine respectively (Scheme 14). The amines were used as solvents in excess to prevent over-alkylation on the nitrogen. The corresponding ruthenium complexes were obtained in good yields (85-90%) by reacting the corresponding PNN—H ligands with Ru(H)Cl(CO)(PPh$_3$)$_3$ in THF at 65° C. (Scheme 14).

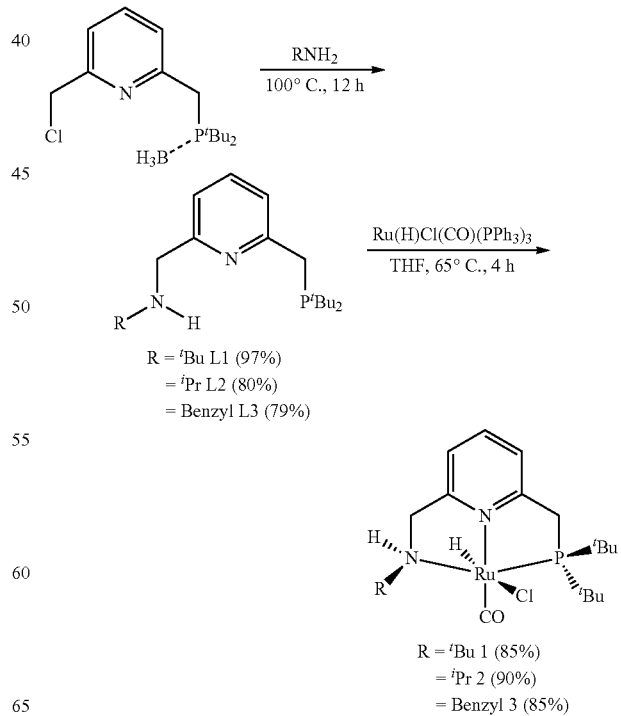

Scheme 14. Synthesis of PNN-H ligands and thier corresponding Ru(II) complexes.

The fully characterized complexes 1-3 give rise to a singlet around 109.0 ppm in the $^{31}P\{^1H\}$ NMR spectrum. In $^1H$ NMR, the hydride bound to Ru appears as a doublet around −15.0 ppm (d, $J_{HP}$ ~13.0 Hz). The inequivalent geminal benzylic methylene protons attached to phosphorus appear in all cases as a doublet of doublets around 3.5 ppm and 3.42 ppm. The methylene protons attached to N resonate further downfield in the region 4.7-4.3 ppm. The carbonyl carbon in the $^{13}C\{^1H\}$ NMR spectrum exhibits the most downfield shift resonating around 208.0 ppm ($J_{CP}$~16.0 Hz) with a characteristic doublet. In the IR spectra, the carbonyl group absorbs in the range v(CO)=1898-1896 $cm^{-1}$, indicating a slightly higher back-bonding than in the analogous complex RuPNN-$Et_2$ (v(CO)=1901 $cm^{-1}$) previously disclosed (U.S. Pat. No. 8,178,723).

Figure 2:
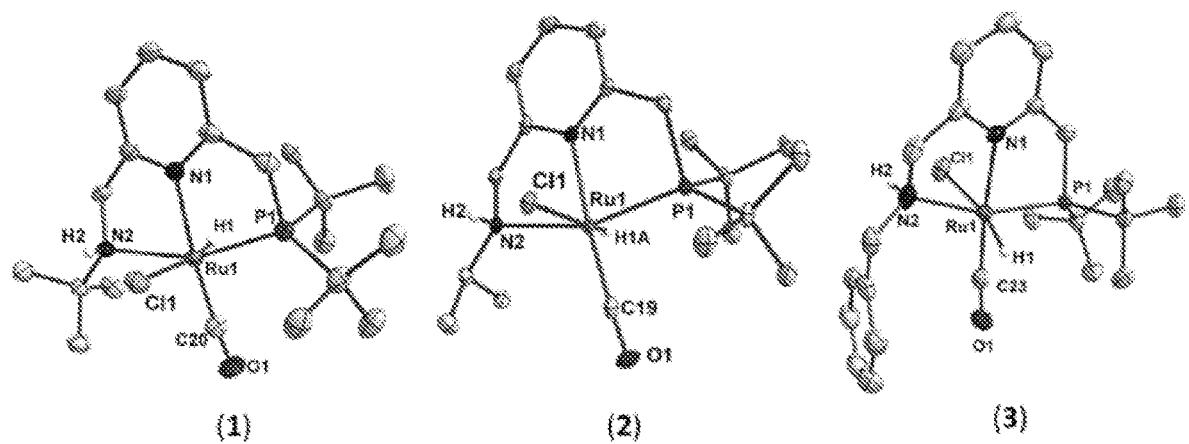
FIG. 2: shows the X-ray structure of Ruthenium complexes 1-3. Hydrogen atoms are omitted for clarity.

Single crystals suitable for X-ray diffraction of complexes 1-3 were obtained by slow diffusion of pentane into concentrated solutions of the complexes in $CH_2Cl_2$, similar to the structure of RuPNN-$Et_2$ (FIG. 1, compound (i)). These complexes also exhibit a distorted meridional octahedral structure with phosphorus, carbonyl and chloride atoms trans to the amine nitrogen, pyridine and hydride respectively. In all cases the substituents attached to nitrogen are equatorially disposed due to the steric hindrance on either side of the N1-Ru—N2 plane. The perspective views of the complexes are shown in FIG. 2. Compared to the RuPNN-$Et_2$, the distances of the chelating atoms to the metal were similar except for the distance of the amine nitrogen. Judging from their bond distances, the sec-amine coordinated ligands—of complexes 1, 2 and 3 are bound significantly more strongly, with Ru—N bond distances shorter by approximately 0.5 Å. However these distances are in the expected range when compared to the reported sec-amine coordinated pincer complex $Ru^{(II)}(2-(iPr_2PC_2H_4NHCH_2—)$ pyridine).

Next, the reactivity of 1 with a base was explored. It was formerly observed that with the analogous RuPNN-$Et_2$, addition of an equivalent of base leads to deprotonation of the benzylic phosphine arm, with concomitant de-aromatization of the pyridine based pincer group. In the case of the sec-amine coordinated complex 1, where the coordinated amine proton is of enhanced acidity (as compared with non-coordinated amine), a competition between the benzylic arm and the N—H group is expected.

Figure 3:
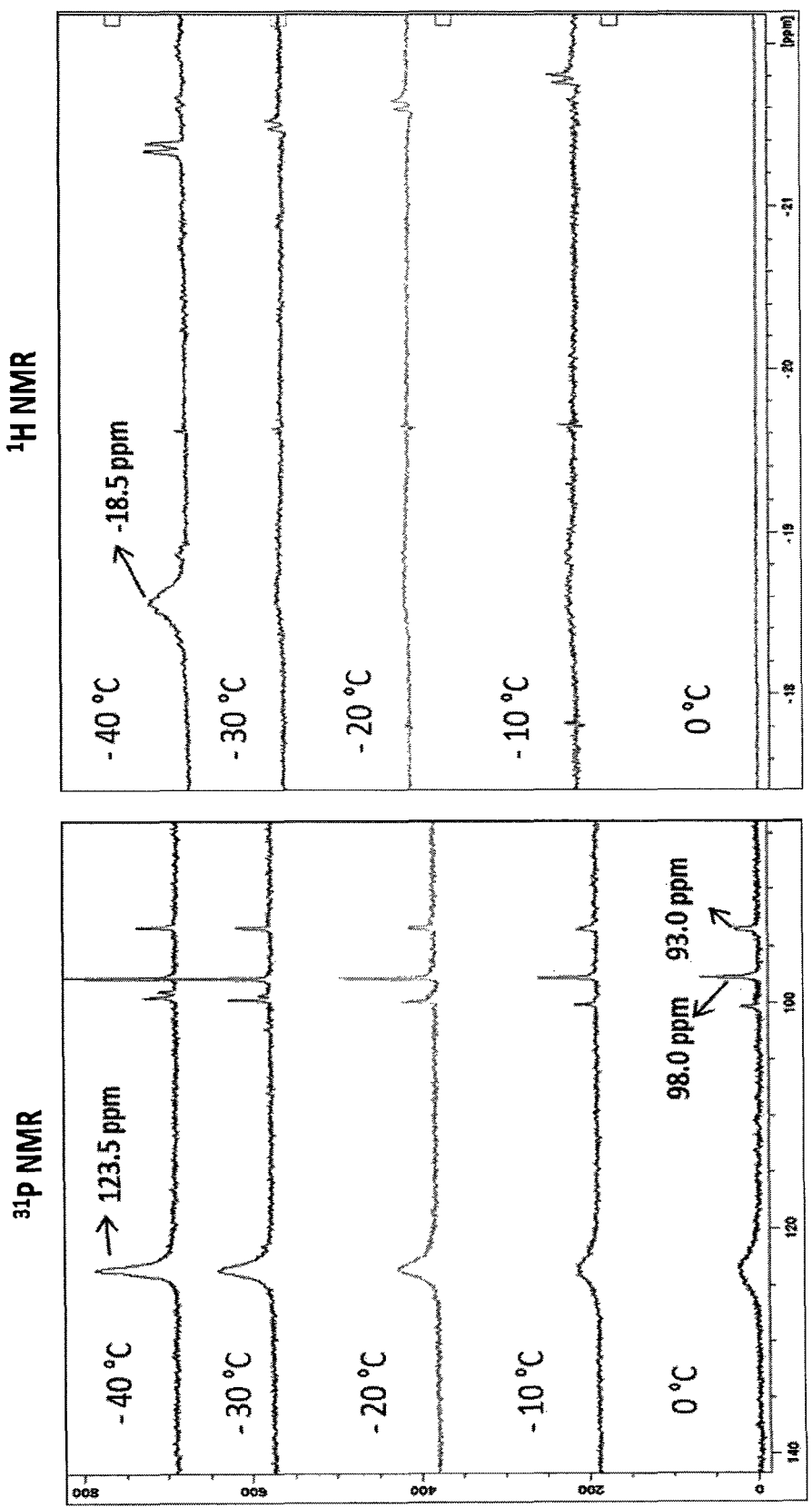
FIG. 3: Cooling a reaction mixture of 1 with 2.2 equiv. of KHMDS added at RT in THF, depicting the sharpening of the signal at 123.5 ppm in $^{31}P\{^1H\}$ NMR and −18.5 in $^1H$ NMR.
Figure 4:
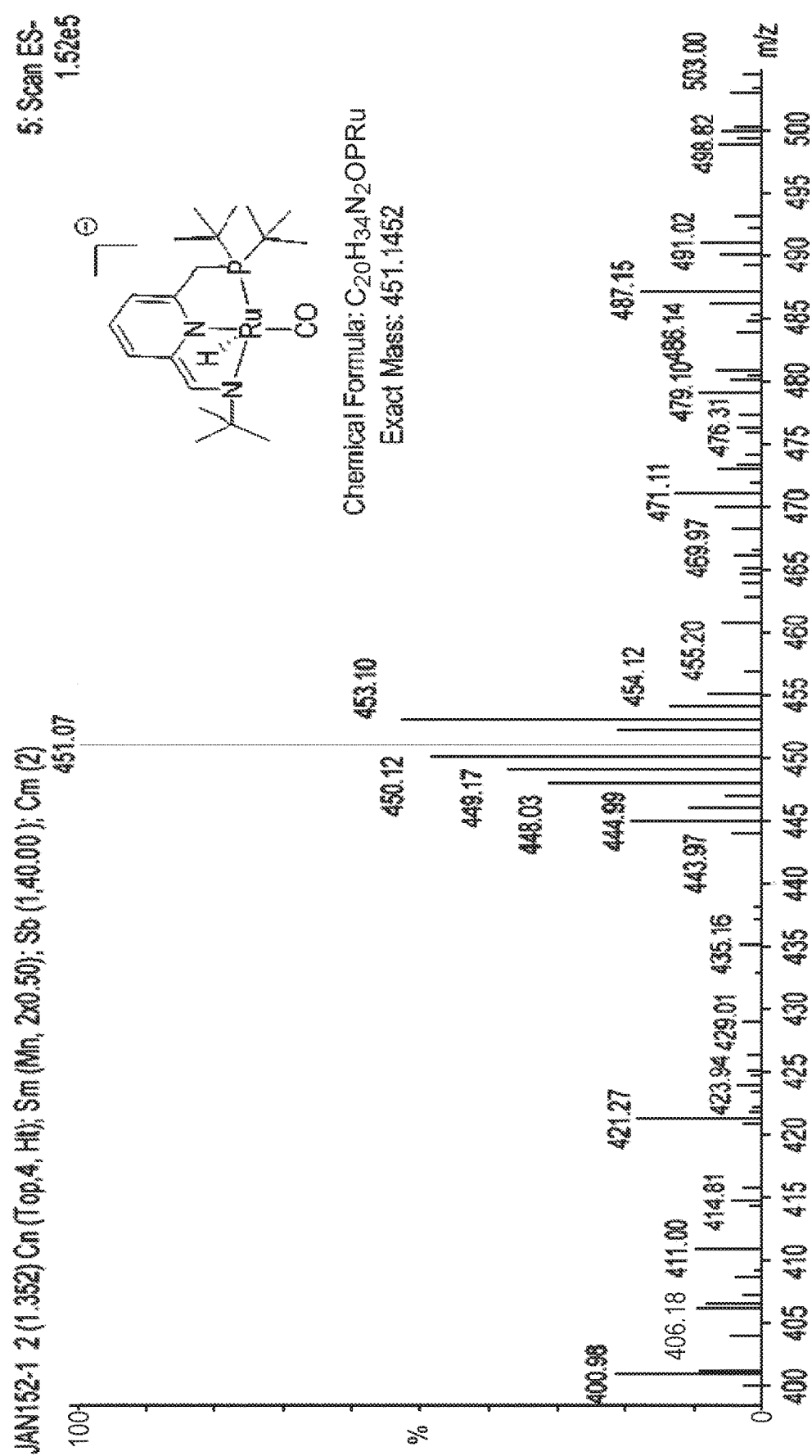
FIG. 4: ESI-MS of product obtained by reaction of complex 1 with 1.2 equiv. of KHMDS in THF at RT (i.e., complex 4 (cation=K$^+$)).

Addition of 1.2 equiv. of either potassium bis(trimethylsilyl)amide (KHMDS) or potassium tert-butoxide (KO$^t$Bu) to 1 in THF at RT leads to two signals at 98.0 ppm and 93.0 ppm in the $^{31}P\{^1H\}$ NMR spectrum with complete disappearance of the starting material. However, isolation of the products from the mixture was unsuccessful. It was observed that with time, upon standing, the intensity of both the signals in the reaction mixture decreased, leading to a violet precipitate from an initially brown solution. The same phenomenon was also seen with incremental addition of base from 0.5 equiv. to 2.2 equiv of base. Surprisingly, the resultant violet product thus obtained with either 1.1 or 2.2 equiv. was silent in both $^{31}P\{^1H\}$ NMR and $^1H$ NMR at RT. However, when 1 was reacted with 2.2 equiv. of KHMDS in a NMR tube at RT and then cooled to −40° C. stepwise, it showed a new broad signal at 124.0 ppm in the $^{31}P\{^1H\}$NMR spectrum with a corresponding hydride signal at −18.5 ppm in $^1H$ NMR (FIG. 3). This signal was tentatively assigned to the anionic complex resulting by deprotonation of both the amine and one of the methylene protons, even though the broadness of the signal precluded complete NMR characterization. Mass (ES$^-$) spectrum recorded for this air-sensitive violet product however matched with that of the expected anionic complex, supporting this assignment (FIG. 4). The structure assigned to this complex is represented below (i.e., complex 4 wherein cation=K$^+$).

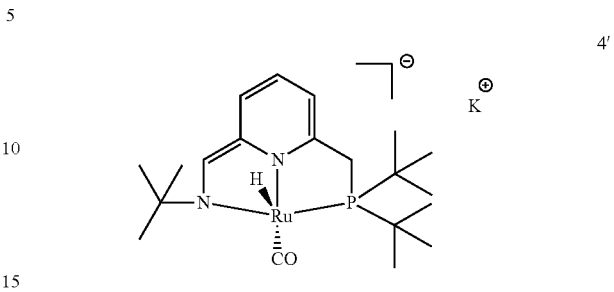

Figure 5:
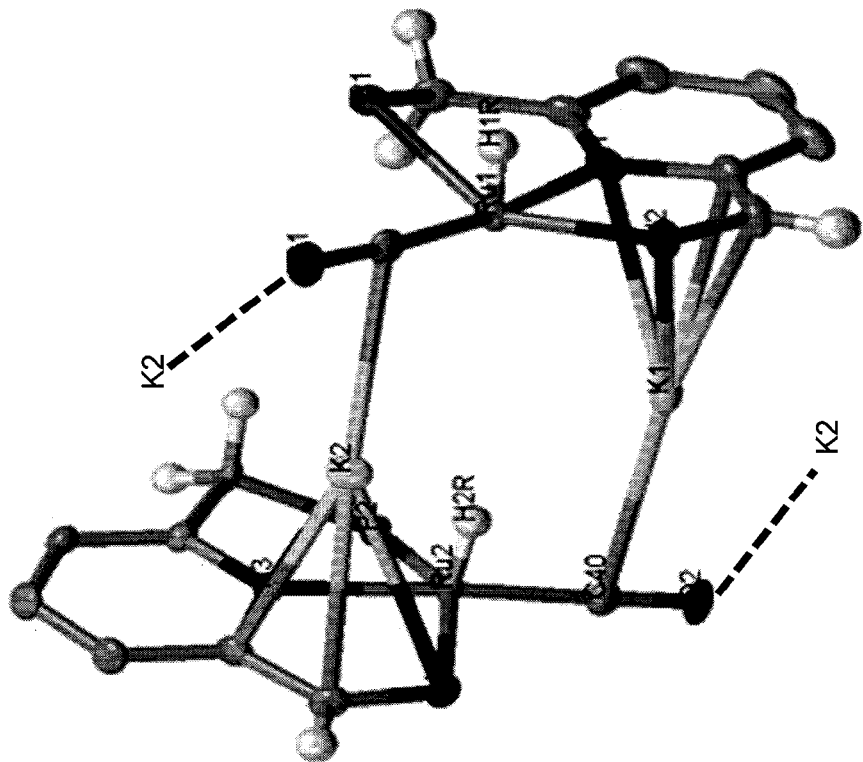
FIG. 5: shows the X-ray structure of Ruthenium complex 4 (cation=K$^+$) Selected hydrogen atoms and K$^+$ counter cation omitted for clarity. Right: Section of the unit cell showing the connection with K. Substituents on phosphorus and nitrogen are omitted for clarity. Selected bond distances (Å) and angles (°): Ru1-H1R 0.95(5); Ru2-H2R 1.00(4), Ru1-C20 1.816(4); Ru2-C40 1.827(4), Ru1-N1 2.061(3); Ru2-N4 2.069(3), Ru1-N2 2.063(3); Ru2-N3 2.059(3), Ru1-P1 2.2581(10); Ru2-P2 2.2623(10). N1-Ru1-H1R 82(3); N3-Ru2-H2R 98(2), N2-Ru1-H1R 89(2); N4-Ru2-H2R 107 (2), N2-Ru1-P1 145.71(10); N4-Ru2-P2 150.33(9), N1-Ru1-C20 173.26(15); N3-Ru2-C40 171.49(15).
Figure 5:
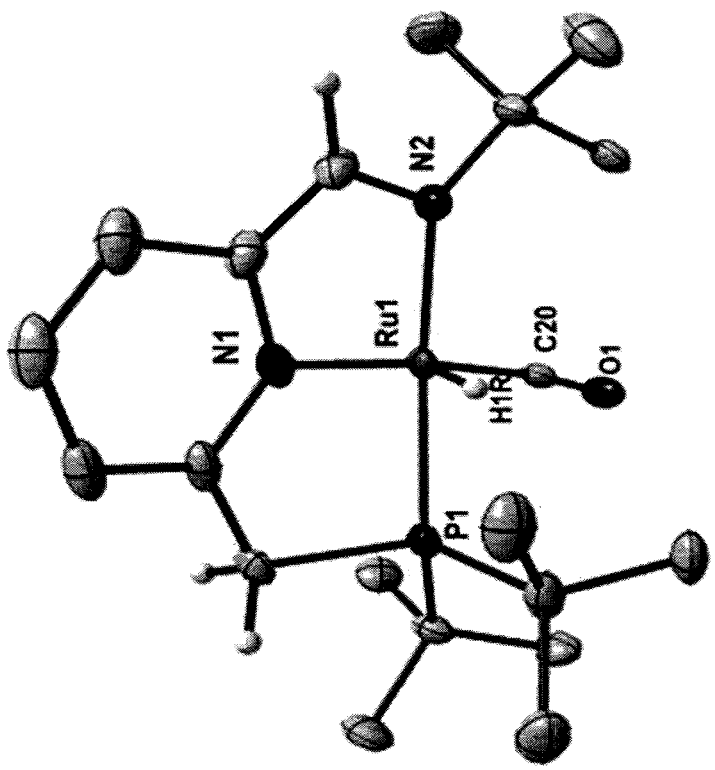

Violet crystals suitable for X-ray diffraction were obtained from a mixture of THF and ether. As expected, it revealed a double deprotonated enamido monoanionic complex with K$^+$ as counter cation, forming a distorted square-pyramidal geometry with the hydride located at the apical position (Ru1-H1R 0.95(5) Å). The perspective views of the complex are shown in FIG. 5. Contrary to the deprotonation of the P-arm methylene protons, as previously observed in the de-aromatized forms of RuPNN-$Et_2$, C..H deprotonation took place on the N-arm, as clearly indicated by the short $Csp^2$-$Csp^3$ bond distance of 1.371 Å of the N-arm and the presence of only one C..H bond. In addition, the absence of proton attached to nitrogen unequivocally indicates that overall double deprotonation took place. The other bond distances fall in the normally expected ranges. From the molecular packing, it appears that two successively independent Ru pincer molecules are disposed roughly at 120° to each other and are connected to each other by potassium ions, which bridge between the deprotonated amine arm and the carbonyl carbon.

A change of base was attempted. Reaction of 1 with KH (2.5 equiv.) in THF at RT resulted in the formation of the violet enamido anionic complex 4' within 18 h (Scheme 15):

Scheme 15. Preparation of the
monoanionic complex 4' by double deprotonation of 1

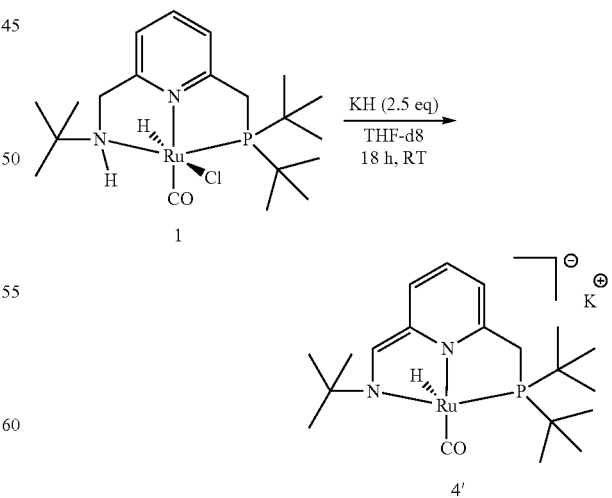

Figure 6:
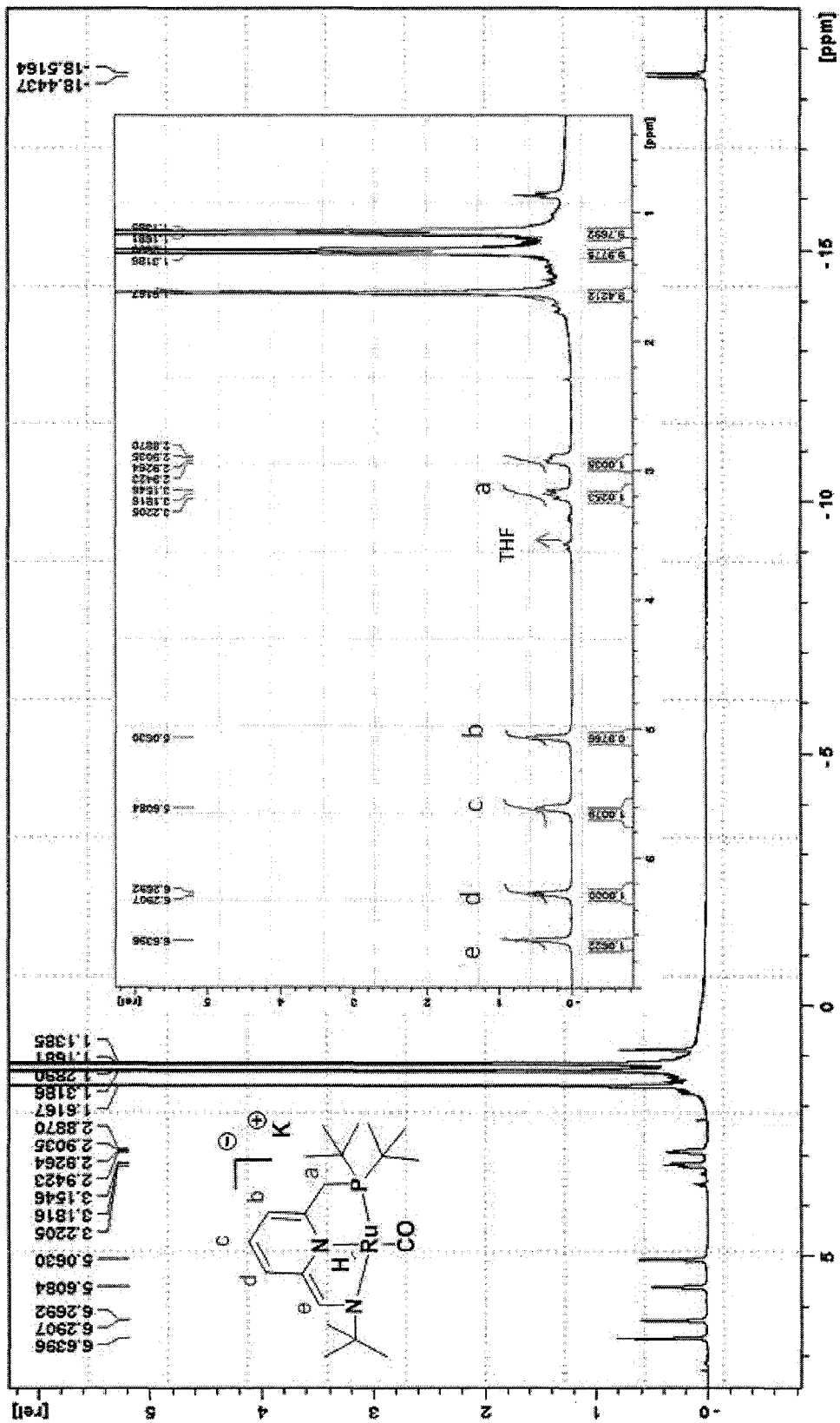
FIG. 6: $^1H$ NMR spectrum of Ruthenium complex 4 (cation=K$^+$) in THF-d8 after 18 h at RT.
Figure 7:
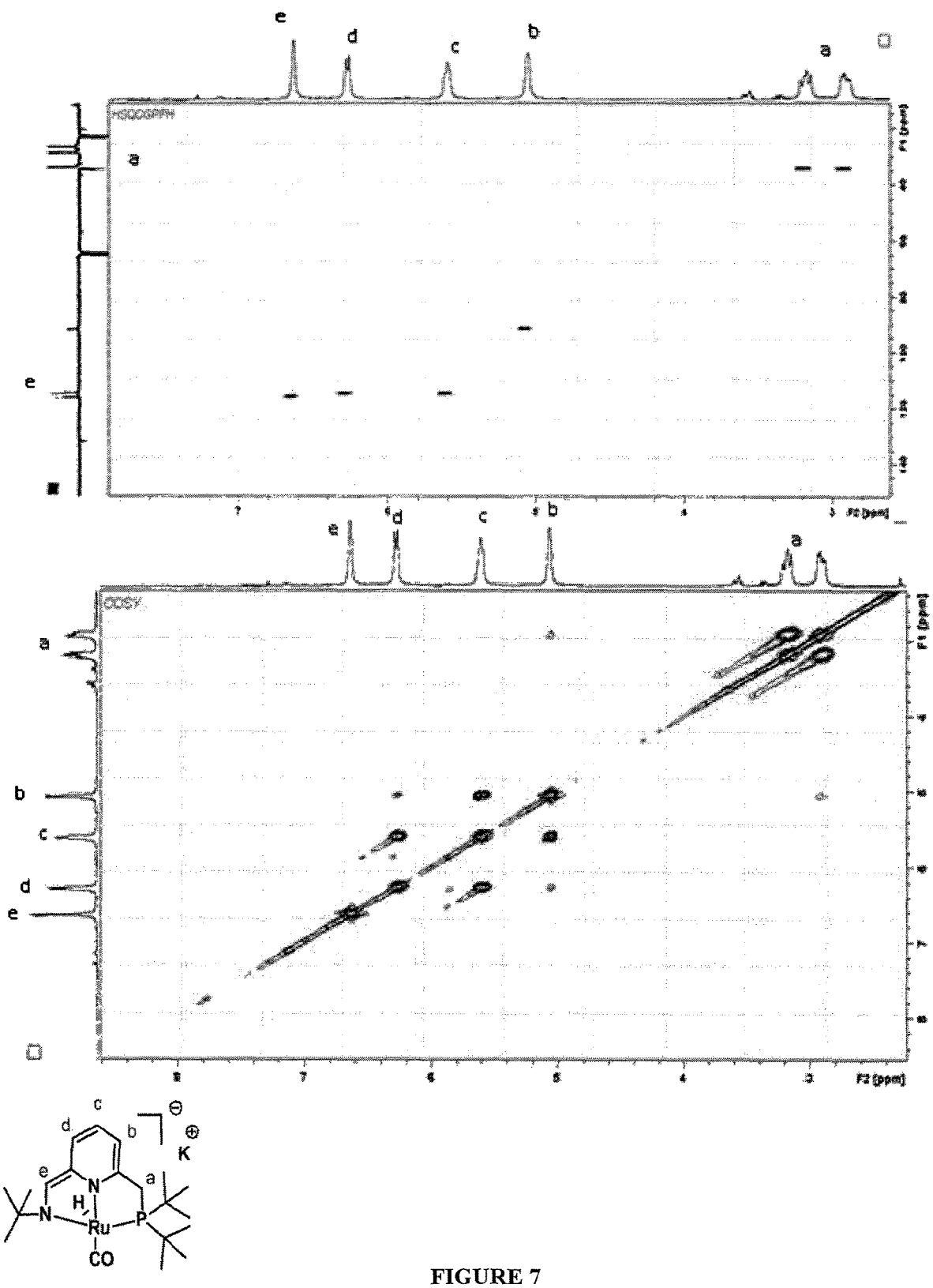
FIG. 7: Partial HSQC and COSY spectrum of 4 (cation=K$^+$) in THF-d8 after 18 h.

Monitoring the progress of the reaction at early intervals reveals the same set of intermediates namely the de-aromatized intermediate and the amido intermediate, finally leading to the violet precipitate, showing in the $^{31}$P NMR at 124.0 ppm and hydride at −18.5 ppm in the $^1$H NMR (FIG. 6). The $^1$H NMR reveals that the aromatic ring protons have shifted upheld (5.0-6.2 ppm) due to the de-aromatization. The enamino proton resonates most downfield at 6.6 ppm (FIG. 7).

Example 2

Preparation of Glycine Anhydride from 2-aminoethanol

Initially, 2-aminoethanol (AE) was heated at 135° C. under argon for 12 hours in the absence of solvent, using 0.05 mol % of (i) and 1.2 equiv of KO$^t$Bu (for generation of the actual catalyst (ii) in situ). No product was observed under these conditions (Table 1, entry 1), perhaps due to practically irreversible binding of the substrate to Ru via the amine group due to the high concentration of the substrate, retarding the required O—H activation. However, using 10 mmol of AE and 0.5 mol % of catalyst (i) with no solvent resulted in 48% conversion to mostly linear peptides, and 25% yield of H$_2$ (entry 2). Using 0.5 mL dioxane as a solvent and catalyst loading to 0.5 mol % resulted in 57% conversion of 2-aminoethanol to give linear peptides as the major products, as observed by $^1$H NMR spectroscopy and Mass Spectrometry (entry 3). Significantly, when 2 mL dioxane was used as a solvent and 0.5 mol % of catalyst (i) was employed, 68% conversion was observed, forming glycine anhydride (GA) in 31% yield, and linear peptides (entry 4). Increasing the volume of dioxane led to improvement in both the yield of glycine anhydride and the amount of linear products (entries 4-6). However, using more than 4 mL dioxane didn't improve the reaction (entries 10,)11. Testing the bipyridine-based PNN ruthenium pincer complexes (iii) and (iv) resulted in much lower conversion of 2-aminoethanol than with catalyst (i) (entries 7,8).

The PNN—H complex 1, bearing an N—H group, was tested for its ability to catalyze conversion of 2-aminoethanol to glycine anhydride (GA). It was hypothesized that the presence on an NH ligand might allow for metal-ligand cooperation (MLC) via the well-known Ru-amino/Ru-amido sequence, in addition to MLC via aromatization-dearomatization of the known pincer ligand. When 1.2 equiv of base was used, 2-aminoethanol was converted to GA and linear peptide (LP), however, yields were moderate (35% GA formation and a total conversion of 71%) (Table 1 entry 9). Increasing the amount of solvent (dioxane) considerably improved reaction yields (Table 1, entry 12). Interestingly, the amount of base had a strong influence on the outcome of the reaction in this case (Table 1, entries 13-16). With 0.5 mol % of 1 and 1.2 mol % of KOtBu (2.4 equiv base relative to catalyst 1) as the catalyst system, 85% conversion of 2-aminoethanol and 60% yield of glycine anhydride were gained (Table 1, entry 14). 37 mL H$_2$ gas were collected under the optimized reaction conditions, corresponding to 83% yield of hydrogen based on the reaction of Scheme 3. Higher base loading (Table 1, entries 15, 16) and lower temperature (Table 1, entries 16, 17) decreased the performance of the reaction. When applying catalyst (i) with increased base loading, lower conversion and yield of glycine anhydride were obtained (entry 6 vs 19). The dehydrogenation reaction was also performed in a large scale of 20 mmol under the conditions of entry 14, of which give similar results, namely 89% conversion of AE, 55% yield of GA and 74% of H$_2$ (710 ml; entry 20).

TABLE 1

Selected results of optimization studies for dehydrogenation of 2-aminoethanol

| entry | catalyst | KO$^t$Bu (equiv to Cat.) | dioxane (mL) | conversion (%) | product$^a$ (yield %) |
|---|---|---|---|---|---|
| 1$^{b,c}$ | (i) | 1.2 | — | — | — |
| 2$^b$ | (i) | 1.2 | 0 | 48 | GA (trace) + LP |
| 3$^d$ | (i) | 1.2 | 0.5 | 57 | GA (trace) + LP |
| 4 | (i) | 1.2 | 2 | 68 | GA (31) + LP |
| 5 | (i) | 1.2 | 3 | 72 | GA (35) + LP |
| 6 | (i) | 1.2 | 4 | 78 | GA (48) + LP |
| 7 | (iii) | 1.2 | 4 | 55 | GA (32) + LP |
| 8 | (iv) | 1.2 | 4 | 32 | GA (1) + LP |
| 9 | 1 | 1.2 | 4 | 71 | GA (35) + LP |
| 10 | (i) | 1.2 | 5 | 81 | GA (53) + LP |
| 11$^e$ | (i) | 1.2 | 6 | 83 | GA (52) + LP |
| 12$^e$ | 1 | 1.2 | 6 | 87 | GA (61) + LP |
| 13 | 1 | 1.8 | 4 | 72 | GA (47) + LP |
| 14 | 1 | 2.4 | 4 | 85 (83)$^f$ | GA (60) + LP |
| 15 | 1 | 4 | 4 | 85 | GA (37) + LP |
| 16 | 1 | 6 | 4 | 88 | GA (34) + LP |
| 17$^g$ | 1 | 2.4 | 4 | 78 | GA (41) + LP |
| 18$^h$ | 1 | 2.4 | 4 | 84 | GA (53) + LP |
| 19 | (i) | 2.4 | 4 | 70 | GA (33) + LP |
| 20$^i$ | 1 | 2.4 | 80 | 89 (74) | GA (55) + LP |

Reaction conditions: 0.5 mol % catalyst, KO$^t$Bu (as specified in the Table), 1 mmol 2-aminoethanol and solvent were refluxed (the actual reaction temperature was 105° C. when using dioxane as the solvent, oil bath temperature 135° C.) under a flow of argon for 12 h. Conversion determined by NMR using 1,3,5-trimethylbenzene as an internal standard. Yields determined by NMR using pyridine as an internal standard.
$^a$GA, glycine anhydride; LP, linear peptides.
$^b$10 mmol of 2-aminoethanol was used.
$^c$0.05 mol % catalyst was used.
$^d$5 mmol 2-aminoethanol was used.
$^e$0.75 mol % catalyst was used.
$^f$H$_2$ was collected, values in parentheses are yields of hydrogen based on the reaction of eq S1(Scheme 3).
$^g$oil bath temperature 105° C.
$^h$oil bath temperature 115° C.
$^i$20 mmol of 2-aminoethanol was used.

Scheme 16

HO\~\~NH$_2$ (AE) →[catalyst] GA + LP + H$_2$

The individual reactions leading to GA and LP are provided below:

(S1)

2 HO\~\~NH$_2$ →[catalyst] GA + 4 H$_2$ (S2)

(n + 1) HO\~\~NH$_2$ →[catalyst]

-continued

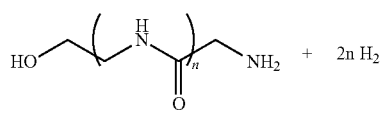 + 2n H$_2$

Solvent mixtures of dioxane with other polar or non-polar solvents, including diglyme, DMF (dimethylformamide), valeronitrile, DMAC (dimethylacetamide), NMM (N-methylmorpholine) and toluene, were also tried, generally resulted in lower efficiency, although the reactions were still feasible using these conditions (Table 2).

TABLE 2

Solvent optimization for dehydrogenation of 2-aminoethanol using complex (i).

| entry | solvent (mL) | conversion (%) | product (yield %) |
|---|---|---|---|
| 1 | dioxane (4) | 78 | GA (48) + LP |
| 2 | pyridine (4) | 50 | GA (trace) + LP |
| 3 | diglyme (3), dioxane (1) | 20 | — |
| 4 | toluene (3), dioxane (1) | 75 | GA (33) + LP |
| 5 | toluene (3.5), dioxane (0.5) | 62 | GA (21) + LP |
| 6 | DMF (3), dioxane (1) | — | — |
| 7 | n-BuCN (3), dioxane (1) | 58 | GA (10) + LP |
| 8 | DMAc (3), dioxane (1) | — | — |
| 9 | NMM (3), dioxane (1) | 34 | GA (18) + LP |
| 10 | NMM (0.5), dioxane (3.5) | 61 | GA (27) + LP |
| 11 | NMM (1), dioxane (3) | 67 | GA (29) + LP |

Reaction conditions: 0.5 mol % catalyst (i), 1.2 equiv of KO$^t$Bu to catalyst (i), 1 mmol 2-aminoethanol and solvent were refluxed (the actual reaction temperature was 105° C. when using dioxane as the solvent, oil bath temperature 135° C.) under a flow of argon for 12 h. Conversion determined by NMR using 1,3,5-trimethylbenzene as an internal standard. Yields determined by NMR using pyridine as an internal standard.
GA, glycine anhydride; LP, linear peptides; DMF, Dimethylformamide; DMAc, Dimethylacetamide; NMM, 4-methylmorphline.

Using no solvent or a very small amount of solvent resulted in lower efficiency of the dehydrogenative coupling reaction, although substantial dehydrogenation was still observed (Table 3). When applying 0.5 mol % catalyst (i) and 0.6 mol % KO$^t$Bu in neat 2-aminoethanol at 135° C. for 12 h, 48% conversion was achieved. However, just 27% yield of hydrogen gas was collected, together with 2-amino-N-(2-hydroxyethyl)acetamide (AA) and some other short-chain linear peptides (n=2, 3) as the major products (entry 1). Refluxing 2-aminoethanol under mild vacuum (~80 mm Hg) at 110-124° C. resulted in similar conversion (entry 2). DMSO was found to be a helpful additive for the reaction (entries 3-8). A small amount of DMSO (0.1 mL DMSO per 10 mmol 2-aminoethanol) improved the yield of H$_2$ from 27% to 35% at 135° C. (entry 1 vs 3). Catalyst 1 gave similar results as compared to catalyst (i) under the same conditions (entry 3 vs 6). Higher temperature slightly increased the outcome of the reaction (entries 7, 8) and 42% yield of H$_2$ was obtained when heating the reaction to 170° C. for 12 h (entry 8). 0.5 mL of dioxane, anisole and mixture of anisole/DMSO (4:1 in volume) had similar effects on the reaction and approximate 30% yield of H$_2$ was produced (entries 9-11). When 0.5 mL DMSO was used solely as the solvent, H$_2$ was obtained in just 24% yield (entry 12).

TABLE 3

Dehydrogenation of 2-aminoethanol using a small amount of solvent

| entry | solvent (mL) | conversion (%) | product (yield) |
|---|---|---|---|
| 1 | — | 48 (27)$^a$ | GA (trace) + LP |
| 2$^b$ | — | 46 | GA (trace) + LP |
| 3 | DMSO (0.1) | 61 (35)$^a$ | GA (trace) + LP |
| 4 | DMSO (0.05) | 59 (32)$^a$ | GA (trace) + LP |
| 5 | DMSO (0.15) | 63 (33)$^a$ | GA (trace) + LP |
| 6$^c$ | DMSO (0.1) | 60 (33)$^a$ | GA (trace) + LP |
| 7$^d$ | DMSO (0.1) | 67 (38)$^a$ | GA (trace) + LP |
| 8$^e$ | DMSO (0.1) | 71 (42)$^a$ | GA (trace) + LP |
| 9$^f$ | dioxane (0.5) | 57 (31)$^a$ | GA (trace) + LP |
| 10$^f$ | anisole (0.5) | 62 (33)$^a$ | GA (trace) + LP |
| 11$^f$ | anisole (0.4) DMSO (0.1) | 62 (34)$^a$ | GA (trace) + LP |
| 12$^f$ | DMSO (0.5) | 42 (24)$^a$ | GA (trace) + LP |

Reaction conditions: 0.5 mol % catalyst (i), 1.2 equiv(to catalyst (i)) of KO$^t$Bu, 10 mmol 2-aminoethanol and solvent were heated (oil bath temperature 135° C.) under a flow of argon for 12 h. Conversion and yields were determined by NMR using pyridine as an internal standard.
$^a$H$_2$ was collected, values in parentheses were yields of hydrogen based on the reaction of eq S1 (assuming 100% conversion to glycine anhydride).
$^b$Reflux under vacuum for 24 h, boiling point 110-124° C., oil bath temperature 125° C.
$^c$0.5 mol % catalyst 1, 1.2 mol % KO$^t$Bu were used.
$^d$oil bath temperature 150° C.
$^e$oil bath temperature 170° C.
$^f$5 mmol of 2-aminoethanol was used.
GA, glycine anhydride; LP, linear peptides; DMSO, dimethyl sulfoxide.

Example 3

Hydrogenation of Glycine Anhydride to 2-Aminoethanol

Catalysts (i) and 1 were tested for the hydrogenation of glycine anhydride which is unprecedented for any diketopiperazine. At first, no product was obtained when the reaction was run under 10 bar of H$_2$ in THF using 1 mol % of either complex at 110° C. (oil bath temperature, Table 4, entries 1, 2). Applying 50 bar of H$_2$, 2 mol % complex (i) and 2.4 mol % KO$^t$Bu in dioxane at 110° C. resulted in quantitative yield of the linear amide 2-amino-N-(2-hydroxyethyl)acetamide (entry 3). Higher amount of base improved the reaction, with 61% yield of glycine anhydride and 34% yield of 2-amino-N-(2-hydroxyethyl)acetamide were produced when 4.8 mol % KO$^t$Bu was applied together with 2 mol % complex (i) (entry 4). Complex 1 showed much better catalytic activity than complex (i) and nearly 100% yield of 2-aminoethanol was obtained, even in a lower complex loading of 0.5 mol % and less amount of solvent (entries 5, 6). Using lower pressure of H$_2$ (20 bar) was less effective to afford 2-aminoethanol from glycine anhydride (entry 7). The mixed products of glycine anhydride and linear peptides produced by the dehydrogenative reaction (under conditions of Table 4, entry 13) could also be hydrogenated by complex 1 and 85 wt % yield was obtained under 50 bar of H$_2$ (entry 8). Higher pressure of H$_2$ failed to improve the yield (entry 9), probably because of the poor solubility of the long-chain linear peptides.

TABLE 4

Selected results from the optimization studies for hydrogenation of glycine anhydride

| entry | complex (mmol) | KO$^t$Bu (equiv to complex) | t (h) | substrate$^a$ (mmol) | H$_2$ pressure (bar) | solvent (mL) | Product$^b$ (yield %) |
|---|---|---|---|---|---|---|---|
| 1$^c$ | (i) (0.005) | 1.2 | 24 | GA (0.5) | 10 | THF (4) | — |
| 2$^c$ | 1 (0.005) | 2.4 | 24 | GA (0.5) | 10 | THF (4) | — |
| 3 | (i) (0.01) | 1.2 | 48 | GA (0.5) | 50 | dioxane (4) | AA (>99) |
| 4 | (i) (0.01) | 2.4 | 48 | GA (0.5) | 50 | dioxane (4) | AE (61), AA |
| 5 | 1 (0.005) | 2.4 | 48 | GA (0.5) | 50 | dioxane (4) | AE (>99) |
| 6 | 1 (0.005) | 2.4 | 48 | GA (1) | 50 | THF (2) | AE (>99) |
| 7 | 1 (0.005) | 2.4 | 48 | GA (1) | 20 | THF (2) | AA (23) |
| 8 | 1 (0.0025) | 2.4 | 48 | mixture$^d$ | 50 | dioxane (1) | AE (85)$^e$ |
| 9 | 1 (0.0025) | 2.4 | 48 | mixture$^d$ | 70 | dioxane (1) | AE (86)$^e$ |
| 10 | 1 (0.05) | 2.4 | 12 | GA (5) | 70 | Dioxane (5) | AE (96), AA (4) |

Reaction conditions: complex, KO$^t$Bu, glycine anhydride, solvent and H$_2$ were heated in a 20 mL Parr apparatus at 110° C. (oil bath temperature). Yields determined by NMR using pyridine as an internal standard.
$^a$GA, glycine anhydride.
$^b$AA, 2-amino-N-(2-hydroxyethyl)acetamide; AE, 2-aminoethanol.
$^c$100 mL Fischer-Porter tube was used.
$^d$28.6 mg mixture of GA and linear peptides (produced from AE under the conditions of Table 4, entry 6) was used as substrate.
$^e$wt %.

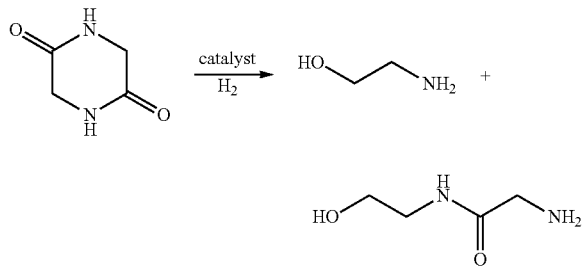

Scheme 17

Example 4

Repetitive Reversal Reactions

TABLE 5

Repetitive cycles of the dehydrogenation hydrogenation reactions

| Cycle | Conversion of dehydrogenation* | Conversion of hydrogenation* |
|---|---|---|
| 1 | 86 | 97 (97) |
| 2 | 79 (81) | 90 (87) |
| 3 | 76 (84) | 81 (75) |

*Based on the amount of 2-aminoethanol in the system. The number in parenthesis is based on the product of the former step.

Repetitive cycles of the dehydrogenation-hydrogenation reactions were also tried without adding new catalyst (Table 5, see below for procedure details). The cycles began with dehydrogenation, using 1 mol % catalyst 1, 2.4 mol % KOtBu, 1 mmol 2-AE and 4.5 ml dioxane (for an example of applying 0.5 mol % catalyst, see below for more details). A catalytic amount of KO$^t$Bu (2.4 equiv. relative to complex 1) was added every time after the former reaction, to protect the catalyst from trace amount of water, which may be taken into the system during the course of transfer (catalysed by PNN ruthenium pincer complexes, water and alcohol can produce a carboxylic acid, which can poison the catalyst in the absence of base). After the first dehydrogenation reaction, of which 86% conversion of AE was achieved, the crude reaction mixture was transferred to a 20-ml Parr apparatus under N$_2$ atmosphere. The Parr apparatus was then filled with H$_2$ and the hydrogenation reaction was performed. Without isolation, the catalytic activity of the system was higher as compared with Table 4, entry 9 and 97% of AE (based on the amount of AE used in the first dehydrogenation reaction) was observed. Following this, the second dehydrogenation step resulted in 79% conversion of AE, while the second hydrogenation step provided 90% of AE. The results of the third cycle were also good, even after using the catalyst for six times, 81% of AE was still observed at the end of the third hydrogenation step.

Example 5

Mechanistic Studies

To gain mechanistic understanding of the dehydrogenative peptidation reaction, the reactivity of the dearomatized complex (ii) was studied by NMR spectroscopy. Addition of 1.5 equiv of 2-aminoethanol to a C$_6$D$_6$ solution of complex (ii) at room temperature (r.t.) rapidly afforded nearly quantitatively the aromatic alkoxo species 6, which exhibited a hydride as a doublet at −14.22 ppm (J$_{PH}$=18.9 Hz) in the $^1$H NMR spectrum and a singlet at ~106 ppm in the $^{31}$P{$^1$H} NMR spectrum. The signals of the two protons of the NH$_2$ group appear at very different chemical shifts in the $^1$H NMR spectrum (4.58 ppm and 2.83 ppm) [Abdur-Rashid, K. et al., *J. Am. Chem. Soc.* 123, 7473-7474 (2001)], while the two methyl groups of the NEt$_2$ group exhibit a single triplet (6H, 0.86 ppm, $J_{HH}$=7.1 Hz); both these observations indicate coordination of the $NH_2$ group to the Ru center and decoordination of the $NEt_2$ "arm". Complex 6 was stable below −30° C. and slowly transformed at r.t. to the trans-dihydride complex 7 previously reported [Zhang, J., Leitus, et al. *J. Am. Chem. Soc.* 127, 10840-10841 (2005)] and a new species which featured a singlet at ~102 ppm in the $^{31}P\{^1H\}$ NMR spectrum and a hydride signal at −13.16 ppm (d, $J_{PH}$=23.2 Hz) in the $^1H$ NMR spectrum (FIG. 8*a*).

Crystals of this compound were obtained after two weeks of slow diffusion of pentane into a concentrated benzene solution of complex 6. The single crystal X-ray structure of the new complex 8 (FIG. 9) indicates a distorted octahedral geometry around the Ru(II) center, with the phosphorus atom coordinated trans to the nitrogen atom of the amide group and the hydride trans to the nitrogen atom of the $NH_2$ group. The two nitrogen atoms of N—C—C—N backbone coordinate to the Ru(II) center in a chelating manner, forming a five-membered ring. The relative C—C bond lengths (for example, C(1)-C(2) 1.506(4) Å, C(6)-C(7) 1.510(4) Å) indicate that complex 8 is an aromatized complex (FIG. 9), which is consistent with the corresponding NMR data. The amide backbone was surely produced through intermolecular dehydrogenative coupling of two molecules of 2-aminoethanol, illustrating highly selective generation of an amide rather than an ester from 2-aminoethanol. This was further proven by an NMR study of the reaction of catalyst (ii) with 10 equiv of 2-aminoethanol at r.t., as shown in FIG. 8*c*. Complexes 6 and 8 were the major species observed, and after 10 days at room temperature complex 8 was the major product. The trans-dihydride complex 7 is likely formed by a β-H elimination process of complex 6, based on the NMR results and the known chemistry of PNN-type ruthenium pincer complexes (Scheme 18)[Gunanathan, C. & Milstein, D. et al. *Acc. Chem. Res.* 44, 588-602 (2011); Zhang, J., et al. *J. Am. Chem. Soc.* 127, 10840-10841 (2005); Gunanathan, C., et al. *Science* 317, 790-792 (2007); Ganaprakasam, B., et al. *Chem., Int. Ed.* 50, 12240-12244 (2011); Balaraman, E., et al *J. Am. Chem. Soc.* 132, 16756-16758 (2010)]. Compared with reaction of complex (ii) with 1.5 equiv of 2-aminoethanol (FIG. 8*b*), the trans-dihydride complex 7 was nearly fully consumed when 10 equiv of 2-aminoethanol were used, indicating that the dehydrogenation course from complex 7 to the dearomatized complex (ii) is accelerated by excess of 2-aminoethanol, which reacts with (ii) to give complex 8, hence shifting the equilibrium between 7 and (ii). Complex 8 was also independently prepared by reaction of complex (ii) with 2-amino-N-(2-hydroxyethyl)acetamide (see Example 8).

Scheme 18: Observed path from complex (ii) to complex 8.

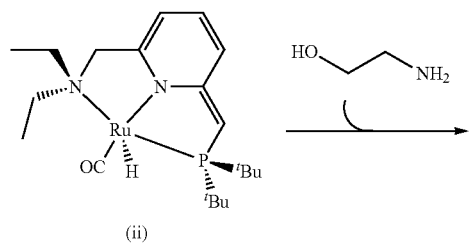

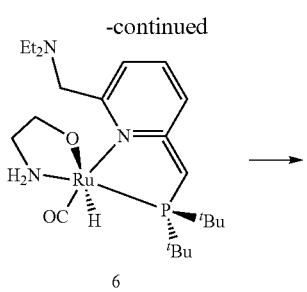

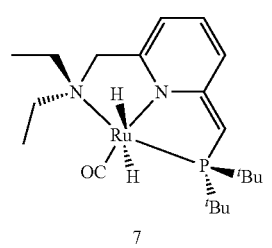

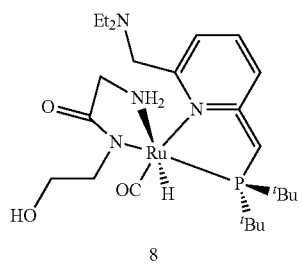

Figure 11:
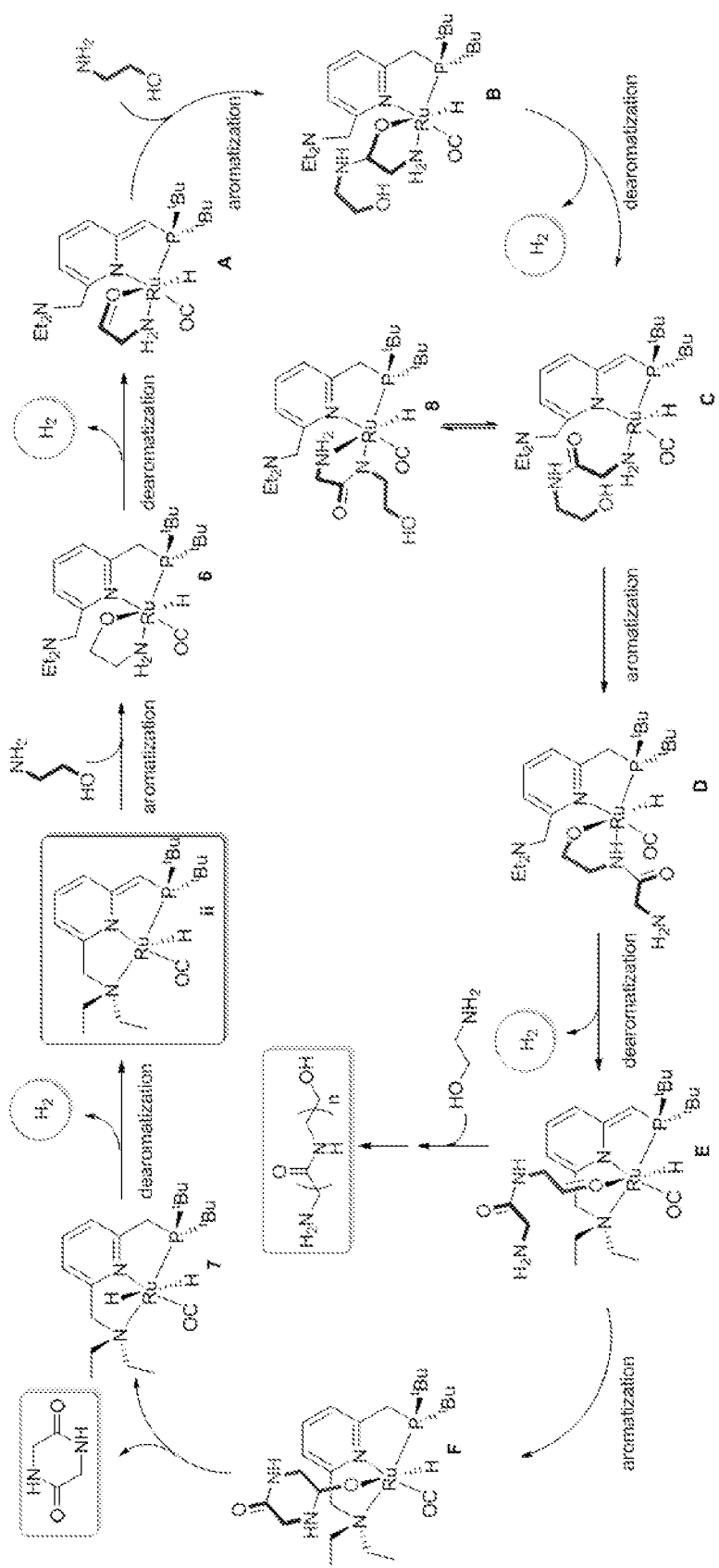
FIG. 11: Proposed mechanism for dehydrogenative coupling of AE catalyzed by complex (ii).

On the basis of the NMR studies, the isolation of complex 8, and the known chemistry of pyridine-based pincer ruthenium complexes, the mechanism shown in FIG. 11 is proposed. Reaction of the dearomatized complex (ii) with AE leads to the aromatic alkoxy complex 6. Following dehydrogenation by metal-ligand cooperation, the 2-amino aldehyde intermediate A is formed and then attacked by another molecule of AE, providing the aromatic hemiaminoxy intermediate B. Subsequent hydride elimination and $H_2$ generation affords the dearomatized AA intermediate C. Isomerization of C and activation of the O—H bond produces the aromatic species D, followed by hydride elimination to generate an aldehyde group and release a third molecule of $H_2$ to afford intermediate E. Intramolecular reaction between the amino and aldehyde groups in complex E produces GA via intermediate F, while an intermolecular reaction with AE results in a linear oligopeptide. During formation of D from intermediate C, isomerization followed by amide N—H activation produces complex 8.

Example 6

Dehydrogenation of 2-(methylamino)ethanol 2-(methylamino)ethanol was reacted with Ruthenium complexes as detailed in Table 6:

Scheme 19. Dehydrogenation of 2-(methylamino)ethanol to N,N-dimethyl GA

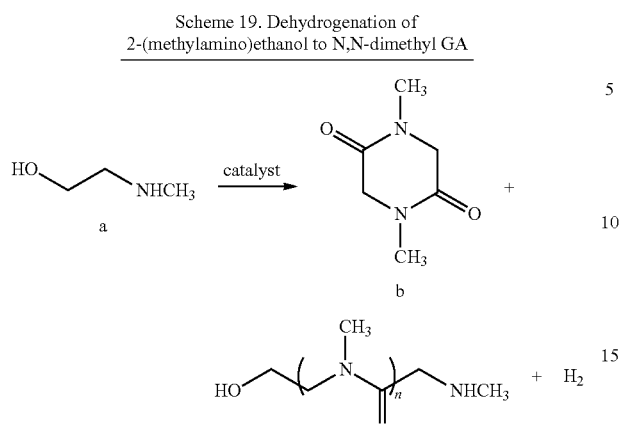

TABLE 6

| entry | catalyst (mol %) | a (mmol) | KO$^t$Bu (equiv to Cat.) | dioxane (mL) | conversion (%) | yield of b (%) |
|---|---|---|---|---|---|---|
| 1 | A (0.25) | 2 | 1.2 | 0.5 | >99 | >99 |
| 2 | A (0.25) | 2 | 1.2 | 2 | >99 | >99 |
| 3 | A (0.1) | 5 | 1.2 | 0.5 | 80 | 27 |
| 4 | A (0.1) | 10 | 1.2 | — | 53 | 9 |
| 5 | B (0.1) | 5 | 1.2 | 0.5 | 78 | 26 |
| 6 | H (0.1) | 5 | 2.4 | 0.5 | 77 | 27 |
| 7 | A (0.1) | 5 | 1.2 | 1 | 80 | 34 |
| 8 | A (0.1) | 8 | 1.2 | 1 | 75 | 28 |
| 9 | C (0.1) | 5 | 1.2 | 1 | 38 | 17 |
| 10 | C (0.2) | 5 | 1.2 | 1 | 57 | 44 |
| 11 | B (0.25) | 2 | 1.2 | 0.5 | >90 | 78 |
| 12 | H (0.25) | 2 | 2.4 | 0.5 | >99 | >99 |
| 13[a] | A (0.1) | 5 | 1.2 | 0.5 | 96 | 25 |
| 14[a] | A (0.1) | 5 | 1.2 | 1 | >99 | 36 |

Reaction conditions: catalyst, KO$^t$Bu (as specified in the Table), N-methylaminoethanol (as specified in the Table) and solvent were refluxed (oil bath temperature 135° C.) under argon for 24 h. Conversion and Yields determined by NMR using pyridine as an internal standard. Linear peptides were formed except entries 1, 2 and 12.
[a] reflux for 48 h.

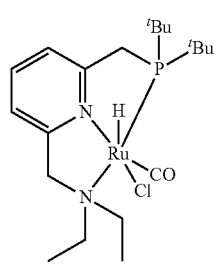

Cat. A

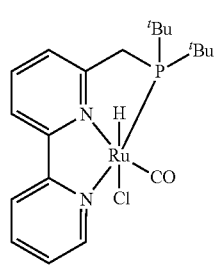

Cat. B

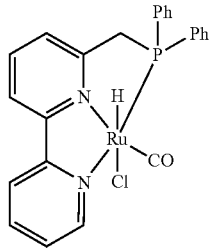

Cat. C

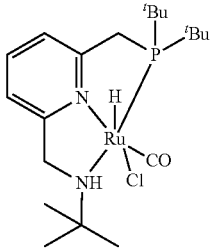

Cat. H

Example 7

Typical Procedure for the Dehydrogenation of 2-(methylamino)ethanol

In a glove box, a 25 mL Schlenk flask was charged with a stirring bar, catalyst (0.005 mmol), KO$^t$Bu (0.006-0.012 mmol), 2-(methylamino)ethanol (2 mmol) and dioxane (0.5 mL) under an atmosphere of nitrogen. The flask was taken out of the glove box, equipped with a condenser and the solution was refluxed with stirring in an open system under a flow of argon for 24 h. After cooling to room temperature, 1 mmol of pyridine was added to the crude reaction mixture as an internal standard. Then approximate 0.05 mL of the solution was dissolved in approximate 0.5 mL D$_2$O for determination of the conversion of N-methylaminoethanol and the yield of 1,4-dimethylpiperazine-2,5-dione by $^1$H NMR spectroscopy.

Example 8

Synthesis of Ruthenium Complexes and General Experimental Protocols

General Procedures:

All experiments with metal complexes and phosphine ligands were carried out under an atmosphere of purified nitrogen in a Vacuum Atmospheres glove box equipped with a MO 40-2 inert gas purifier or using standard Schlenk techniques. All solvents were reagent grade or better. All non-deuterated solvents were purified according to standard procedures under argon atmosphere. Deuterated solvents were used as received. All solvents were degassed with argon and kept in the glove box over 4 Å molecular sieves. Most of the chemicals used in the catalytic reactions were purified according to standard procedures (vaccum distillation). [Armarego, W. L. F. & Perrin, D. D. *Purification of Laboratory Chemicals* (Pergamon Press, Oxford, 1988) ed 3.] Complexes (i)-(iv) were prepared by our reported methods.[a] J. Zhang, et al., *J. Am. Chem. Soc.* 2005, 127, 10840-10841. b) Gunanathan, C.; Milstein, D. *Angew. Chem. Int. Ed.* 2008, 47, 8661-8664. c) Balaraman, E. et al. *J. Am. Chem. Soc.* 2010, 132, 16756-16758. d) Srimani, D.

et al. *Adv. Synth. Catal* 2013, 355, 2525-2530] RuHCl(PPh₃)₃(CO) [Ahmad, N.; et al. *Inorganic Syntheses*; John Wiley & Sons, Inc.: 2007, p 45-64.], 2-(ClCH₂-)-6-($^t$Bu₂P(BH₃)CH₂-)pyridine [Gargir, M.; et al. *Organometallics* 2012, 31, 6207-6214] were prepared according to literature procedures. $^1$H, $^{13}$C and $^{31}$P NMR spectra were recorded at 400, 100, and 162 MHz, respectively, using a Bruker AMX-400 NMR spectrometer. Measurements were done at various temperatures, as noted for each experiment. $^1$H NMR chemical shifts are referenced to the residual hydrogen signals of the deuterated solvent, and the $^{13}$C NMR chemical shifts are referenced to the $^{13}$C signals of the deuterated solvent. $^{31}$P NMR chemical shifts are reported in ppm relative to H₃PO₄ and referenced to an external 85% solution of phosphoric acid in D₂O. Abbreviations used in the description of NMR data are as follows: Ph, phenyl; Py, pyridyl; br, broad; s, singlet; d, doublet; t, triplet; m, multiplet; v, virtual; bm, broad multiplet; bs, broad singlet. IR spectra were recorded on a Nicolet FT-IR spectrophotometer. Mass spectra were recorded on MicromassPlatform LCZ 4000.

General Method for the Syntheses of PNNH Ligands (L1-L3)

A solution of 2-((BH₃)($^t$Bu₂)PCH₂-)-6-((ClCH₂-)pyridine (1.0 g, 3.34 mmol) in excess of the respective amine (15.0 mL) was heated at 100° C. for 12 h in a J. Young Schlenk tube. It was then cooled to RT, evacuated under vacuum and refilled with N₂ and heating at 100° C. was continued for an additional 30 min. Excess solvent was then distilled out under high vacuum and the residue was extracted with pentane. The pentane solution was filtered through Celite and concentrated in vacuo to yield the corresponding BH₃-deprotected phosphine and amine substituted ligands as viscous pale yellow oils which solidified in the freezer (−30° C.).

Ligand 1: N-((6-((di-tert-butylphosphanyl)methyl)pyridin-2-yl)methyl)-2-methylpropan2-amine (L1)

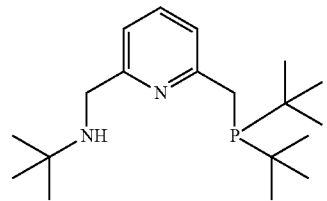

A solution of 2-(ClCH₂-)-6-($^t$Bu₂P(BH₃)CH₂-)pyridine (2 g, 6.67 mmol) in tert-butylamine (25 mL) was placed in a 100° C. oil bath overnight, then it was placed under vacuum for 1 min, purged with N₂ and placed again in the oil bath for 30 min. The solvent was removed under vacuum and the residue was extracted with pentane. The solution was filtered through Celite and the solvent was removed under vacuum to yield pure 2-(($^t$Bu₂)PCH₂-)-6-(($^t$Bu)NHCH₂-)pyridine (C₁₉H₃₅N₂P) as a white oil in 97% yield. $^{31}$P{$^1$H} NMR (CDCl₃): 36.5 (s).

$^1$H NMR (CDCl₃): 7.50 (t, $J_{H,H}$=7.6 Hz, 1H, Py-H4), 7.27 (d, $J_{H,H}$=7.6 Hz, 1H, Py-H5), 7.09 (d, $J_{H,H}$=7.6 Hz, 1H, Py-H3), 3.83 (bd, $J_{H,H}$=5.1 Hz, 2H, NHCH₂Py), 3.04 (d, $J_{H,P}$=3.6 Hz, 2H, PCH₂Py), 1.64 (bs, 1H, NH(CH₃)₃), 1.17 (bs, 18H, PC(CH₃)₃), 1.63 (bs, 9H, NH(CH₃)₃); $^{13}$C{$^1$H} NMR (CDCl₃): 161.2 (m, Py-C2, C6) 136.5 (s, Py-C4), 121.8 (d, $J_{C,P}$=10.0 Hz, Py-C3), 118.8 (bm, Py-C5), 48.6 (s, NHCH₂Py), 48.5 (s, NC(CH₃)₃), 31.9 (d, $J_{C,P}$=21.6 Hz, PC(CH₃)₃), 31.5 (d, $J_{C,P}$=23.8 Hz, PCH₂Py), 29.7 (d, $J_{C,P}$=13.0 Hz, PC(CH₃)₃), 29.2 (bs, NHC(CH₃)₃); HRMS: m/z 323.2619 (MH⁺, calcd. m/z 323.2616).

Ligand 2: N-((6-((di-tert-butylphosphanyl)methyl)pyridin-2-yl)methyl)propan-2-amine (L2)

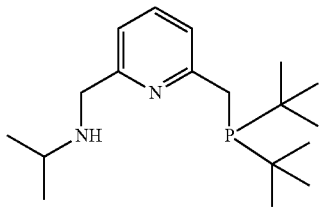

The general method above was employed.

Yield: 80%, $^{31}$P{$^1$H} NMR (CDCl₃): 35.4 (s).

$^1$H NMR (CDCl₃): 7.51 (t, $J_{H,H}$=7.6 Hz, 1H, Py-H4), 7.28 (d, $J_{H,H}$=7.6 Hz, 1H, Py-H5), 7.02 (d, $J_{H,H}$=7.6 Hz, 1H, Py-H3), 3.84 (bd, $J_{H,H}$=3.1 Hz, 2H, NHCH₂Py), 3.04 (d, $J_{H,P}$=3.6 Hz, 2H, PCH₂Py), 2.79 (sept, $J_{H,H}$=6.0 Hz, 1H, NH(CH₃)₂CR), 1.89 (bs, 1H, NH(CH₃)₂CH), 1.15 (bd, $J_{P,H}$=9.0 Hz, 18H, (CH₃)₃CPCH₂), 1.07 (d, 6H, NH(CH₃)₂CH); $^{13}$C{$^1$H} NMR (CDCl₃): 161.2 (m, Py-C2, C6), 136.5 (s, Py-C4), 121.8 (d, $J_{C,P}$=10.0 Hz, Py-C3), 118.8 (bm, Py-C5), 48.6 (s, NHCH₂Py), 48.5 (s, NC(CH₃)₃), 31.8 (d, $J_{C,P}$=21.6 Hz, PC(CH₃)₃), 31.5 (d, $J_{C,P}$=23.8 Hz, PCH₂Py), 29.7 (d, $J_{C,P}$=13.0 Hz, PC(CH₃)₃), 29.2 (bs, NHC(CH₃)₂). HRMS: m/z 308.2481 (MH⁺, calcd. m/z 308.2381).

Ligand 3: N-benzyl-1-(6-((di-tert-butylphosphanyl)methyl)pyridin-2-yl)methanamine (L3)

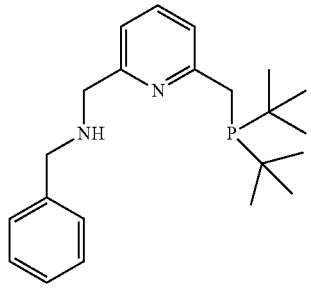

The general method above was employed. Yield: 79%, $^{31}$P{$^1$H} NMR (CDCl₃): 37.0 (s). $^1$H NMR (CDCl₃): 7.44 (t, $J_{H,H}$=7.5 Hz, 1H, Py-H4), 7.26-7.21 (m, 5H, Bn-arom.), 7.17 (d, $J_{H,H}$=7.5 Hz, 1H, Py-H5), 6.98 (d, $J_{H,H}$=7.5 Hz, 1H, Py-H3), 3.80 (bd, $J_{H,H}$=5.1 Hz, 2H, NHCH₂Py), 3.72 (bd, $J_{H,H}$=5.1 Hz, 2H, NHCH₂Bn), 2.97 (d, $J_{H,P}$=3.3 Hz, 2H, PCH₂Py), 2.13 (bs, 1H, NH(CH₃)), 1.09 (d, $J_{P,H}$=9.5 Hz, 18H, PC(CH₃)₃); $^{13}$C{$^1$H} NMR (CD₂Cl₂): 161.7 (m, Py-C2, C6), 158.8 (s, Bn-arom-C1), 136.1 (s, Py-C4), 128.2 (s, Bn-arom-C4), 128.0 (s, Bn-arom-C2,C6), 126.7 (s, Bn-arom-C3,C5), 121.8 (d, $J_{C,P}$=10.0 Hz, Py-C3), 118.7 (s, Py-C5), 54.3 (s,NHCH₂Py), 53.1 (s, NHCH₂Bn), 31.7 (d, $J_{C,P}$=23.8 Hz, PCH$_2$Py), 29.4 (d, $J_{C,P}$=13.0 Hz, PC(CH$_3$)$_3$), 26.6 (s, PC(CH$_3$)$_3$).HRMS: m/z 365.2120 (MNa$^+$, calcd. m/z 365.2122).

Synthesis of 1 (Ru(H)(Cl)(PNNH(t-butyl))(CO))

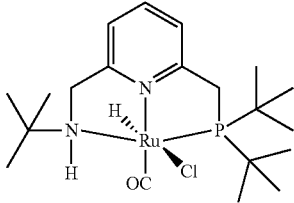

1

To a THF suspension (60 mL) of Ru(H)(Cl)(CO)(PPh$_3$)$_3$ (3.97 g, 4.16 mmol) was added 1.6 equiv of 2-(($^t$Bu$_2$)PCH$_2$-)-6-(($^t$Bu)NHCH$_2$-)pyridine (2.12 g, 6.66 mmol) under nitrogen atmosphere and the reaction mixture was stirred at 65° C. for 1.5 hrs. The reaction mixture was allowed to cool to ambient temperature. Then it was concentrated to 30 ml under vacuum. Pentane was added to precipitate the product and the product was isolated by filtration and washed with ether to yield pure Ru(PNN—H)(H)(Cl)(CO) 1 in 85.5% yield.

Crystals suitable for X-ray analysis were obtained by slow diffusion of pentane into a concentrated dichloromethane solution of 1.

$^{31}$P{$^1$H} NMR (CD$_2$Cl$_2$): 109.2 (s); $^1$H NMR (CD$_2$Cl$_2$): 7.61 (bt, $J_{H,H}$=7.8 Hz, 1H, Py-H4), 7.31 (bd, $J_{H,H}$=7.6 Hz, 1H, Py-H5), 7.13 (d, $J_{H,H}$=8.0 Hz, 1H, Py-H3), 4.39 (m, 1H, NHCHHPy), 4.10 (dd, $J_{H,H}$=14.3 Hz, $J_{H,H}$=10.4 Hz, 2H, NHCHHPy), 3.63 (dd, $J_{H,P}$=16.6 Hz, $J_{H,H}$=8.1 Hz, 1H, PCHHPy), 3.42 (dd, $J_{H,P}$=16.6 Hz, $J_{H,H}$=11.1 Hz, 1H, PCHHPy), 1.60 (bs, 1H, NH(CH$_3$)), 1.40 (bm, 18H, PC(CH$_3$)$_3$), 1.13 (d, $J_{H,P}$=13.3 Hz, 9H, NH(CH$_3$)), −15.85 (d, $J_{H,P}$=13.3 Hz, 1H, Ru—H); $^{13}$C{$^1$H} NMR (CD$_2$Cl$_2$): 208.6 (d, $J_{C,P}$=16.0 Hz, RuCO), 160.6 (d, $J_{C,P}$=4.4 Hz, Py-C2), 159.6 (s, Py-C6), 137.2 (s, Py-C4), 120.8 (d, $J_{C,P}$=9.0 Hz, Py-C3), 118.8 (s, Py-5), 55.2 (s, NCCH$_3$), 54.9 (s, NHCH$_2$Py), 36.7 (d, $J_{C,P}$=10.3 Hz, PC(CH$_3$)$_3$), 36.5 (d, $J_{C,P}$=16.9 Hz, PCH$_2$Py), 36.4 (d, $J_{C,P}$=16.0 Hz, PC(CH$_3$)$_3$), 30.0 (d, $J_{C,P}$=3.9 Hz, PC(CH$_3$)$_3$)), 28.6 (bs, NHC(CH$_3$)$_3$), 28.3 (d, $J_{C,P}$=3.5 Hz, PC(CH$_3$)$_3$)); IR: ν(CO) 1896 cm$^{-1}$. HRMS: m/z 453.161 ([M−Cl]$^+$, calcd. m/z 453.1609).

Synthesis of 2 (Ru(H)(Cl)(PNNH(isopropyl))(CO))

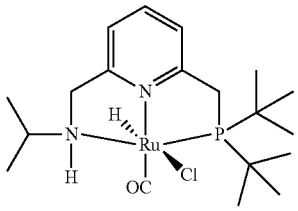

2

To a THF suspension (8.0 mL) of Ru(H)(Cl)(CO)(PPh$_3$)$_3$ (478.0 mg, 0.50 mmol) was added 1.5 equiv. of ligand L2 (232.0 mg, 0.75 mmol) under N$_2$ atmosphere and the reaction mixture was stirred at 65° C. for 4.0 h. It was brought to ambient temperature and the solvent was concentrated to one third of its volume. Pentane was added to precipitate the product which was filtered and washed with ether to afford complex 2 (212.0 mg) in 90.0% yield. Crystals suitable for X-ray analysis were obtained by slow diffusion of pentane into a concentrated CH$_2$Cl$_2$ solution of the complex.

$^{31}$P{$^1$H} NMR (CD$_2$Cl$_2$): 109.5 (s); $^1$H NMR (CD$_2$Cl$_2$): 7.61 (bt, $J_{H,H}$=7.8 Hz, 1H, Py-H4), 7.31 (bd, $J_{H,H}$=9.0 Hz, 1H, Py-H5), 7.13 (d, $J_{H,H}$=9.0 Hz, 1H, Py-H3), 4.68 (bs, 1H, NH(CH$_3$)$_2$CH), 4.35 (m, 1H, NHCHHPy), 4.15 (dd, $J_{H,H}$=12.0, $J_{H,H}$=12.0 Hz, 2H, NHCHHPy), 3.63 (dd, $J_{H,P}$=12.0 Hz, $J_{H,H}$=8.9 Hz, 1H, PCHHPy), 3.42 (dd, $J_{H,P}$=16.6 Hz, $J_{H,H}$=11.1 Hz, 1H, PCHHPy), 3.03 (m, 1H, NH(CH$_3$)$_2$CH), 1.40 (d, 9H, $J_{H,P}$=13.4 Hz, PC(CH$_3$)$_3$, 1.35 (d, $J_{H,H}$=6.0 Hz, 3H, NH(CH$_3$)$_2$CH), 1.35 (d, $J_{H,H}$=6.1 Hz, 3H, NH(CH$_3$)$_2$CH), 1.16 (d, 9H, $J_{H,P}$=13.0 Hz, PC(CH$_3$)$_3$), −15.94 (d, $J_{H,P}$=23.3 Hz, 1H, Ru—H); $^{13}$C{$^1$H} NMR (CD$_2$Cl$_2$): 207.5 (d, $J_{C,P}$=16.8 Hz, RuCO), 160.3 (d, $J_{C,P}$=4.4 Hz, Py-C2), 158.3 (s, Py-C6), 136.7 (s, Py-C4), 120.4 (d, $J_{C,P}$=9.0 Hz, Py-C3), 117.6 (s, Py-C5), 58.08 (s, NHCH$_2$Py), 36.5 (d, $J_{C,P}$=8.5 Hz, PCH$_2$Py), 36.0 (d, $J_{C,P}$=12.3 Hz, PC(CH$_3$)$_3$), 29.4 (d, $J_{C,P}$=3.7 Hz, PC(CH$_3$)$_3$), 39.4 (d, $J_{C,P}$=3.9 Hz, PC(CH$_3$)$_3$, 27.8 (d, $J_{C,P}$=3.5 Hz, PC(CH$_3$)$_3$, 22.4 (s, (CH$_3$)$_2$CH)), 20.4 (s, (CH$_3$)$_2$CH)), IR: ν(C—O) 1895 cm$^{-1}$. HRMS: m/z 439.1459 ([M−Cl]$^+$, calcd. m/z 439.1452).

Synthesis of 3 (Ru(H)(Cl)(PNNH(benzyl))(CO))

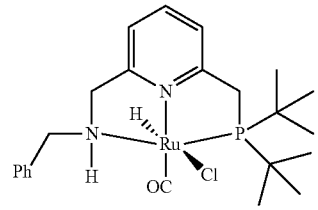

3

To a THF suspension (6.0 mL) of Ru(H)(Cl)(CO)(PPh$_3$)$_3$ (430.0 mg, 0.45 mmol) was added ligand L3 (256.0 mg, 0.72 mmol) under N$_2$ atmosphere and the reaction mixture was stirred at 65° C. for 4.0 h. It was brought to ambient temperature and the solvent was concentrated to one third of its volume. Pentane was added to precipitate the product which was filtered and washed with ether to afford complex 3 (200.0 mg) in 85% yield. Crystals suitable for X-ray analysis were obtained by slow diffusion of pentane into a concentrated CH$_2$Cl$_2$ solution of the complex.

$^{31}$P{$^1$H} NMR (CD$_2$Cl$_2$): 108.7 (s); $^1$H NMR (CD$_2$Cl$_2$): 7.61 (bt, $J_{H,H}$=7.8 Hz, 1H, Py-H4), 7.43-7.37 (m, 6H, overlapped Bn-H and Py-H5), 7.04 (d, $J_{H,H}$=7.0 Hz, 1H, Py-H3), 4.77 (bs, 1H, NH-Bn), 4.75 (bd, $J_{H,H}$=10.3 Hz, 1H, NHCHHPhenyl), 4.25 (d, $J_{H,H}$=15.0 Hz, 1H, NHCHHPy), 4.12 (t, $J_{H,H}$=11.6 Hz, 1H, NHCHHPhenyl), 4.00 (d, $J_{H,H}$=10.8 Hz, 1H, NHCHHPy), 3.67 (dd, $J_{H,P}$=15.6 Hz, $J_{H,H}$=7.5 Hz, 1H, PCHHPy), 3.51 (dd, $J_{H,P}$=12.6 Hz, $J_{H,H}$=7.5 Hz, 1H, PCHHPy), 1.45 (d, 9H, $J_{H,P}$=13.4 Hz, PC(CH$_3$)$_3$, 1.16 (d, 9H, $J_{H,P}$=13.0 Hz, PC(CH$_3$)$_3$, −15.55 (d, $J_{H,P}$=23.3 Hz, 1H, Ru—H); $^{13}$C{$^1$H} NMR (CD$_2$Cl$_2$): 209.1 (d, $J_{C,P}$=15.0 Hz, RuCO), 161.0 (d, $J_{C,P}$=4.7 Hz, Py-C2), 159.9 (s, Py-C6), 137.2 (s, Py-C4), 129.1 (s, Bn-arom-C2, C6), 128.8 (s, Bn-arom-C3,C5), 128.2 (s, Bn-arom.-C4), 121.0 (d, $J_{C,P}$=9.0 Hz, Py-C3), 118.8 (s, Py-C5), 61.8 (s, CH$_2$Bn), 59.4 (s, NHCH$_2$Py), 36.7 (d, $J_{C,P}$=15.0 Hz, PCH₂Py), 36.5 (d, J_{C,P}=3.3 Hz, PC(CH₃)₃, 36.3 (d, J_{C,P}=3.3 Hz, PC(CH₃)₃, 30.1 (d, J_{C,P}=3.9 Hz, PC(CH₃)₃, 28.4 (d, J_{C,P}=3.5 Hz, PC(CH₃)₃. ESI (MS): 487.21 [M–Cl]⁺; IR: ν(C—O) 1907 cm⁻¹. HRMS: m/z 487.1458 ([M–Cl]⁺, calcd. m/z 487.1452).

Synthesis of the Anionic Enamido Complex 4' (Ru(H)(PNN⁻(t-butyl))(CO)K⁺)

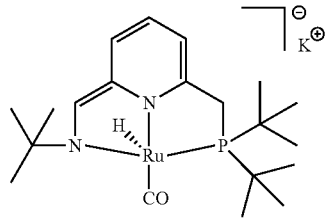

4'

To a suspension of the hydridochloride 1 (15.0 mg, 0.03 mmol) in dry THF-d8, was added KH (3.2 mg, 0.077 mmol) and solution was stirred for 18 h at RT in a J.Young NMR tube. The reaction mixture initially turns dark brown and later violet at which stage it was characterized in situ by NMR. The product was then filtered through a celite plug, concentrated and washed with ether. Crystals suitable for X-ray analysis can be obtained by slow diffusion of ether in concentrated solution of the complex in THF at RT.

Yield: 11.0 mg (73%). ³¹P{¹H} NMR (THF-d8): 124.1 (d, J_{H,P}=15.0 Hz); ¹H NMR (THF-d8): 6.65 (bs, 1H, (t-butyl)NCHC—), 6.29 (bd, 1H, J_{H,H}=12.0 Hz, Py-C5), 5.62 (bt, 1H, J_{H,H}=12.0 Hz, Py-C4), 5.08 (bs, 1H, Py-C3), 3.20 (dd, J_{H,P}=12.0 Hz, J_{H,H}=4.5 Hz, 1H, PCHHPy), 2.91 (dd, J_{H,P}=12.0 Hz, J_{H,H}=4.5 Hz, 1H, PCHHPy), 1.63 (s, 9H, (CH₃)₃N), 1.32 (d, 9H, J_{H,P}=12.0 Hz, PC(CH₃)₃, 1.16 (d, 9H, J_{H,P}=12.0 Hz, PC(CH3)3), –18.45 (d, J_{H,P}=28.0 Hz, 1H, Ru—H); ¹³C{¹H} NMR (THF-d8): 212.6 (bd, J_{C,P}=15.0 Hz, RuCO), 156.4 (s, Py-C6), 132.0 (s, Py-C2), 116.1 (s, Py-C4), 114.8 (s, (t-butyl)NCHC—), 114.6 (s, py-C5), 92.0 (d, J_{C,P}=9.0 Hz, Py-C3), 36.3 (s, (CH₃)₃CN), 32.5 (d, J_{C,P}=6.0 Hz, PC(CH₃)₃), 32.3 (d, J_{C,P}=6.0 Hz, PC(CH₃)₃), 34.2 (d, J_{C,P}=15.0 Hz, PCH₂Py), 33.5 (s, NC(CH₃)₃), 33.0 (s, NC(CH₃)₃), 28.4 (d, J_{C,P}=3.9 Hz, PC(CH₃)₃, 26.3 (d, J_{C,P}=3.5 Hz, PC(CH₃)₃. ES (MS) negative mode: 451.07 [M⁻]; IR: ν(CO) 1907 cm⁻¹.

Formation of 6

Figure 8:
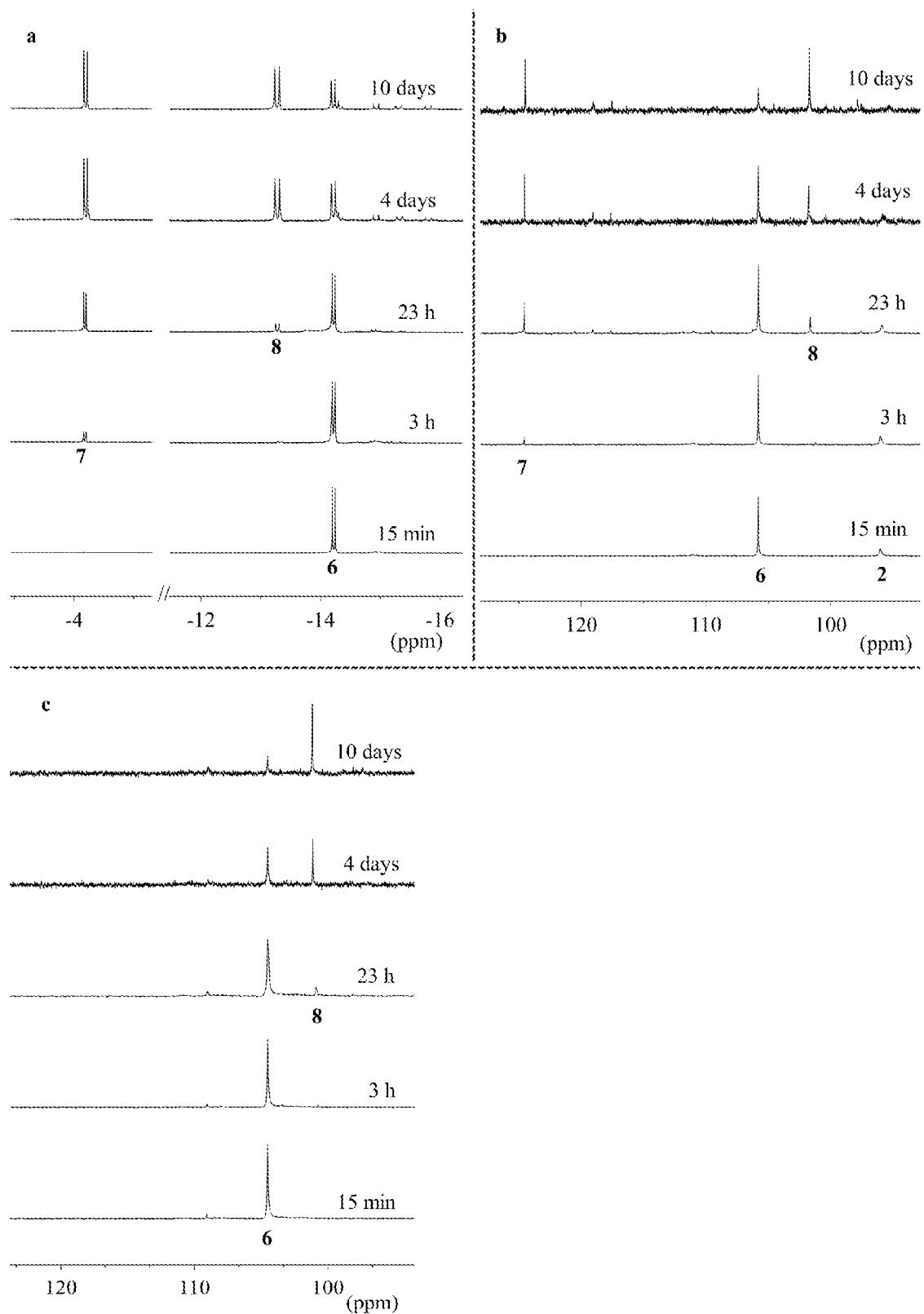
FIG. 8: Reaction of complex (ii) with 2-aminoethanol at r.t. in $C_6D_6$. a, $^1H$ NMR spectra using 1.5 equiv of 2-aminoethanol. b, $^{31}P\{^1H\}$ NMR spectra using 1.5 equiv of 2-aminoethanol. c, $^{31}P\{^1H\}$ NMR spectra using 10 equiv of 2-aminoethanol.
Figure 9:
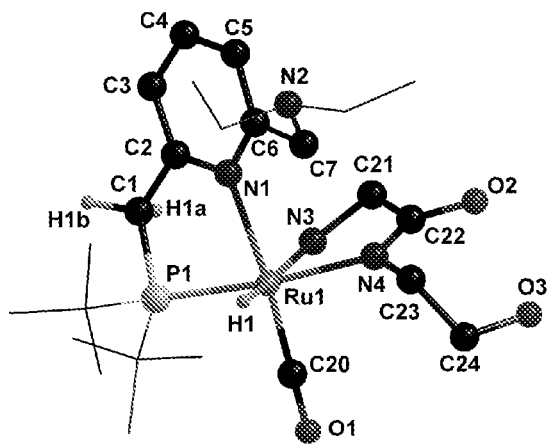
FIG. 9: X-ray structure of complex 8. Hydrogen atoms (except for the hydride and the hydrogen atoms on C1) are omitted for clarity. ($^t$Bu groups and Et groups are presented as wireframe for clarity.) Selected bond lengths [Å] and angles [°]: Ru(1)-C(20) 1.809(3), Ru(1)-N(4) 2.147(2), Ru(1)-N(3) 2.232(3), Ru(1)-N(1) 2.248(3), Ru(1)-P(1) 2.2733(8), Ru(1)-H(1) 1.7275, C(1)-C(2) 1.506(4), C(6)-C(7) 1.510(4), C(22)-O(2) 1.273(4), C(24)-O(3) 1.414(4); C(20)-Ru(1)-N(4) 90.33(11), C(20)-Ru(1)-N(3) 100.93(13), N(4)-Ru(1)-N(3) 75.75(9), C(20)-Ru(1)-N(1) 174.84(12), N(4)-Ru(1)-N(1) 94.33(9), N(3)-Ru(1)-N(1) 82.39(10), N(4)-Ru(1)-P(1) 172.46(7), N(3)-Ru(1)-P(1) 98.22(7), N(1)-Ru(1)-P(1) 80.23(7).

In a glove box, a vial was charged with 1.8 mg (0.03 mmol) or 12.2 mg (0.2 mmol) of 2-aminoethanol and a solution of 9 mg (0.02 mmol) of complex 2 ((ᵗBuPNN)Ru(H)(CO)) in 0.5-0.6 mL C₆D₆ or toluene-d8 was added. After shaking for 2 min, the color changed from brown to dark red and the solution was added to a NMR tube and analyzed by NMR. The sample dissolved in toluene-d8 was analyzed at –30° C. Samples dissolved in C₆D₆ were analyzed at room temperature. Complex 6 was produced in nearly quantitative yield in 15 min, which was observed by ¹H NMR (FIG. 8a) and ³¹P{¹H} NMR spectra (FIG. 8, b & c).

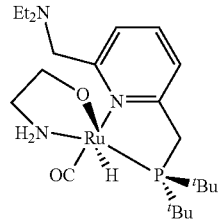

6

³¹P{¹H} NMR (162 MHz, C₆D₆, 20° C.): 105.6 (s).
³¹P{¹H} NMR (162 MHz, toluene-d8, –30° C.): 106.3 (s).
¹H NMR (400 MHz, C₆D₆, 20° C.): 6.99-6.92 (m, 2H, Py-H_{meta} and Py-H_{para}), 6.76 (d, J_{HH}=7.0 Hz, 1H, Py-H_{meta}), 5.10 (dd, J_{HH}=14.3 Hz, J_{PH}=8.7 Hz, 1H, –CHHP), 4.58 (br, 1H, —NHH), 4.10 (d, J_{HH}=13.0 Hz, 1H, —CHHNEt₂), 3.95-3.90 (m, 1H, —CHHO), 3.68-3.63 (m, 1H, —CHHO), 3.59 (d, J_{HH}=12.9 Hz, 1H, —CHHNEt₂), 3.07 (t, J_{HH}=13.3 Hz, J_{PH}=13.3Hz, 1H, —CHHP), 2.83 (br, 1H, —NHH), 2.51-2.40 (m, 3H, N(CH₂Me)₂ and —CHHNH₂), 2.29-2.19 (m, 2H N(CH₂Me)₂), 2.09 (br, 1H, —CHHNH₂), 1.60 (d, J_{PH}=12.8 Hz, 9H, P—C(CH₃)₃), 1.01 (d, J_{PH}=12.0 Hz, 9H, P—C(CH₃)₃), 0.86 (t, J_{HH}=7.1 Hz, 6H, N(CH₂CH₃)₂), –14.22 (d, J_{PH}=18.9 Hz, 1H, Ru—H). ¹H NMR (400 MHz, toluene-d8, –30° C.): 6.97-6.95 (m, overlapped with peak of toluene, 1H, Py-H_{para}), 6.76 (d, J_{HH}=7.0 Hz, 1H, Py-H_{meta}), 6.70 (d, J_{HH}=7.5 Hz, 1H, Py-H_{meta}), 5.27 (br, 1H, —NHH), 4.89 (dd, J_{HH}=14.7 Hz, J_{PH}=7.7 Hz, 1H, —CHHP), 4.12 (d, J_{HH}=12.3 Hz, 1H, —CHHNEt₂), 3.82-3.78 (m, 1H, —CHHO), 3.54-3.51 (m, 1H, —CHHO), 3.20 (d, J_{HH}=12.2 Hz, 1H, —CHHNEt2), 3.02 (dd, J_{HH}=14.7 Hz, J_{PH}=13.1 Hz, 1H, —CHHP), 2.62 (br, 1H, —NHH), 2.43-2.34 (m, 2H, N(CH₂Me)₂), 2.30 (br, 1H, —CHHNH₂), 2.04-1.99 (m, overlapped with the peak of toluene, 3H, N(CH₂Me)₂ and —CHHNH₂), 1.53 (d, J_{PH}=12.7 Hz, 9H, P—C(CH₃)₃), 0.92 (d, J_{PH}=11.8 Hz, 9H, P—C(CH₃)₃), 0.79 (t, J_{HH}=6.9 Hz, 6H, N(CH₂CH₃)₂), –14.11 (d, J_{PH}=18.6 Hz, 1H, Ru—H).

¹³C{¹H} NMR (100 MHz, toluene-d8, –30° C.): 208.03 (d, J_{PC}=15.4 Hz, Ru—CO), 164.86 (d, J_{PC}=2.3 Hz, C_{Py}—CH₂—P), 159.70 (s, C_{Py}—CH₂—N), 135.76 (s, C_{Py}—H_{para}), 123.04 (s, CH—C(N)—CH₂—N), 122.80 (d, J_{PC}=6.6 Hz, CH—C(N)—CH₂—P), 69.16 (d, J_{PC}=4.2 Hz, O—CH₂—CH₂), 61.36 (s, Py-CH₂-N), 47.35 (s, NH₂—CH₂—CH₂), 45.86 (s, N(CH₂CH₃)₂), 36.14 (d, J_{PC}=16.8 Hz, P—C(CH₃)₃), 35.01 (d, J_{PC}=20.1 Hz, P—C(CH₃)₃), 34.82 (d, J_{PC}=12.2 Hz, Py-CH₂—P), 30.37 (d, J_{PC}=4.1 Hz, P—C(CH3)3), 29.31 (d, J_{PC}=2.4 Hz, P—C(CH3)3), 10.89 (s, N(CH₂CH₃)₂).

¹H and ¹³C signal assignments were confirmed by ¹H{³¹P}, ¹H COSY, ¹³C DEPTQ, ¹³C—¹H HSQC and NOESY.

IR (benzene, plate): ν C—O 1907 cm⁻¹.

Because complex 6 is not stable, HRMS was not obtained.

Formation of 8.

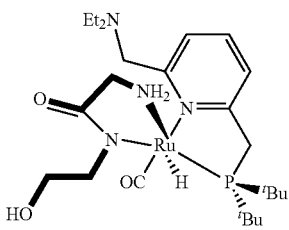

In a glove box, a 5 mL vial was charged with 1.8 mg (0.03 mmol) of 2-aminoethanol and a solution of 9 mg (0.02 mmol) of complex (ii) (($^t$BuPNN)Ru(H)(CO)) in 0.5-0.6 mL $C_6H_6$. After shaking for 2 min, the color changed from brown to dark red. Then the open 5 mL vial was placed in a 20 mL vial which contained ~5 mL pentane. The 20 mL vial was closed tightly with a cap to let slow diffusion of pentane into the benzene solution in the 5 mL vial. After 2 weeks, crystals suitable for X-ray analysis were obtained. The procedure was repeated and the crystals were carefully collected, washed wish benzene, dried (2.4-4.3 mg pure complex was obtained every time) and dissolved in acetone-$d_6$ or THF-$d_8$ for NMR study.

Independent Preparation of Complex 8

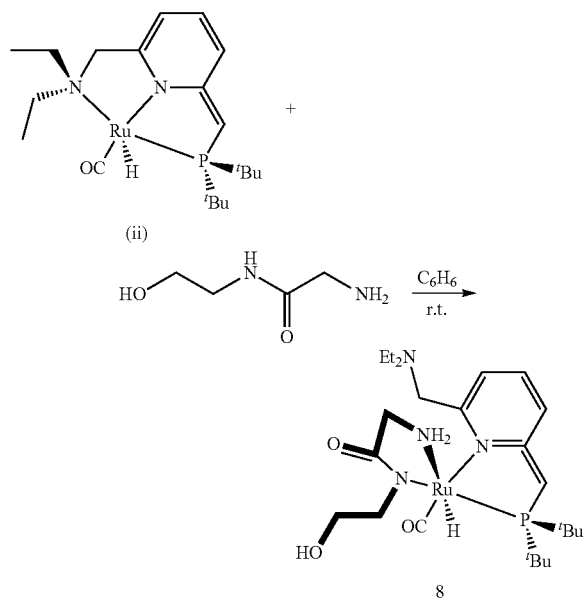

In a glove box, a 5 mL vial was charged with a stirring bar, 2.8 mg (0.024 mmol) of 2-amino-N-(2-hydroxyethyl)acetamide and a solution of 9 mg (0.02 mmol) of complex (ii) (($^t$BuPNN)Ru(H)(CO)) in 0.5-0.6 mL $C_6H_6$. After stirring for 1-2 days, the solution was clear and the insoluble solid disappeared. The open 5 mL vial was placed in a 20 mL vial which contained ~5 mL pentane. The 20 mL vial was closed tightly with a cap to let slow diffusion of pentane into the benzene solution in the 5 mL vial. After 2 weeks, crystals suitable for X-ray analysis were obtained.

$^{31}P\{^1H\}$ NMR (162MHz, acetone-$d_6$, 20° C.): 100.7 (s)

$^1H$ NMR (400 MHz, acetone-$d_6$, 20° C.): 7.80 (t, $J_{HH}$=7.6 Hz, 1H, Py-H$_{para}$), 7.75 (d, $J_{HH}$=7.6 Hz, 1H, Py-H$_{meta}$, the one close to —NEt$_2$), 7.47 (d, $J_{HH}$=7.6 Hz, 1H, Py-H$_{meta}$, the one close to —P($^t$Bu)$_2$), 4.28-4.23 (m, 1H, —CHHCH$_2$OH), 4.04 (d, $J_{HH}$=16.7 Hz, 1H, —CHHNEt$_2$), 3.92 (td, $J_{HH}$=10.1, 1.9 Hz, 1H, —CHHOH), 3.87 (d, $J_{HH}$=16.7 Hz, 1H, —CHHNEt$_2$), 3.80-3.68 (m, 3H, —CHHOH and —CH$_2$P), 3.51-3.47 (m, 1H, —CHHCH$_2$OH), 3.02 (dd, $J_{HH}$=14.7, 5.8 Hz, 1H, —CHHNH$_2$), 2.65-2.61 (bm, 1H, —NHH), 2.58-2.49 (m, 2H, N(CH$_2$Me)$_2$), 2.47-2.39 (m, 2H, N(CH$_2$Me)$_2$), 1.99-1.91 (m, —CHHNH$_2$), 1.41 (d, $J_{PH}$=12.7 Hz, 9H, P—C(CH$_3$)$_3$), 1.08 (d, $J_{PH}$=12.7 Hz, 9H, P—C(CH$_3$)$_3$), 1.02 (t, $J_{HH}$=7.1 Hz, 6H, N(CH$_2$CH$_3$)$_2$), -13.49 (d, $J_{PH}$=23.4 Hz, 1H, Ru—H). Proton of —OH and one proton of —NH$_2$ were not observed.

$^{13}C\{^1H\}$ NMR (100 MHz, acetone-$d_6$, 20° C.): 208.84 (d, $J_{PC}$=15.6 Hz, Ru—CO), 178.75 (d, $J_{PC}$=1.4 Hz, C═O), 166.37 (s, C$_{Py}$—CH$_2$—N), 162.64 (d, $J_{PC}$=5.6 Hz, C$_{Py}$—CH$_2$—P), 138.44 (s, C$_{Py}$—H$_{para}$), 122.87(d, $J_{PC}$=8.1 Hz, CH—C(N)—CH$_2$—P), 122.07(s, CH—C(N)—CH$_2$—N), 66.20 (s, CH$_2$—OH), 61.78 (s, CH$_2$—NEt$_2$), 58.44 (s, CH$_2$—CH$_2$—OH), 48.76 (s, CH$_2$—NH$_2$), 48.01 (s, N(CH$_2$CH$_3$)$_2$), 36.05 (d, $J_{PC}$=23.4 Hz, P—(C(CH$_3$)$_3$)$_2$), 35.77 (d, $J_{PC}$=17.6 Hz, CH$_2$—P), 29.67 (s, P—C(CH3)3), 28.08 (s, P—C(CH3)3), 12.43 (s, N(CH$_2$CH$_3$)$_2$).

$^{31}P\{^1H\}$ NMR (162 MHz, THF-$d_8$, 20° C.): 101.2 (s)

$^1H$ NMR (400 MHz, THF-$d_8$, 20° C.): 7.71 (d, $J_{HH}$=7.5 Hz, 1H, Py-H$_{meta}$, the one close to —NEt$_2$), 7.65 (t, $J_{HH}$=7.5 Hz, 1H, Py-H$_{para}$), 7.33 (d, $J_{HH}$=7.5 Hz, 1H, Py-H$_{meta}$, the one close to —P($^t$Bu)$_2$), 5.41 (dd, $J_{HH}$=2.3, 6.0 Hz, 1H, —OH), 4.27-4.21 (m, 1H, —CHHCH$_2$OH), 4.06 (d, $J_{HH}$=16.9 Hz, 1H, —CHHNEt$_2$), 3.94-3.80 (m, 4H, —CHHOH, —CHHP, —NHH and —CHHNEt$_2$), 3.30-3.65 (m, 1H, —CHHOH), 3.64-3.57 (m, 1H, —CHHP, overlapped with peak of THF), 3.46-3.42 (m, ≥CHHCH$_2$OH), 2.80 (dd, $J_{HH}$=14.8, 5.1 Hz, 1H, —CHHNH$_2$), 2.72-2.68 (bm, 1H, —NHH), 2.56-2.47 (m, 2H, N(CH$_2$Me)$_2$), 2.47-2.38 (m, 2H, N(CH$_2$Me)$_2$), 1.77-1.70 (m, 1 H, —CHHNH$_2$, overlapped with peak of THF), 1.37 (d, $J_{PH}$=12.6 Hz, 9H, P—C(CH$_3$)$_3$), 1.03 (d, $J_{PH}$=12.6 Hz, 9H, P—C(CH$_3$)$_3$), 1.03 (t, $J_{HH}$=6.9 Hz, 6H, N(CH$_2$CH$_3$)$_2$), -13.45 (d, $J_{PH}$=23.3 Hz, 1H, Ru—H).

$^{13}C\{^1H\}$ NMR (100 MHz, THF-$d_6$, 20° C.): 208.50 (d, $J_{PC}$=15.1 Hz, Ru—CO), 178.60 (s, C═O),167.28 (s, C$_{Py}$—CH$_2$—N), 162.60 (d, $J_{PC}$=5.6 Hz, C$_{Py}$—CH$_2$—P), 137.82 (s, C$_{Py}$—H$_{para}$), 122.35 (d, $J_{PC}$=7.9 Hz, CH—C(N)—CH$_2$—P), 122.18 (s, CH—C(N)—CH$_2$—N), 66.61 (s, CH$_2$—OH), 62.13 (s, CH$_2$—NEt$_2$), 58.71 (s, CH$_2$—CH$_2$—OH), 49.52 (s, CH$_2$—NH$_2$), 48.28 (s, N(CH$_2$CH$_3$)$_2$), 36.25 (d, $J_{PC}$=22.6 Hz, P—C(CH$_3$)$_3$), 35.93 (d, $J_{PC}$=16.1 Hz, P—C(CH$_3$)$_3$), 34.94 (d, $J_{PC}$=14.6 Hz, CH$_2$—P), 29.78 (d, $J_{PC}$=3.8 Hz, P—C(CH3)3), 28.34 (d, $J_{PC}$=4.0 Hz, P—C(CH3)3), 12.56 (s, N(CH$_2$CH$_3$)$_2$).

$^1H$ and $^{13}C$ signal assignments were confirmed by $^1H\{^{31}P\}$, $^1H$ COSY, $^{13}C$ DEPTQ, $^{13}C$—$^1H$ HSQC.

IR (film): 1947, 1896, 1568 cm$^{-1}$

HRMS calcd for $C_{20}H_{36}N_2OPRu$ [M-(HOCH$_2$CH$_2$NCOCH$_2$NH$_2$)]$^+$: 453.1609, found: 453.1575.

Synthesis of 2-amino-N-(2-hydroxyethyl)acetamide

This compound was reported. Herein a new procedure to produce it in one step from glycine anhydride is reported.

In a glove box, a 20 mL Parr reactor was charged with complex 1 (0.01 mmol), KOtBu (0.012 mmol), glycine anhydride (0.5 mmol) and dioxane (4 mL) under an atmosphere of purified nitrogen. The Parr reactor was taken out of the glove box, and subjected to three successive cycles of pressurization/venting with H$_2$ (3 atm), then pressurized with H2 (50 bar) and closed. The Parr reactor was placed behind a protective shield and the reaction mixture was heated in an oil bath at 110° C. with constant stirring for 48 h. After cooling to room temperature, excess H2 was vented off carefully. The solution was collected and the solvent was evaporated under vacuum to give a solid. The solid was purified by recrystallization (methanol-ether) and 36 mg (61%) pure 2-amino-N-(2-hydroxyethyl)acetamide was obtained as a white solid.

$^1$H NMR (D$_2$O): 3.48 (t, J=5.5 Hz, 2H), 3.16 (t, J=5.5 Hz, 2H), 3.10 (s, 2H). $^{13}$C{$^1$H} NMR (D$_2$O): 175.46, 59.85, 43.62, 41.17. HRMS calcd for C$_4$H$_{10}$N$_2$O$_2$Na [N+Na]$^+$: 141.0640, found: 141.0635.

Catalytic Experiments—General Procedures

All the dehydrogenation experiments were carried out by the addition of the appropriate amounts of mentioned complex and base to the pure substrate in dry solvents. The mixture was then refluxed in a flask fitted with condenser with vigorous stirring under bubbling argon for the specified amount of time (open system). For reactions with diethyl ether as the solvent cold water circulation needed to be maintained throughout the reaction course. After the specified reaction time, a known quantity of an internal standard was added to the reaction mixture. It was then analyzed by GC for conversions and yields.

General Procedure for the Dehydrogenation of 2-aminoethanol:

In a glove box, a 25 mL Schlenk flask was charged with a stirring bar, catalyst (0.005 mmol), KOtBu (0.006-0.012 mmol), 2-aminoethanol (1 mmol) and dioxane (4 mL) under an atmosphere of nitrogen. The flask was taken out of the glove box, equipped with a condenser and the solution was refluxed with stirring in an open system under a flow of argon for 12 h. After cooling to room temperature, 1 mmol of 1,3,5-trimethylbenzene was added to the crude reaction mixture as an internal standard. Then 0.05 mL of the solution was dissolved in CDCl$_3$ for determination of the conversion of 2-aminoethanol by $^1$H NMR spectroscopy. To the rest of the solution was added 10-15 mL hexane and the mixture was cooled down to 0° C. The formed precipitate was collected by simple filtration and washed with 10 mL of hexane and dried under vacuum. 1 mmol pyridine was then added to the dry solid as an internal standard and the mixture was analyzed by $^1$H NMR spectroscopy to determine the yield of glycine anhydride (GA), using D$_2$O as the solvent.

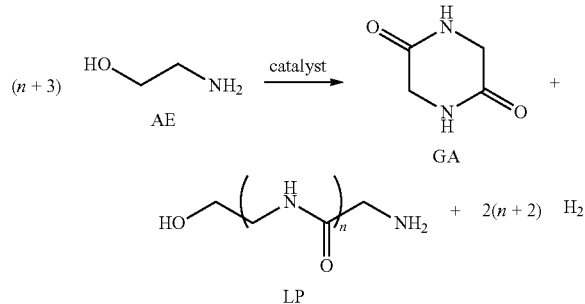

MS (ESI) of products obtained under conditions of Table 4 entry 4: 119.02 (linear peptide (n=1)+H), 141.03 (linear peptide (n=1)+Na), 198.05 (linear peptide (n=2)+Na), 233.06 (GA+linear peptide (n=1)+H), 255.13 (GA+linear peptide (n=1)+Na or linear peptide (n=3)+Na), 312.21 (linear peptide (n=4)+Na), 369.15 (linear peptide (n=5)+Na), 430.34 (linear peptide (n=6)+4H+Na), 453.17 (linear peptide (n=6)+4H+2Na).

MS (CI): 112.93 (GA-H), 116.99 (linear peptide (n=1)-H), 174.01 (linear peptide (n=2)-H), 231.03 (GA+linear peptide (n=1)-H), 288.30 (linear peptide (n=4)-H), 402.25 (linear peptide (n=6)-H).

General Procedure for the Hydrogenation of Glycine Anhydride

In a glove box, a 100 mL Fischer-Porter tube or a 20 mL Parr apparatus was charged with catalyst (0.005 mmol), KOtBu (0.006-0.012 mmol), glycine anhydride (0.5-1.0 mmol) and dioxane or THF (2 or 4 mL) under an atmosphere of purified nitrogen. The pressure equipment was taken out of the glove box, and subjected to three successive cycles of pressurization/venting with H$_2$ (3 atm), then pressurized with H$_2$ (10-50 bar) and closed. The pressure equipment was placed behind a protective shield and the reaction mixture was heated in an oil bath at 110° C. with constant stirring for 24-48 h. After cooling to room temperature, excess H$_2$ was vented off carefully. The unreacted glycine anhydride was filtered off washed with 10 mL of hexane and dried under vacuum. To the dry solid was then added 1 mmol of pyridine as an internal standard, dissolved in D$_2$O for determination of the amount of glycine anhydride by $^1$H NMR spectroscopy The filtrate was collected and evaporated under vacuum to give a mixture. To the mixture was added 1 mmol of pyridine as an internal standard, dissolved in D$_2$O and analyzed by $^1$H NMR spectroscopy to determine the yield of 2-aminoethanol and the amount of glycine anhydride in solution. The total amount and the relative conversion of glycine anhydride were obtained in this way (the reason for this procedure is inaccurate determination of 2-aminoethanol in the presence of a large amount of glycine anhydride).

Figure 10:
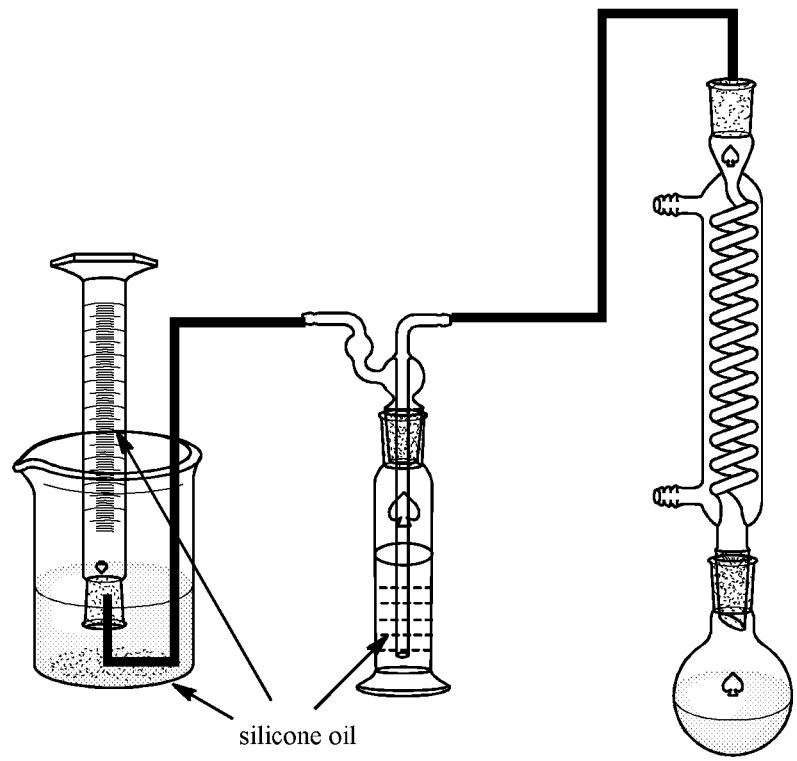
FIG. 10. Schematic drawing of a gas collection system for the 2-aminoethanol LOHC system.

General Procedure for Gas Collection:

In a glove box, a 25 mL Schlenk flask was charged with a stirring bar, catalyst (0.005 mmol), KOtBu (0.006-0.012 mmol), 2-aminoethanol (1 mmol) and dioxane (4 mL) under an atmosphere of nitrogen. The flask was taken out of the glove box, equipped with a reflux condenser and connected to a gas collection system under a flow of argon. The whole open system was flushed with argon and then connected to an inverted graduated cylinder filled with silicon oil (see schematic drawing below). The solution was refluxed with stirring and after 9 hrs no more gas bubbles were observed. After 12 h the volume of the generated gas was recorded as V1. To quantify the effect of warming on the gas volume, the condenser was disconnected from the gas collection system and opened in the air. After the flask was cooled to room temperature, the condenser was connected with the gas collection system again. The solvent was refluxed for another 0.5 h until no gas bubbles (as a result of argon expansion) were observed, and the increased volume of gas in the flask when heating was recorded as V2. The volume of H$_2$ produced was V1-V2. The experimental set-up is set forth in FIG. 10.

Procedure for 20 mmol Scale Dehydrogenation Reaction.

In a glove box, a 250 mL Schlenk flask was charged with a stirring bar, catalyst 5 (0.1 mmol), KOtBu (0.24 mmol), 2-aminoethanol (20 mmol) and dioxane (80 mL) under an atmosphere of nitrogen. The flask was taken out of the glove box, equipped with a reflux condenser and connected to a gas collection system under a flow of argon. The whole open system was flushed with argon and then connected to an inverted graduated cylinder filled with silicon oil (see FIG. 10). The solution was refluxed with stirring for 12 h. After cooling to room temperature, 4 mmol of 1,3,5-trimethylbenzene was added to the crude reaction mixture as an internal standard. Then 0.05 mL of the solution was dissolved in CDCl$_3$ for determination of the conversion of 2-aminoethanol by $^1$H NMR spectroscopy. To the rest of the solution was added 100 mL hexane and the mixture was cooled down to 0° C. The formed precipitate was collected by simple filtration and washed with 3×30 mL of hexane and dried under vacuum. 10 mmol of pyridine was then added to the dry solid as an internal standard and the mixture was dissolved with 10 mL H$_2$O. Then 0.05 mL of the solution was added with D$_2$O to determine the yield of glycine anhydride (GA) by $^1$H NMR spectroscopy.

Procedure for 5 mmol Scale Hydrogenation Reaction.

The general procedure for the hydrogenation of glycine anhydride was followed with Complex 1 (1 mol %), KO$^t$Bu (2.4 mol %), GA (5 mmol), and dioxane (5 mL) under 70 bar of H$_2$ for 12 h.

Procedure for the Repetitive Reversal Reactions:

TABLE 7

Repetitive reversal reactions catalyzed by 0.5 mol % complex 1

| Cycle | Conversion of dehydrogenation (%)$^a$ | Conversion of hydrogenation (%)$^a$ |
| --- | --- | --- |
| 1 | 82 | 95 (94) |
| 2 | 73 (77) | 80 (73) |
| 3 | 61 (76) | 70 (51) |

0.5 mol % complex 1 was used.
$^a$Based on the amount of 2-aminoethanol in the system.
The number in parenthesis is based on the product of the former step.

a) Using 0.5 mol % complex 1 (Table 7): In a glove box, a 25 mL Schlenk flask was charged with a stirring bar, catalyst 1 (0.005 mmol), KOtBu (0.012 mmol), 2-aminoethanol (1 mmol) and dioxane (4.5 mL) under an atmosphere of nitrogen. The flask was taken out of the glove box, equipped with a condenser and the solution was refluxed with stirring in an open system under a flow of argon for 8 h. After cooling to room temperature, the flask was sealed under a flow of argon and taken into a glove box. 1 mmol of 1,3,5-trimethylbenzene was added to the crude reaction mixture as an internal standard. Then 0.05 mL of the solution was dissolved in CDCl$_3$ for determination of the conversion of 2-aminoethanol by $^1$H NMR spectroscopy. All of the rest of the solution and precipitate were transferred to a 20 mL Parr apparatus. A catalytic amount of KOtBu (0.012 mmol) was also added to protect the catalyst from trace amount of water, which may be taken into the system during the course of transfer. The Parr apparatus was taken out of the glove box and subjected to three successive cycles of pressurization/venting with H$_2$ (3 atm), then pressurized with H$_2$ (60 bar) and closed. The Parr apparatus was placed behind a protective shield and the reaction mixture was heated in an oil bath at 110° C. with constant stirring for 10 h. After cooling to room temperature, excess H$_2$ was carefully vented off. The Parr apparatus was taken into the glove box again and 0.05 mL of the solution was dissolved in CDCl$_3$ for determination of the conversion by $^1$H NMR spectroscopy. The reaction mixture was then transferred to a 25 mL Schlenk flask together with 0.012 mmol KOtBu. The flask was taken out of the glove box equipped with a condenser and the solution was refluxed with stirring in an open system under a flow of argon for 11 h. The last hydrogenation and dehydrogenation steps were repeated, the reaction time were 10 h and 11 h, respectively.

b) Using 1 mol % complex 1: In a glove box, a 25 mL Schlenk flask was charged with a stirring bar, catalyst 1 (0.01 mmol), KOtBu (0.024 mmol), 2-aminoethanol (1 mmol) and dioxane (4.5 mL) under an atmosphere of nitrogen. The flask was taken out of the glove box, equipped with a condenser and the solution was refluxed with stirring in an open system under a flow of argon for 5 h. After cooling to room temperature, the flask was sealed under a flow of argon and taken into a glove box. 1 mmol of 1,3,5-trimethylbenzene was added to the crude reaction mixture as an internal standard. Then 0.05 mL of the solution was dissolved in CDCl$_3$ for determination of the conversion of 2-aminoethanol by $^1$H NMR spectroscopy. All of the rest solution and precipitate were transferred to a 20 mL Parr apparatus. A catalytic amount of KOtBu (0.024 mmol) was also added to protect the catalyst from trace amount of water, which may be taken into the system during the transfer. The Parr apparatus was taken out of the glove box and subjected to three successive cycles of pressurization/venting with H$_2$ (3 atm), then pressurized with H$_2$ (60 bar) and closed. The Parr apparatus was placed behind a protective shield and the reaction mixture was heated in an oil bath at 110° C. with constant stirring for 5 h. After cooling to room temperature, excess H$_2$ was carefully vented off. The Parr apparatus was taken into the glove box again and 0.05 mL of the solution was dissolved in CDCl$_3$ for determination of the conversion by $^1$H NMR spectroscopy. The reaction mixture was then transferred to a 25 mL Schlenk flask together with 0.024 mmol KOtBu. The flask was taken out of the glove box equipped with a condenser and the solution was refluxed with stirring in an open system under a flow of argon for 11 h. The last hydrogenation and dehydrogenation steps were repeated, the reaction time were 10 h and 11 h, respectively. Results are given in Table 3-NAT.

Example 9

Crystallographic Details

XRD Experimental Details of 1

Crystal data: C$_{20}$H$_{36}$N$_2$O$_1$P$_1$Cl$_1$Ru$_1$ yellow, 0.16×0.06×0.04 mm$^3$, Monoclinic, P2$_1$/c (N14), a=8.856(2), b=18.710(4), c=15.825(5) Å, β=120.92(2)° from 20 degrees of data, T=120(2) K, V=2249.5(10) Å$^3$, Z=4, Fw=488.00, Dc=1.441 Mg·m$^{-3}$, μ=0.898 mm$^{-1}$.

Data collection and processing: Nonius KappaCCD diffractometer, MoKα (λ=0.71073 Å), graphite monochromator, 10136 reflections collected, −11≤h≤11, −24≤k≤24, −20≤l≤20, frame scan width=1°, scan speed 1.0° per 20 sec, typical peak mosaicity 0.47°, 5147 independent reflections (R-int=0.0226). The data were processed with Denzo-Scalepack.

Solution and refinement: Structure solved by direct methods with SHELXS-97. Full matrix least-squares refinement based on F$^2$ with SHELXL-97. 252 parameters with 0 restraints, final R$_1$=0.0417 (based on F$^2$) for data with I>2σ(I) and, R$_1$=0.0518 on 5147 reflections, goodness-of-fit on F$^2$=1.159, largest electron density peak=2.023 Å$^{-3}$, deepest hole −0.760 Å$^{-3}$.

XRD Experimental Details of 2

Crystal data: C$_{19}$H$_{34}$ClN$_2$OPRu, colourless needle, 0.30×0.10×0.04 mm$^3$, monoclinic P2(1)/n, a=8.7861(14) Å, b=18.177(2) Å, c=13.5212(18) Å, α=90 β=91.140(8)°, γ=90 from 3931 reflections, T=100(2) K, V=2159.0(5) Å$^3$, Z=4, Fw=473.97, Dc=1.458 Mg·m$^{-3}$, μ=0.934 mm$^{-1}$.

Data collection and processing: Bruker KappaApexII CCD diffractometer, MoKα (λ=0.71073 Å), graphite monochromator, MiraCol optics, −5≤h≤10, −22≤k≤20, −16≤l≤16, frame scan width=0.5°, scan speed 1.0° per 180 sec, typical peak mosaicity 0.62°, 10953 reflections collected, 4381 independent reflections (R-int=0.037). The data were processed with Bruker Apex2 Suite.

Solution and refinement: Structure solved with SHELXS-97. Full matrix least-squares refinement based on $F^2$ with SHELXL-97 on 241 parameters with 0 restraints gave final $R_1$=0.0292 (based on $F^2$) for data with I>2σ(I) and, $R_1$=0.0427 on 4381 reflections, goodness-of-fit on $F^2$=1.016, largest electron density peak 0.473 e·Å$^{-3}$. Largest hole −0717 e·Å$^{-3}$.

XRD Experimental Details of 3

Crystal data: $C_{23}H_{34}O_1P_1N_2Cl_1Ru_1$, colourless, 0.16× 0.10×0.10 mm$^3$, Monoclinic, P2(1)/c, a=9.785(2) Å, b=10.694(2) Å, c=23.029(5) Å, β=93.83(3)° from 20 degrees of data, T=120(2)K, V=2404.4(8) Å$^3$, Z=4, Fw=522.01, Dc=1.442 Mg·m$^{-3}$, μ=0.846 mm$^{-1}$.

Data collection and processing: Nonius KappaCCD diffractometer, MoKα (λ=0.71073 Å), graphite monochromator, 10258 reflections collected, −12≤h≤12, −13≤k≤13, −29≤l≤29, frame scan width=1°, scan speed 1° per 60 sec, typical peak mosaicity 0.48°, 5300 independent reflections (R-int=0.0399). The data were processed with Denzo-Scalepack.

Solution and refinement: Structure solved by direct methods with SHELXS-97. Full matrix least-squares refinement based on $F^2$ with SHELXL-97. 276 parameters with 1 restraint, final $R_1$=0.0459 (based on $F^2$) for data with I>2σ(I) and, $R_1$=0.0599 on 5300 reflections, goodness-of-fit on $F^2$=1.109, largest electron density peak=2.091 Å$^{-3}$, deepest hole −0.999 Å$^{-3}$.

XRD Experimental Details of 4'

Crystal data: $C_{20}H_{34}O_1P_1N_2K_1Ru_1$, ($C_{20}H_{34}O_1P_1N_2Ru_1+K_1$) black, 0.17×0.05×0.05 mm$^3$, Monoclinic, P2(1)/c, a=14.4472(13) Å, b=24.334(2) Å, c=14.7244(11) Å, β=115.652(3)° from 20 degrees of data, T=100(2)K, V=4665.9(7) Å$^3$, Z=8, Fw=489.63, Dc=1.394 Mg·m$^{-3}$, μ=0.930 mm$^{-1}$.

Data collection and processing: Bruker Apex2 KappaCCD diffractometer, MoKα (λ=0.71073 Å), graphite monochromator, 52954 reflections collected, −17≤h≤17, −29≤k≤22, −17≤l≤17, frame scan width=0.5°, scan speed 1° per 100 sec, typical peak mosaicity 0.69°, 8836 independent reflections (R-int=0.0564). The data were processed with Bruker Apex2 Suite.

Solution and refinement: Structure solved by direct methods with SHELXS-97. Full matrix least-squares refinement based on $F^2$ with SHELXL-97. 493 parameters with 0 restraints, final $R_1$=0.0418 (based on $F^2$) for data with I>2σ(I) and, $R_1$=0.0571 on 8836 reflections, goodness-of-fit on $F^2$=1.062, largest electron density peak=2.483 Å$^{-3}$, deepest hole −0.915 Å$^{-3}$.

Example 10

A LOHC System Based on the Dehydrogenative Coupling of Ethylenediamine and Ethanol The possibility of developing new LOHC systems based on equation (1) using commercially available, inexpensive, and abundant amines and alcohols as hydrogen carriers is described.

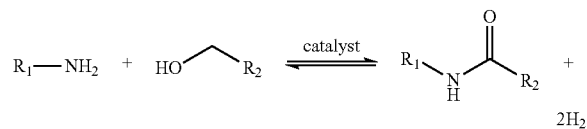

(1)

Reported herein is a LOHC system based on the dehydrogenative coupling of ethylenediamine and ethanol, with a HSC of 5.3 wt % [Eq. (2)].

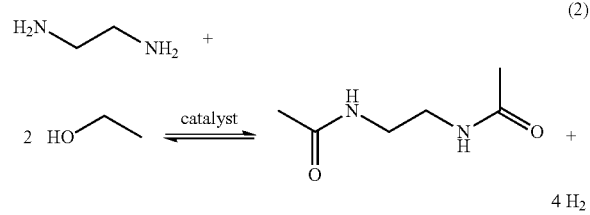

(2)

The system is catalyzed by complex (iii) in the presence of catalytic base, using low catalyst loading (0.2 mol %), and exhibits excellent conversions for both the dehydrogenation and hydrogenation reactions.

a. Dehydrogenative Coupling Reaction of Ethylenediamine (ED) with Ethanol

Initially, the dehydrogenative coupling reaction of ethylenediamine (ED) with ethanol was performed with no added solvent. To a mixture of 10 mmol ED and 24 mmol ethanol, were added 0.01 mmol catalyst (iii) (0.1 mol % relative to ED and 0.04 mol % relative to ethanol) and 0.012 mmol KOtBu (1.2 equiv relative to catalyst (iii), for the generation of the actual catalyst (vi) in situ; FIG. 1). The solution was

TABLE 8

Selected bond distances/angles of 1-3.

| 1 | Distances (Å) | 2 | Distances (Å) | 3 | Distances (Å) |
|---|---|---|---|---|---|
| Ru1—Cl1 | 2.562(1) | Ru—Cl | 2.5623(7) | Ru—Cl | 2.5536(10) |
| Ru—H1A | 1.5126(5) | Ru—H1A | 1.58(3) | Ru—H1 | 1.853(18) |
| Ru1—C20 | 1.841(3) | Ru—C(19) | 1.839(3) | Ru—C(23) | 1.826(4) |
| Ru1—N1 | 2.109(3) | Ru—N(1) | 2.107(2) | Ru—N(1) | 2.100(3) |
| Ru1—N2 | 2.234(3) | Ru—N(2) | 2.200(2) | Ru—N(2) | 2.182(3) |
| Ru1—P1 | 2.2695(9) | Ru—P1 | 2.2728(7) | Ru—P1 | 2.2672(9) |

| 1 | Angles (°) | 2 | Angles (°) | 3 | Angles (°) |
|---|---|---|---|---|---|
| N1—Ru—H1A | 90.7 | N1—Ru—H1A | 88.5(10) | N1—Ru—H1 | 99.4(14) |
| N2—Ru1—P1 | 157.96(7) | N2—Ru—P1 | 157.36(6) | N2—Ru—P1 | 160.18(9) |
| N1—Ru1—C20 | 173.3(1) | N1—Ru—C19 | 174.36(10) | N1—Ru—C23 | 175.15(13) | heated at reflux under argon for 24 h and 47% conversion of ED was achieved, producing the desired product N,N'-diacetylethylenediamine (DAE) in only 2% yield, the monoamide N-(2-aminoethyl)-acetamide (AEA) in 23% yield, and N-ethylidenethane-1,2-diamine (EED) in 22% yield, as determined by $^1$H NMR spectroscopy (Table 9, entry 1).

TABLE 9

Selected results of optimization studies for dehydrogenative coupling of ethylenediamine with ethanol.[a]

| Entry | Cat. [mmol] | ED [mmol] | E [mmol] | Solv. mL | ED conv. [%] | E conv. [%] | DAE yield [%] | AEA yield [%] | Eed yield [%] |
|---|---|---|---|---|---|---|---|---|---|
| 1 | iii (0.01) | 10 | 24 | — | 47 | 20 | 2 | 23 | 22 |
| 2 | iii (0.01) | 12 | 20 | — | 74 | 38 | 17 | 48 | 9 |
| 3 | iii (0.01) | 15 | 20 | — | 74 | 39 | 19 | 49 | 6 |
| 4 | i (0.01) | 15 | 20 | — | 30 | 13 | — | 7 | 22 |
| 5 | iv (0.01) | 15 | 20 | — | 27 | 12 | 1 | 13 | 14 |
| 6 | 1 (0.01) | 15 | 20 | — | 40 | 18 | 2 | 24 | 14 |
| 7 | iii (0.02) | 5 | 12 | dioxane (2) | 100 | 100 | 93 | 7 | — |
| 8 | iii (0.01) | 5 | 12 | dioxane (2) | 100 | 98 | 84 | 16 | — |
| 9[b] | iii (0.01) | 5 | 12 | dioxane (1) | 100 | 100 | 92 | 8 | — |
| 10 | iii (0.01) | 10 | 24 | dioxane (2) | 51 | 23 | 5 | 29 | 17 |
| 11 | iii (0.01) | 5 | 11 | dioxane (1) | 98 | 99 | 78 | 20 | — |
| 12 | iii (0.02) | 10 | 24 | dioxane (1) | 77 | 39 | 16 | 44 | 16 |

[a]Reaction conditions: Catalyst (as specified), KO$^t$Bu (1.2 equiv relative to cat. iii, i, and iv and 2.4 equiv relative to cat. 1), 105° C. (oil bath temperature 135° C.), reflux under Ar for 24 h.
[b]503 mL H$_2$ was collected, amounting to 95% yield based on full conversion of ethylenediamine and ethanol, which would produce 5 mmol N,N'-diacetylethylenediamine, 1 mmol ethyl acetate, and 22 mmol H$_2$.
ED = ethylenediamine,
E = ethanol,
DAE = N,N'-diacetylethylenediamine,
AEA = N-(2-aminoethyl)acetamide,
EED = N-ethylideneethane-1,2-diamine Using ED in excess, higher conversion of both ethanol and ED were achieved, resulting in 17% yield of the desired DAE (Table 9, entry 2). Increasing the amount of ED from 12 mmol to 15 mmol did not significantly improve the results (Table 9, entry 3). Using catalysts (i), (iv) and (1) under conditions similar to those of entry 3 resulted in inferior performance relative to that achieved with catalyst (iii) (Table 9, entries 4-6). Introducing dioxane as a solvent and increasing the catalyst loading of (iii) to 0.4 mol % (based on ED) dramatically improved the reaction. Using 5 mmol of ED, 12 mmol of ethanol, and 2 mL of dioxane resulted in full conversions of ED and ethanol, DAE in 93% yield and AEA in 7% yield (Table 9, entry 7). Lower catalyst loading (0.2 mol % based on ED and 0.08 mol % based on ethanol) did not influence conversions of the reactants and produced DAE in 84% yield (Table 9, entry 8). Note that the employed excess of ethanol (20% relative to ED) releases hydrogen by itself, by self-dehydrogenative coupling to give ethyl acetate as the product. Interestingly, when only 1 mL of dioxane was used, full conversions of ethanol and ED were achieved, and 92% yield of DAE was provided (Table 9, entry 9). Moreover, 503 mL of hydrogen was collected, amounting to 95% yield based on full conversion of ethanol and ED, which can produce 5 mmol DAE, 1 mmol ethyl acetate, and 22 mmol H$_2$. Efforts to decrease the catalyst loading and the amount of solvent were ineffective (Table 9, entries 10-12).

b. Hydrogenation of N,N'-diacetylethylenediamine (DAE) to ED and Ethanol

Next the hydrogenation of N,N'-diacetylethylenediamine (DAE) to ED and ethanol was persued. Using 1 mol % complex (iii), 1.2 mol % KOtBu, 0.5 mmol DAE in 1 mL dioxane under 40 bar of hydrogen for 24 h resulted in 63% yield of ED and 35% yield of AEA, as determined by $^1$H NMR spectroscopy (Table 10, entry 1). When 50 bar of hydrogen were applied, 84% yield of ED was obtained (Table 10, entry 2). A longer reaction time of 48 h improved the yield of ED to 91% and full conversion of DAE was achieved (Table 10, entry 3). A higher amount of base was beneficial (Table 10, entries 4 and 5); full conversion of DAE and excellent yield of ED were obtained even at a lower catalyst loading of 0.5 mol % after 24 h (Table 10, entry 5). Further optimization of the catalyst loading indicated that using 0.2 mol % of catalyst (iii) also resulted in good yield of ED after 48 h (Table 10, entry 6). Increasing the amount of base from 2.4 equiv to 5 equiv (relative to catalyst (iii)) slightly improved the yield of ED (Table 10, entry 7). Complex (1) also showed good catalytic activity for the hydrogenation reaction, but it was not as efficient as catalyst iii (Table 10, entry 6 vs. entry 8). When 70 bar of hydrogen and 0.2 mol % of catalyst iii were applied, full conversion of DAE and 92% yield of ED were achieved after 48 h (Table 10, entry 9). Using ethanol as solvent instead of dioxane resulted in low yields of ED and AEA (Table 10, entry 10). Employing 0.4 mol % catalyst iii, a larger scale (5 mmol DAE) hydrogenation reaction was tried in less solvent (2 mL) under 70 bar of hydrogen, leading to quantitative yield of ED in just 10 h (Table 10, entry 11).

TABLE 10

Selected results from the optimization studies for the hydrogenation of N,N'-diacetylethylenediamine.[a]

| Entry | Cat. [mol%] | KOtBu [equiv to cat.] | DAE [mmol] | t [h] | Products [% yield] |
|---|---|---|---|---|---|
| 1[b,c] | iii (1) | 1.2 | 0.5 | 24 | ED (63) + AEA (35) + E (55) |
| 2[b] | iii (1) | 1.2 | 0.5 | 24 | ED (84) + AEA (15) + E (68) |
| 3[b] | iii (1) | 1.2 | 0.5 | 48 | ED (91) + AEA (9) + E (70) |
| 4[b] | iii (1) | 2.4 | 0.5 | 24 | ED (89) + AEA (11) + E (71) |
| 5 | iii (0.5) | 2.4 | 1 | 24 | ED (91) + AEA (9) + E (79) |
| 6 | iii (0.2) | 2.4 | 1 | 48 | ED (77) + AEA (22) + E (69) |
| 7 | iii (0.2) | 5 | 1 | 48 | ED (82) + AEA (18) + E (71) |
| 8 | 1 (0.2) | 2.4 | 1 | 48 | ED (71) + AEA (28) + E (61) |
| 9[d] | iii (0.2) | 2.4 | 1 | 48 | ED (92) + AEA (8) + E (73) |
| 10[e] | iii (1) | 2.4 | 0.5 | 48 | ED (trace) + AEA (14) + E (−) |
| 11[d] | iii (0.4) | 2.4 | 5 | 10 | ED (>99) + E (89) |

[a]Reaction conditions: Catalyst, KO$^t$Bu, N,N'-diacetylethylenediamine, dioxane (2 mL), and H$_2$ (50 bar) were heated in a 20 mL Parr apparatus at 115° C. (oil bath temperature). Yields were determined by NMR analysis. The relatively lower yields of ethanol are probably due to the evaporation loss during the reaction and workup.
[b]1 mL dioxane was used.
[c]40 bar H$_2$ was used.
[d]70 bar H$_2$ was used.
[e]1 mL ethanol was used as solvent, 47% yield of N-ethylideneethane-1,2-diamine was observed, the conversion of DAE was 61%.

c. Repetitive Reversal Reactions

Repetitive reversal reactions were also tried with no addition of new catalyst, in shorter dehydrogenation and hydrogenation periods of 12 h and 10 h, respectively (Table 11, see below for details). The cycles began with dehydrogenation, using 0.4 mol % catalyst (iii), 0.48 mol % KOtBu, 5 mmol ED, 12 mmol ethanol, and 2 mL dioxane. After the first dehydrogenation reaction, which resulted in 99% conversion of ED, the crude reaction mixture was transferred to a 20 mL Parr apparatus for hydrogenation. The catalytic activity of the system did not decrease and full conversion was observed. Following, the second dehydrogenation step resulted in 92% conversion of ED, while the second hydrogenation step also provided 100% of ED. The performance of the third cycle was also good; even after the catalyst had been used six times, 100% ED was still observed at the end of the third hydrogenation step.

TABLE 11

Repetitive cycles of the dehydrogenation-hydrogenation reactions.

| Cycle | Conversion of dehydrogenation (%)[a] | Conversion of hydrogenation (%)[a] |
|---|---|---|
| 1 | 99 | 100 |
| 2 | 92 | 100 |
| 3 | 88 | 100 |

[a]Based on the amount of ethylenediamine in the system.

In summary, an efficient and simple homogeneous LOHC system was developed, using ethylenediamine and ethanol as the hydrogen carriers. Employing a low catalyst loading of 0.2 mol %, complex (iii) catalyzed both the unloading and the loading of hydrogen in excellent yields; no stoichiometric additives were needed. High concentrations of substrates (5 mol ethylenediamine/mL dioxane and 12 mol ethanol/mL dioxane) could be applied and the efficiency of the reaction did not decrease. The repetitive reactions catalyzed by 0.4 mol % catalyst exhibited excellent conversions in three cycles. Ethylenediamine and ethanol, which are inexpensive and extensively produced by industry, can provide, upon further development, a new simple LOHC system, which is quite different from the existing hydrogen storage systems. Ongoing research will focus on increasing the efficiency of the current system (e.g. using no solvent), and developing other amine-alcohol systems with even higher HSCs (for example, ethylenediamine and methanol).

Example 11

Mechanistic Study

Based on previous research on dehydrogenation reactions and the above results, a simplified mechanism for the dehydrogenative amidation of ED and ethanol is shown in Scheme 20.

Scheme 20. Proposed pathway for the dehydrogenation of ethylenediamine and ethanol.

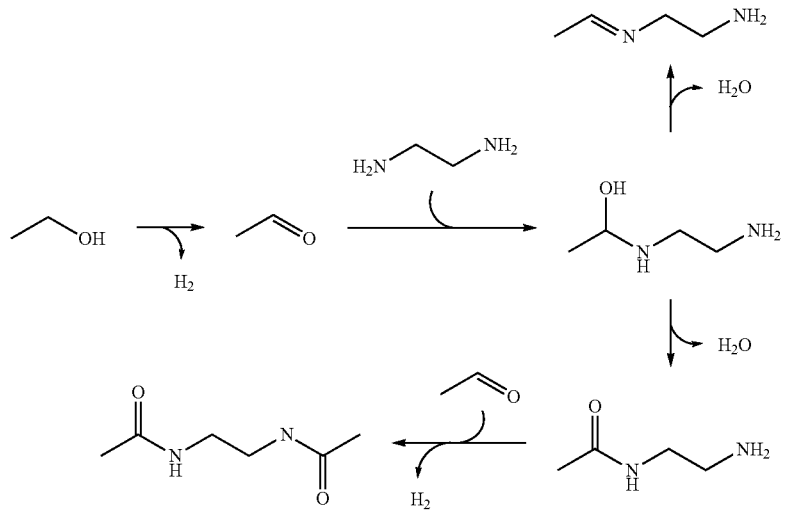

Dehydrogenation of ethanol forms acetaldehyde as an intermediate, which reacts with one amine group of ED to form a hemiaminal intermediate. The latter undergoes competitive elimination of water to produce N-ethylidenethane-1,2-diamine and elimination of hydrogen to form N-(2-aminoethyl)acetamide. Reaction of N-(2-aminoethyl)acetamide with another molecule of acetaldehyde and release of one molecule of hydrogen leads to N,N'-diacetylethylenediamine as the product.

Example 12

General Experimental Protocols for the Ethylenediamine/Ethanol System

General Procedure for the Dehydrogenation of Ethylenediamine and Ethanol

In a glove box, a 25 mL Schlenk flask was charged with a stirring bar, catalyst (0.01-0.02 mmol), KOtBu (0.012-0.024 mmol), ethylenediamine (5-15 mmol), ethanol (11-24 mmol) and dioxane (0-2 mL) under an atmosphere of nitrogen. The flask was taken out of the glove box, equipped with a condenser, and the solution was refluxed in a fume hood with stirring in an open system under a flow of argon for 24 h. After cooling to room temperature, 1 mmol of 1,3,5-trimethylbenzene was added to the crude reaction mixture as an internal standard. Then 0.05 mL of the solution was dissolved in CDCl$_3$ for determination of the conversion of ethylenediamine by $^1$H NMR spectroscopy. To the rest of the crude reaction mixtures was added 2-3 mL water, leading to a homogeneous solution. 5 mmol of pyridine was then added as an internal standard and 0.05 mL of the solution was analyzed by $^1$H NMR spectroscopy to determine the yield of N,N'-S2-diacetylethylenediamine (DAE), N-(2-aminoethyl)acetamide (AEA) and Nethylideneethane-1,2-diamine (EED), using D$_2$O as the solvent.

General Procedure for the Hydrogenation of N,N'-diacetylethylenediamine:

In a glove box, a 20 mL Parr apparatus was charged with the catalyst (0.005-0.02 mmol), KOtBu (0.006-0.048 mmol), N,N'-diacetylethylenediamine (0.5-5 mmol) and dioxane (1-2 mL) under an atmosphere of purified nitrogen. The pressure equipment was taken out of the glove box, placed in a fume hood and subjected to three successive cycles of pressurization/venting with H$_2$ (3 atm), then pressurized with H$_2$ (40-70 bar) behind a protective shield and closed. The reaction mixture was heated behind the protective shield in an oil bath at 115° C. with constant stirring for 10-48 h. After cooling to room temperature, excess H$_2$ was carefully vented off. 0.5-5 mmol of 1,3,5-trimethylbenzene was added to the crude reaction mixture as an internal standard. Then 0.05 mL of the solution was dissolved in CDCl$_3$ for determination of the yield of ethylenediamine (ED) and N-(2-aminoethyl)acetamide (AEA) by $^1$H NMR spectroscopy.

Figure 12:
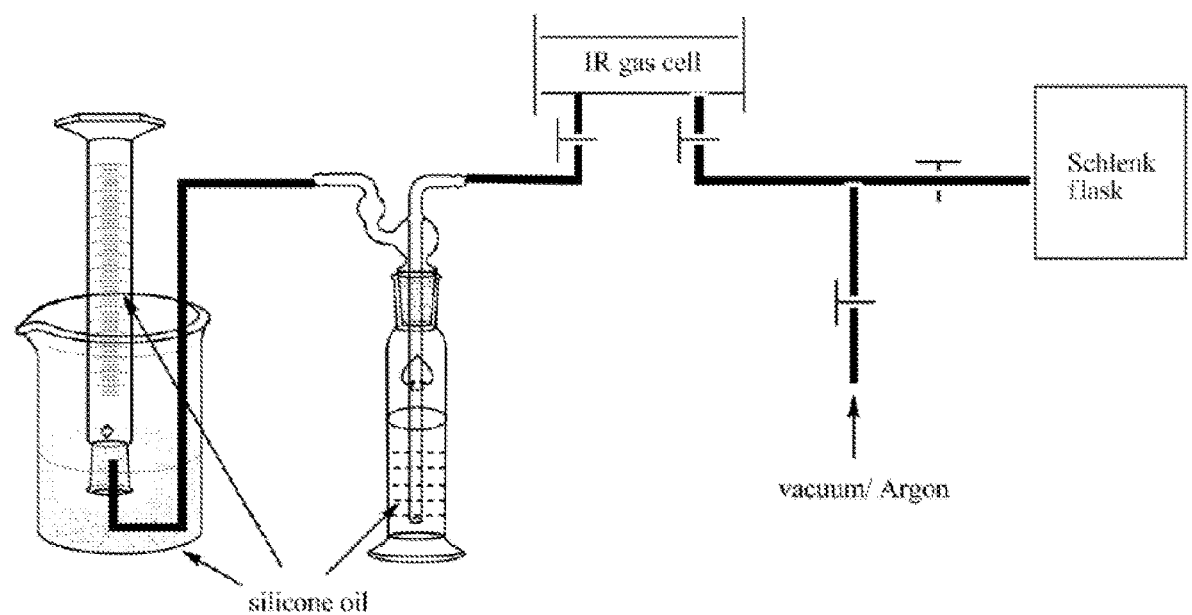
FIG. 12: Schematic drawing of the gas collection system for the diaminoalkane/alcohol LOHC system.

General Procedure for Gas Collection:

In a glove box, a 25 mL Schlenk flask was charged with a stirring bar, catalyst (iii) (0.01 mmol), KOtBu (0.012 mmol), ethylenediamine (5 mmol), ethanol (12 mmol) and dioxane (1 mL) under an atmosphere of nitrogen. The flask was taken out of the glove box, placed in a fume hood and equipped with a reflux condenser and connected to a gas collection system under a flow of argon. The whole open system was flushed with argon and then connected to an inverted graduated cylinder filled with silicon oil (see FIG. 12). The solution was refluxed with stirring. After 24 h the volume of the generated gas was recorded as V1 and the valves of the IR gas cell and the Schlenk flask were closed. The gas in the IR gas cell was analyzed by GC and IR. To quantify the effect of warming on the gas volume, the condenser was disconnected from the gas collection system and opened in the air. After the flask was cooled to room temperature, the condenser was connected to the gas collection system again. The solvent was refluxed for another 0.5 h until no gas bubbles (as a result of argon expansion) were observed, and the increased volume of gas in the flask when heating was recorded as V2. The volume of H$_2$ produced was V1-V2. The molar volume of hydrogen at 20° C. and 1 atm pressure is taken as 24.1 L.

Procedure for the Repetitive Reversal Reactions:

In a glove box, a 25 mL Schlenk flask was charged with a stirring bar, catalyst (iii) (0.02 mmol), KOtBu (0.024 mmol), ethylenediamine (5 mmol), ethanol (12 mmol) and dioxane (2 mL) under an atmosphere of nitrogen. The flask was taken out of the glove box, equipped with a condenser and the solution was refluxed with stirring in an open system under a flow of argon for 12 h. After cooling to room temperature, the flask was sealed under a flow of argon and taken into a glove box. 1.5 mmol of 1,3,5-trimethylbenzene was added to the crude reaction mixture as an internal standard. Then 0.05 mL of the solution was dissolved in CDCl₃ for determination of the conversion of ethylenediamine by ¹H NMR spectroscopy. The rest of the solution and precipitate were transferred to a 20 mL Parr apparatus. A catalytic amount of KO$^t$Bu (0.024 mmol) was also added to protect the catalyst from trace amount of water, which may be taken into the system during the course of transfer. The Parr apparatus was taken out of the glove box and subjected to three successive cycles of pressurization/venting with H₂ (3 atm), then pressurized with H₂ (70 bar) and closed. The Parr apparatus was placed behind a protective shield and the reaction mixture was heated in an oil bath at 115° C. with constant stirring for 10 h. After cooling to room temperature, excess H₂ was carefully vented off. The Parr apparatus was taken into the glove box again and 0.05 mL of the solution was dissolved in CDCl₃ for determination of the conversion by ¹H NMR spectroscopy. The reaction mixture was then transferred to a 25 mL Schlenk flask together with 0.024 mmol KO$^t$Bu. The flask was taken out of the glove box equipped with a condenser and the solution was refluxed with stirring in an open system under a flow of argon for 12 h. The hydrogenation and dehydrogenation cycles were repeated.

N-(2-aminoethyl)acetamide was reported and fully characterized.

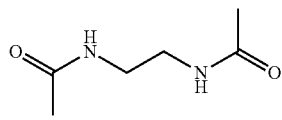

¹H NMR (D₂O): 3.26 (s, 4 H), 1.95 (s, 6 H). ¹³C{1H} NMR (D₂O): 174.30, 38.52, 21.72. HRMS calcd for C₆H₁₂N₂O₂Na [M+Na]⁺: 167.0796, found: 167.0794.

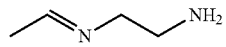

¹H NMR (D₂O): 3.01-2.95 (m, 2 H), 2.79-2.15 (m, 2 H), 1.24 (dd, J=6.0, 1.3 Hz, 3 H) MS: 87.1 [M+H]+.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A process for the storage and release of hydrogen (H₂) upon demand, comprising the steps of:
   (a) when hydrogen storage is desired, reacting glycine anhydride (GA), N,N-dimethyl GA, or N,N'-diacetylethylenediamine (DAE), with hydrogen (H₂) in the presence of a first catalyst, under conditions sufficient to generate 2-aminoethanol (AE), 2-(methylamino) ethanol, or ethylenediamine (ED) and ethanol respectively; and
   (b) when hydrogen release is desired, reacting 2-aminoethanol (AE), 2-(methylamino) ethanol, or ethylenediamine (ED) and ethanol, with a second catalyst, under conditions sufficient to generate glycine anhydride, N,N-dimethyl GA, or N,N'-diacetylethylenediamine (DAE) respectively, and hydrogen (H₂), wherein the first catalyst and the second catalyst may be the same or different.

2. The process according to claim 1, wherein said first catalyst and said second catalyst are the same.

3. The process according to claim 1, wherein step (b) generates a mixture of (i) glycine anhydride or N,N-dimethyl GA; and (ii) a linear peptide represented by the structure:

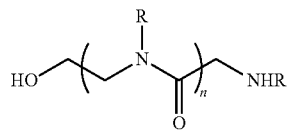

wherein R is H or CH₃, and n is an integer of 1-11,
wherein said mixture is capable of being hydrogenated back to 2-aminoethanol (AE) or 2-(methylamino) ethanol if desired; or
wherein said reaction of ethylenediamine (ED) with ethanol further generates N-(2-aminoethyl)-acetamide (AEA); and/or N-ethylidenethane-1,2-diamine (EED), resulting in a mixture of DAE, AEA and EED), wherein said mixture is capable of being hydrogenated back to ED and ethanol if desired.

4. The process according to claim 1, wherein the reaction mixture of said reaction of glycine anhydride (GA) or N,N-dimethyl GA with hydrogen (H₂) further comprises a linear peptide represented by the structure:

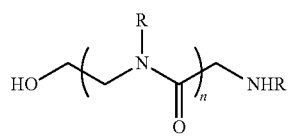

wherein R is H or CH₃, and n is an integer of 1-11, so as to form 2-aminoethanol (AE) or 2-(methylamino) ethanol; or
wherein the reaction mixture of said reaction of N,N'-diacetylethylenediamine (DAE) with hydrogen (H₂) further comprises N-(2-aminoethyl)-acetamide (AEA) and/or N-eth lidenethane-1,2-diamine (EED), so as to form ED and ethanol.

5. The process according to claim 1, wherein the first or second catalyst is a Ruthenium complex represented by the structure of any of formulae A1, A2 and A3:

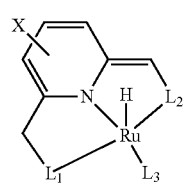

A1

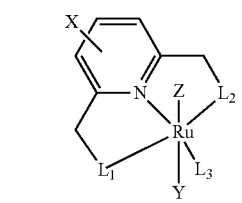

A2

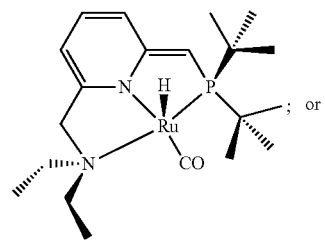

(II)

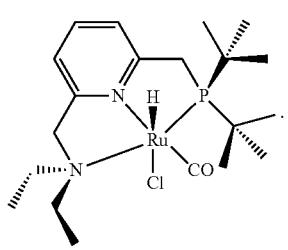

formula (i):

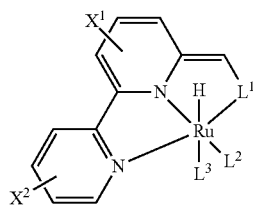

(i)

A3 wherein

L₁ and L₂ are each independently selected from the group consisting of nucleophilic carbene (:C(R)₂), P(R)₂, P(OR)₂, N(R)₂, imine, SR, SH, S(=O)R, heteroaryl wherein the heteroatom is selected from nitrogen and sulfur, As(R)₂, Sb(R)₂ and an N-heterocyclic carbene represented by the structure:

7. The process according to claim 1, wherein the catalyst is a Ruthenium complex represented by the structure of any of formulae A1', A2' and A3':

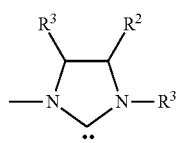

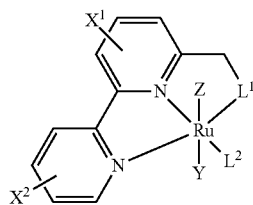

A1' each of R, R² and R³ are independently selected from the group consisting of alkyl, cycloalkyl, aryl, alkylaryl, heterocyclyl and heteroaryl;

L₃ is a mono-dentate two-electron donor selected from the group consisting of CO, P(R)₃, P(OR)₃, NO⁺, As(R)₃, Sb(R)₃, S(R)₂, nitrile (RCN) and isonitrile (RNC) wherein R is as defined above;

L₄ is absent or is L₃;

Y and Z are each independently H or an anionic ligand selected from the group consisting of halogen, OCOR, OCOCF₃, OSO₂R, OSO₂CF₃, CN, OH, OR, N(R)₂, RS and SH; wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety; and anion represents a group bearing a single negative charge.

6. The process according to claim 5, wherein the Ruthenium complex is represented by the structure of formula (ii):

A2'

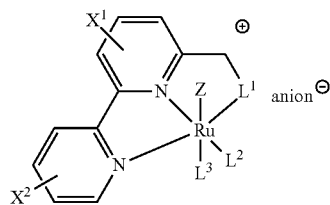

A3' wherein

L¹ is selected from the group consisting of phosphine (PR$^a$R$^b$), phosphite P(OR$^a$)(OR$^b$), phosphinite P(OR$^a$)(R$^b$), amine (NR$^a$R$^b$), imine, oxazoline, sulfide (SR$^a$), sulfoxide (S(=O)R$^a$), heteroaryl containing at least one heteroatom selected from nitrogen and sulfur; arsine (AsR$^a$R$^a$R$^b$), stibine (SbR$^a$R$^b$) and a N-heterocyclic carbene represented by the structures:

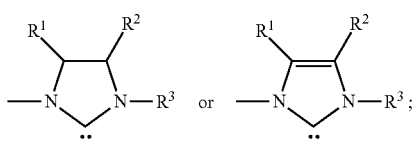

L² is a mono-dentate two-electron donor selected from the group consisting of CO, $PR^aR^bR^c$, $P(OR^a)(OR^b)(OR^c)$, $NO^+$, $AsR^aR^bR^c$, $SbR^aR^bR^c$, $SR^aR^b$, nitrile (RCN), isonitrile (RNC), $N_2$, $PF_3$, CS, heteroaryl, tetrahydrothiophene, alkene and alkyne;

L³ is absent or is L²;

Y and Z are each independently H or an anionic ligand selected from the group consisting of H, halogen, OCOR, $OCOCF_3$, $OSO_2R$, $OSO_2CF_3$, CN, OR, $N(R)_2$ and RS;

$R^a$, $R^b$ and $R^c$ are each independently alkyl, cycloalkyl, aryl, heterocyclyl, heteroaryl, alkylcycloalkyl, alkylaryl, alkylheterocyclyl or alkylheteroaryl; R, $R^1$, $R^2$ and $R^3$ are each independently H, alkyl, cycloalkyl, aryl, heterocyclyl, heteroaryl, alkylcycloalkyl, alkylaryl, alkylheterocyclyl or alkylheteroaryl;

$X^1$ represents zero, one, two or three substituents and $X^2$ represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety; and anion represents a group bearing a single negative charge;

or a borane derivative of said complex.

8. The process according to claim 7, wherein the Ruthenium complex is represented by the structure of formula (iii):

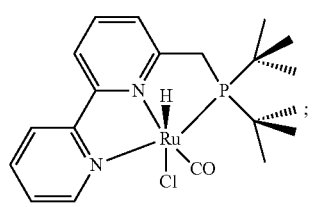

formula (iv):

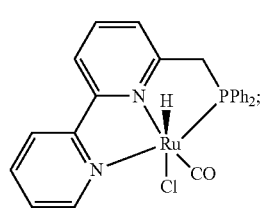

formula (v):

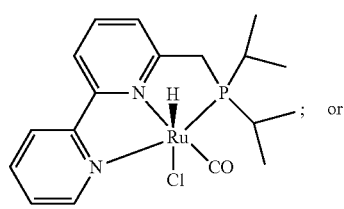

formula (vi):

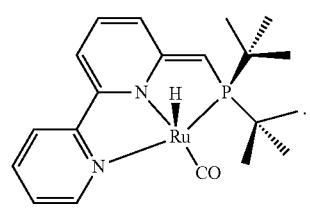

9. The process according to claim 1, wherein the catalyst is a Ruthenium complex represented by the structure of any of formulae A1", A2", A3" or A4":

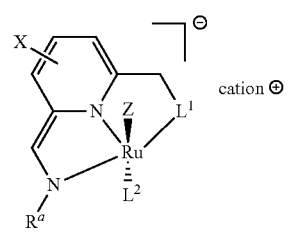

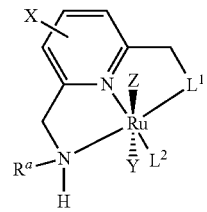

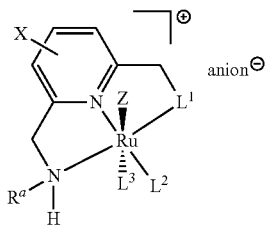

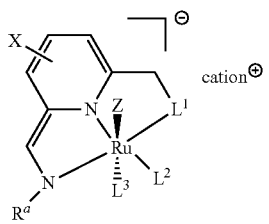

wherein
L¹ is selected from the group consisting of phosphine (PR$^b$R$^c$), phosphite P(OR$^b$)(OR$^c$), phosphinite P(OR$^b$)(R$^c$), amine (NR$^b$R$^c$), imine, oxazoline, sulfide (SR$^b$), sulfoxide (S(=O)R$^b$), heteroaryl containing at least one heteroatom selected from nitrogen and sulfur; arsine (AsR$^b$R$^c$), stibine (SbR$^b$R$^c$) and a N-heterocyclic carbene represented by the structures:

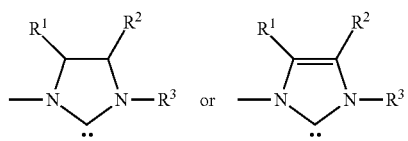

L² is a mono-dentate two-electron donor selected from the group consisting of CO, PR$^b$R$^c$R$^d$, P(OR$^b$)(OR$^c$)(OR$^d$), NO⁺, AsR$^b$R$^c$R$^d$, SbR$^b$R$^c$R$^d$, SR$^b$R$^c$, nitrile (RCN), isonitrile (RNC), N$_2$, PF$_3$, CS, heteroaryl, tetrahydrothiophene, alkene and alkyne;

L³ is absent or is L²;

Y and Z are each independently H or an anionic ligand selected from the group consisting of H, halogen, OCOR, OCOCF$_3$, OSO$_2$R, OSO$_2$CF$_3$, CN, OR, N(R)$_2$ and RS;

R$^a$ is H, alkyl, cycloalkyl, aryl, heterocyclyl, heteroaryl, alkylcycloalkyl, alkylaryl, alkylheterocyclyl or alkylheteroaryl;

R$^b$, R$^c$ and R$^d$ are each independently alkyl, cycloalkyl, aryl, heterocyclyl, heteroaryl, alkylcycloalkyl, alylaryl, alkylheterocyclyl or alkylheteroaryl;

R, R¹, R² and R³ are each independently H, alkyl, cycloalkyl, aryl, heterocyclyl, heteroaryl, alkylcycloalkyl, alkylaryl, alkylheterocyclyl or alkylheteroaryl;

X represents zero, one, two or three substituents independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety;

anion ⊖ represents a group bearing a single negative charge; and cation ⊕ represents a group bearing a single positive charge.

10. The process according to claim 9, wherein the Ruthenium complex is represented by the structure of formula :

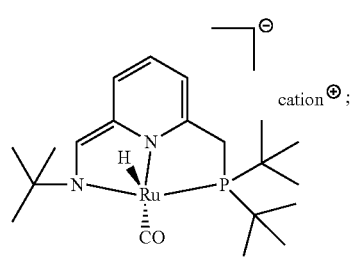

formula 1

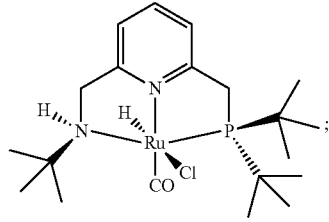

formula 2:

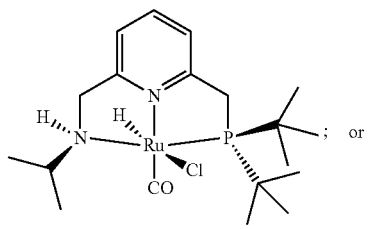

formula 3:

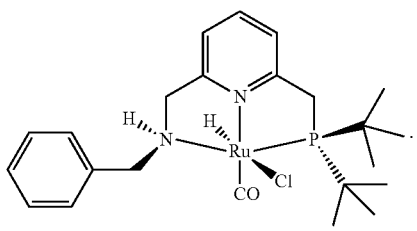

11. The process of claim 1, wherein the catalyst is further attached through any available positions to a solid support, or wherein the catalyst is embedded or a solid support, or is located on the surface of a solid support.

12. The process according to claim 11, wherein the solid support comprises an inorganic material selected from the group consisting of silica, alumina, magnesia, titania, zirconia, montmorillonite, phyllosilicate, zeolites, talc, clays, layered double hydroxides, apatites, and any combination thereof; an organic polymer selected from polystyrene, polyethylene, polypropylene, polyvinylchloride, polytetrafluoro ethylene, polyacrylic acid methylester, polymethacrylic acid methylester, polycarbonates, polyethylene glycol, polyethylene terephthalate, poly(organo)siloxanes, and combinations thereof.

13. The process of claim 1, further comprising a solvent, a catalytic amount of base, or combination thereof.

14. The process according to claim 13, wherein said solvent is dioxane, THF or a mixture thereof; said base is potassium t-butoxide; said catalytic amount of base is between 1-3 equivalents with respect to the catalyst, said catalyst is in an amount of 0.4% (mol %) with respect to the reactant (i.e., AE, 2-(methylamino) ethanol, GA, N,N-dimethyl GA, diaminoalkane, alcohol ED, ethanol, or DAE); or any combination thereof.

15. A process for the storage of hydrogen (H$_2$), the process comprises reacting glycine anhydride (GA), N,N-dimethyl GA, or N,N'-diacetylethylenediamine (DAE) with molecular hydrogen (H$_2$) in the presence of a first catalyst, under conditions sufficient to generate 2-aminoethanol (AE), 2-(methylamino) ethanol, or ethylenediamine (ED) and ethanol respectively, as a hydrogen storage system.

16. The process according to claim 15, wherein the reaction mixture of said reaction of glycine anhydride (GA) or N,N-dimethyl GA with hydrogen (H$_2$) further comprises a linear peptide represented by the structure:

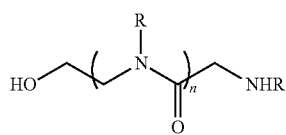

wherein R is H or CH$_3$, and n is an integer of 1-11, so as to form 2-aminoethanol (AE) or 2-(methylamino) ethanol.

17. The process according to claim 15, wherein the first catalyst is a Ruthenium complex represented by the structure of any of formulae A1, A2 and A3:

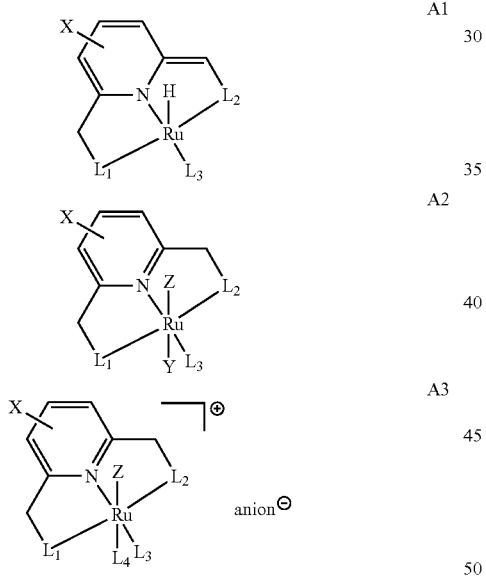

wherein
L$_1$ and L$_2$ are each independently selected from the group consisting of nucleophilic carbene (:C(R)$_2$), P(R)$_2$, P(OR)$_2$, N(R)$_2$, imine, SR, SH, S(=O)R, heteroaryl wherein the heteroatom is selected from nitrogen and sulfur, As(R)$_2$, Sb(R)$_2$ and an N-heretocyclic carbene represented by the structure:

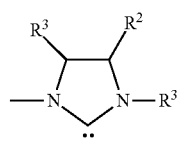

each of R, R$^2$ and R$^3$ are independently selected from the group consisting of alkyl, cycloalkyl, aryl, alkylaryl, heterocyclyl and heteroaryl;

L$_3$ is a mono-dentate two-electron donor selected from the group consisting of CO, P(R)$_3$, P(OR)$_3$, NO$^+$, As(R)$_3$, Sb(R)$_3$, S(R)$_2$, nitrile (RCN) and isonitrile (RNC) wherein R is as defined above;

L$_4$ is absent or is L$_3$;

Y and Z are each independently H or an anionic ligand selected from the group consisting of halogen, OCOR, OCOCF$_3$, OSO$_2$R, OSO$_2$CF$_3$, CN, OH, OR, N(R)$_2$, RS and SH; wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety; and anion represents a group bearing a single negative charge.

18. The process according to claim 17, wherein the Ruthenium complex is represented by the structure of formula (ii):

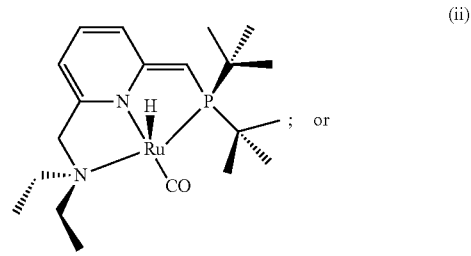

formula (i):

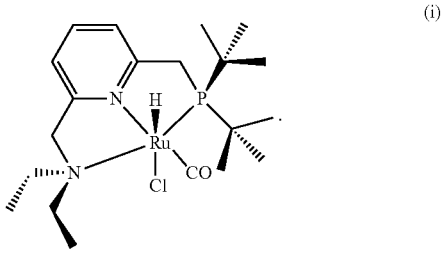

19. The process according to claim 15, wherein the catalyst is a Ruthenium complex represented by the structure of any of formulae A1', A2', and A3':

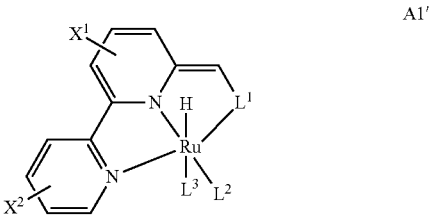

-continued

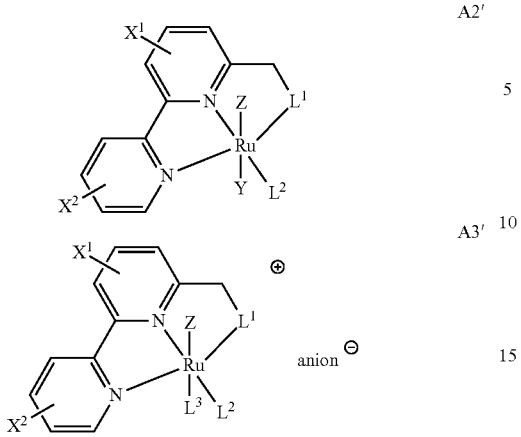

wherein
- L¹ is selected from the group consisting of phosphine (PR$^a$R$^b$), phosphite P(OR$^a$)(OR$^b$), phosphinite P(OR$^a$)(R$^b$), amine (NR$^a$R$^b$), imine, oxazoline, sulfide (SR$^a$), sulfoxide (S(=O)R$^a$), heteroaryl containing at least one heteroatom selected from nitrogen and sulfur; arsine (AsR$^a$R$^b$), stibine (SbR$^a$R$^b$) and a N-heterocyclic carbene represented by the structures:

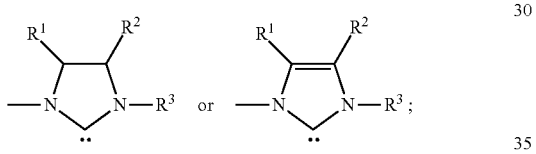

- L² is a mono-dentate two-electron donor selected from the group consisting of CO, PR$^a$R$^b$R$^c$, P(OR$^a$)(OR$^b$)(OR$^c$), NO$^+$, AsR$^a$R$^b$R$^c$, SbR$^a$R$^b$R$^c$, SR$^a$R$^b$, nitrile (RCN), isonitrile (RNC), N$_2$, PF$_3$, CS, heteroaryl, tetrahydrothiophene, alkene and alkyne;
- L³ is absent or is L²;
- Y and Z are each independently H or an anionic ligand selected from the group consisting of H, halogen, OCOR, OCOCF$_3$, OSO$_2$R, OSO$_2$CF$_3$, CN, OR N(R)$_2$ and RS;
- R$^a$, R$^b$ and R$^c$ are each independently alkyl, cycloalkyl, aryl, heterocyclyl, heteroaryl, alkylcycloalkyl, alkylaryl, alkylheterocyclyl or alkylheteroaryl;
- R, R¹, R² and R³ are each independently H, alkyl, cycloalkyl, aryl, heterocyclyl, heteroaryl, alkylcycloalkyl, alkylaryl, alkylheterocyclyl or alkylheteroaryl;
- X¹ represents zero, one, two or three substituents and X² represents zero, one, two, three or four substituents, wherein each such substituent is independently selected from the group consisting of alkyl, cycloalkyl, aryl, heterocyclyl, heteroaryl, alkylcycloalkyl, alkylaryl, alkylheterocyclyl, alkylheteroaryl, halogen, nitro, amide, ester, cyano, alkoxy, alkylamino, arylamino, an inorganic support and a polymeric moiety; and anion represents a group bearing a single negative charge;
or a borane derivative of said complex.

20. The process according to claim 19, wherein the Ruthenium complex is represented by the structure of formula (iii):

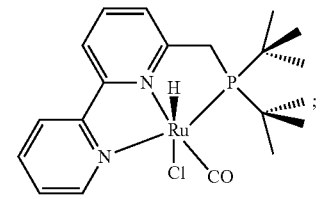

formula (iv):

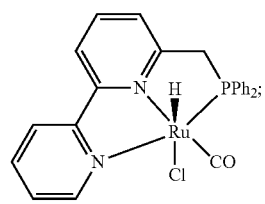

formula (v):

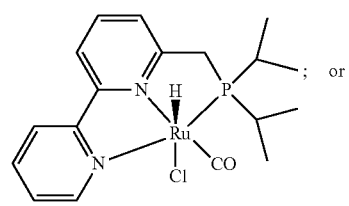

formula (vi):

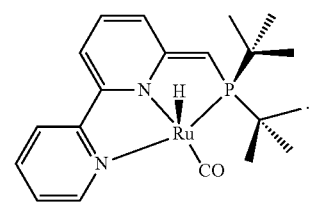

21. The process according to claim 15, wherein the catalyst is a Ruthenium complex represented by the structure of any of formulae A1″, A2″, A3″ or A4″:

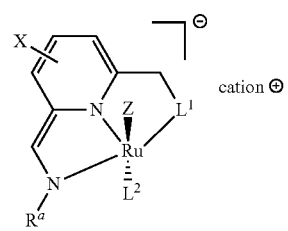

-continued

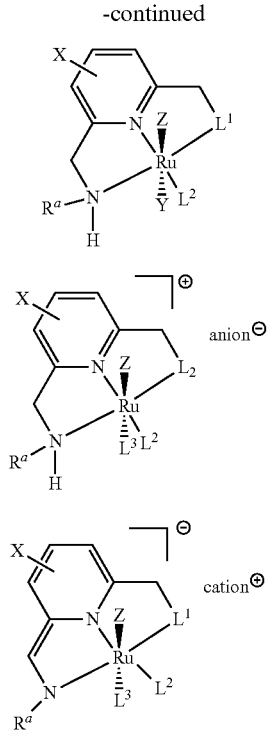

wherein
L¹ is selected from the group consisting of phosphine (PR$^b$R$^c$), phosphite P(OR$^b$)(OR$^c$), phosphinite P(OR$^b$)(R$^c$), amine (NR$^b$R$^c$), imine, oxazoline, sulfide (SR$^b$), sulfoxide (S(=O)R$^b$), heteroaryl containing at least one heteroatom selected from nitrogen and sulfur; arsine (AsR$^b$R$^c$), stibine)(SbR$^b$R$^c$) and a N-heterocyclic carbene represented by the structures:

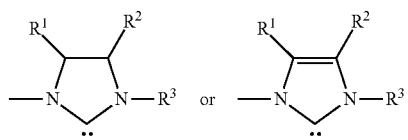

L² is a mono-dentate two-electron donor selected from the group consisting of CO, PR$^b$R$^c$R$^d$, P(OR$^b$)(OR$^c$)(OR$^d$), NO⁺, AsR$^b$R$^c$R$^d$, SbR$^b$R$^c$R$^d$, SR$^b$R$^c$, nitrile (RCN), isonitrile (RNC), N₂, PF₃, CS, heteroaryl, tetrahydrothiophene, alkene and alkyne;
L³ is absent or is L²;
Y and Z are each independently H or an anionic ligand selected from the group consisting of H, halogen, OCOR, OCOCF₃, OSO₂R, OSO₂CF₃, CN, OR, N(R)₂ and RS;
R$^a$ is H, alkyl, cycloalkyl, aryl, heterocyclyl, heteroaryl, alkylcycloalkyl, alkylaryl, alkylheterocyclyl or alkylheteroaryl;
R$^b$, R$^c$ and R$^d$ are each independently alkyl, cycloalkyl, aryl, heterocyclyl, heteroaryl, alkylcycloalkyl, alkylaryl, alkylheterocyclyl or alkylheteroaryl;
R,R¹R² and R³ are each independently H, alkyl, cycloalkyl, aryl, heterocyclyl, heteroaryl, alkylcycloalkyl, alkylaryl, alkylheterocyclyl or alkylheteroaryl;

X represents zero, one, two or three substituents independently selected from the group consisting of alkyl, cycloalkyl, aryl, heterocyclyl, heteroaryl, alkyl cycloalkyl, alkylaryl, alkylheterocyclyl, alkylheteroaryl, halogen, nitro, amide, ester, cyano, alkoxy, alkylamino, arylamino, an inorganic support and a polymeric moiety;
anion ⊖ represents a group bearing a single negative charge; and
cation ⊕ represents a group bearing a single positive charge.

22. The process according to claim 21, wherein the Ruthenium complex is represented by the structure of formula 4:

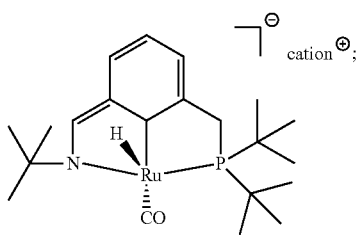

formula 1:

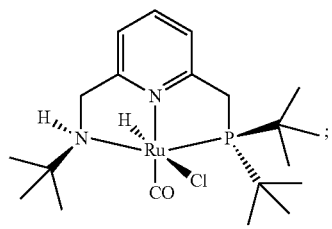

formula 2:

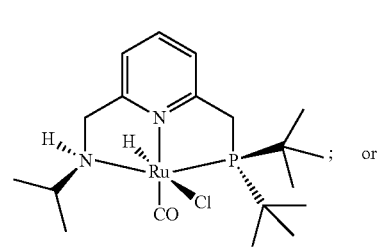

formula 3:

23. The process of claim 15, wherein the catalyst is further attached through any available positions to a solid support, or wherein the catalyst is embedded or a solid support, or is located on the surface of a solid support.

24. The process according to claim 23, wherein the solid support comprises an inorganic material selected from the group consisting of silica, alumina, magnesia, titania, zirconia, montmorillonite, phyllosilicate, zeolites, talc, clays, layered double hydroxides, apatites, and any combination thereof; an organic polymer selected from polystyrene, polyethylene, polypropylene, polyvinylchloride, polytetrafluoro ethylene, polyacrylic acid methylester, polymethacrylic acid methylester, polycarbonates, polyethylene glycol, polyethylene terephthalate, poly(organo)siloxanes, and combinations thereof.

25. The process of claim 15, further comprising a solvent, a catalytic amount of base, or combination thereof.

26. The process according to claim 25, wherein said solvent is dioxane, TI-IF or a mixture thereof; said base is potassium t-butoxide; said catalytic amount of base is between 1-3 equivalents with respect to the catalyst, said catalyst is in an amount of 0.4% (mol %) with respect to the reactant (i.e., AE, 2-(methylamino) ethanol, GA, N,N-dimethyl GA, diaminoalkane, alcohol ED, ethanol, or DAE), or any combination thereof.

* * * * *